US009427731B2

(12) United States Patent
Allen et al.

(10) Patent No.: US 9,427,731 B2
(45) Date of Patent: Aug. 30, 2016

(54) SUPPORTED OLEFIN METATHESIS CATALYSTS

(75) Inventors: Daryl Allen, Pasadena, CA (US); Michael Giardello, Pasadena, CA (US)

(73) Assignee: MATERIA, INC., Pasadena, CA (US)

( * ) Notice: Subject to any disclaimer, the term of this patent is extended or adjusted under 35 U.S.C. 154(b) by 236 days.

(21) Appl. No.: 13/488,406

(22) Filed: Jun. 4, 2012

(65) Prior Publication Data

US 2013/0261312 A1   Oct. 3, 2013

Related U.S. Application Data

(63) Continuation of application No. PCT/US2010/058997, filed on Dec. 3, 2010.

(60) Provisional application No. 61/283,567, filed on Dec. 3, 2009.

(51) Int. Cl.
| | |
|---|---|
| B01J 31/22 | (2006.01) |
| C07F 15/00 | (2006.01) |
| C07C 6/04 | (2006.01) |
| C07C 67/333 | (2006.01) |
| C07C 67/475 | (2006.01) |
| C08G 61/08 | (2006.01) |
| B01J 31/16 | (2006.01) |

(52) U.S. Cl.
CPC ......... *B01J 31/2278* (2013.01); *B01J 31/1633* (2013.01); *B01J 31/2273* (2013.01); *B01J 31/2295* (2013.01); *C07C 6/04* (2013.01); *C07C 67/333* (2013.01); *C07C 67/475* (2013.01); *C07F 15/0046* (2013.01); *C08G 61/08* (2013.01); B01J 2231/543 (2013.01); B01J 2531/821 (2013.01); C07B 2200/11 (2013.01); C07C 2101/10 (2013.01); C07C 2531/22 (2013.01); C08G 2261/418 (2013.01); C08G 2261/419 (2013.01); Y02P 20/52 (2015.11)

(58) Field of Classification Search
CPC .......................... C07F 15/0046; B01J 31/2278
See application file for complete search history.

(56) References Cited

U.S. PATENT DOCUMENTS

| | | | |
|---|---|---|---|
| 5,312,940 | A | 5/1994 | Grubbs et al. |
| 5,342,909 | A | 8/1994 | Grubbs et al. |
| 6,620,955 | B1 | 9/2003 | Pederson et al. |
| 6,921,735 | B2 | 7/2005 | Hoveyda et al. |
| 7,026,495 | B1 | 4/2006 | Pederson et al. |
| 7,598,330 | B2 | 10/2009 | Grubbs et al. |
| 2003/0055262 | A1 | 3/2003 | Grubbs et al. |
| 2003/0100782 | A1 | 5/2003 | Grubbs et al. |
| 2006/0287450 | A1 | 12/2006 | Kohler et al. |
| 2006/0293526 | A1 | 12/2006 | Koehler et al. |
| 2007/0043180 | A1 | 2/2007 | Zhan |
| 2009/0170692 | A1 | 7/2009 | Ying et al. |

FOREIGN PATENT DOCUMENTS

| | | |
|---|---|---|
| EP | 2116302 A1 | 11/2009 |
| WO | 02/14376 A2 | 2/2002 |
| WO | 02/079208 A2 | 10/2002 |
| WO | 03/011455 A1 | 2/2003 |
| WO | 2005/016522 A1 | 2/2005 |
| WO | 2005/016524 A2 | 2/2005 |
| WO | 2007/017041 A1 | 2/2007 |
| WO | 2007/017047 A1 | 2/2007 |

OTHER PUBLICATIONS

Coperet et al. "Strategies to Immobilize Well-Defined Olefin Metathesis Catalysts: Supported Homogeneous Catalysis vs. Surface Organometallic Chemistry" Advanced Synthesis & Catalysis, 2007, vol. 349, pp. 78-92.*
International Search Report for PCT/US2010/058897 dated Sep. 28, 2011.
International Preliminary Report on Patentability for PCT/US2010/058897 dated Jun. 5, 2012.
Annis et al., J. Am. Chem. Soc., 121, 4147-4154 (1999).
Buchmeiser, New. J. Chem., 28, 549-557 (2004).
Chen et al., Org. Lett., 9, 3845-3848 (2007).
Clavier et al., Angew. Chem. Int. Ed., 46, 6786-6801 (2007).
Collman et al., J. Am. Chem. Soc., 105, 7288-7294 (1983).
Connon et al., Angew. Chem. Int. Ed., 41, 3835-3838 (2002).
Coperet et al., Adv. Synth. Catal., 349, 78-92 (2007).
Drago et al., Inorg. Chem., 24, 1983-1985 (1985).
Elias et al., Adv. Syn. Catal., 348, 751-762 (2006).
Garber et al., J. Am. Chem. Soc., 122, 8168-8179 (2000).
Grasa et al., J. Org. Chem., 66, 7729-7737 (2001).
Grubbs, R. H. Handbook of Metathesis, Table of Contents, Wiley-VCH: Weinheim, Germany (2003).
Halbach et al., J. Org. Chem., 70, 4687-4694 (2005).
Huang et al., Adv. Synth. Catal., 351, 188-206 (2009).
Lee et al., Tet. Lett., 46, 4501-4503 (2005).
Mayer et al., Adv. Synth. Catal., 344, 712-719 (2002).
Nguyen et al., J. Organomet. Chem., 497, 195-200 (1995).
Prühs et al., Organometallics, 23, 280-287 (2004).
Sanford et al., J. Am. Chem. Soc., 123, 749-750 (2001).
Scholl et al., Org. Lett., 6, 953-956 (1999).
Schürer et al., Angew. Chem. Int. Ed., 39, 3898-3901 (2000).
Schwab et al., J. Am. Chem. Soc., 118, 100-110 (1996).
Tollner et al., Science, 278, 2100-2102 (1997).
Yao, Angew. Chem. Int. Ed., 39, 3896-3898 (2000).

* cited by examiner

*Primary Examiner* — Joseph Kosack
(74) *Attorney, Agent, or Firm* — J. A. Lindeman & Co., PLLC

(57) ABSTRACT

Supported olefin metathesis catalysts are disclosed, and more particularly, a supported catalyst complex comprising a catalyst composed of a Group 8 transition metal complex comprising a labile ligand and a non-labile ligand and a support, wherein the metal complex and the support are linked together by one or more linkers, in which one of the linkers connects the labile ligand of the complex to the support and the same or a different linker connects the non-labile ligand of the complex to the support. A method for preparing a supported catalyst complex is further disclosed. The invention further relates to the use of the supported olefin metathesis catalyst in performing metathesis reactions. The invention has utility in the fields of catalysis, organic synthesis, polymer chemistry, and industrial and fine chemicals chemistry.

22 Claims, 14 Drawing Sheets

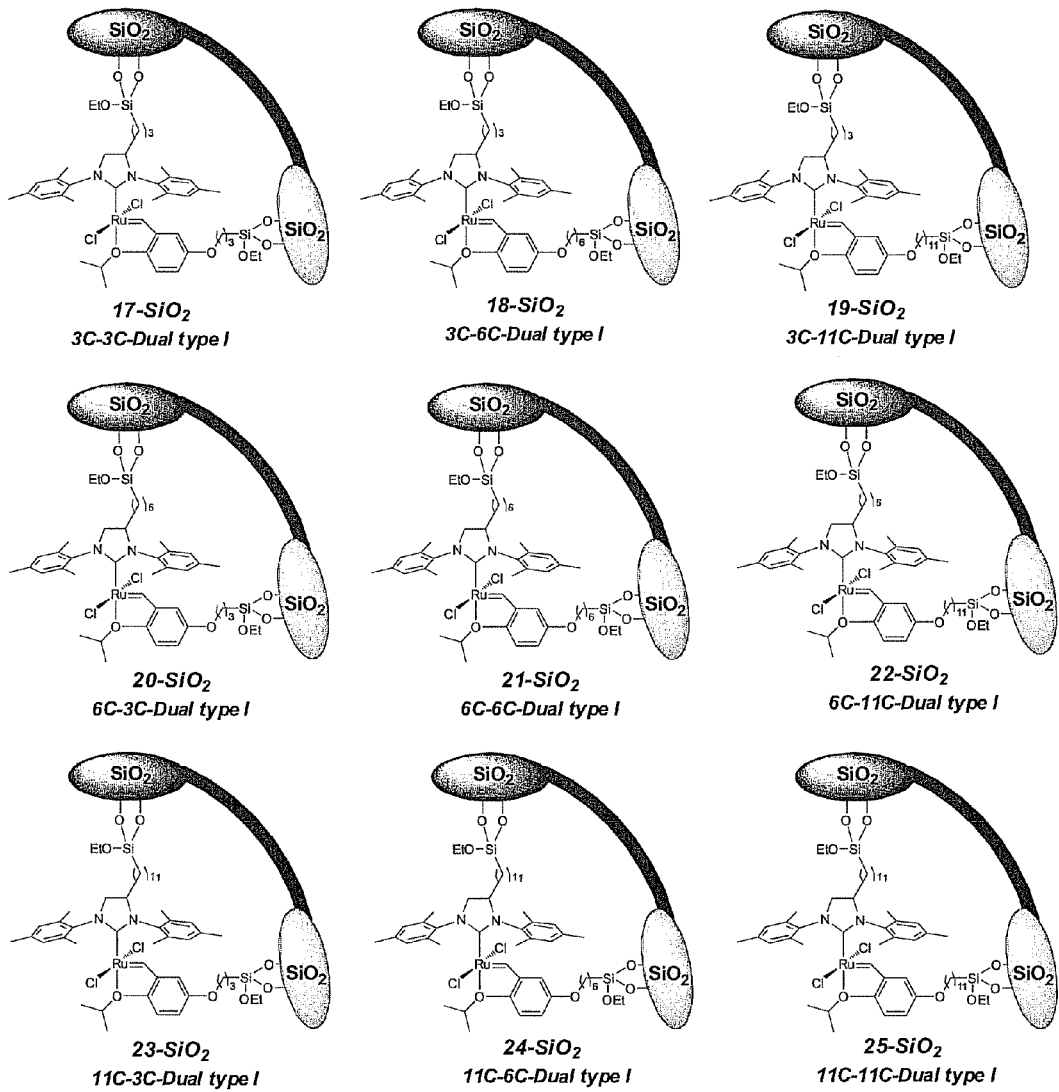
FIG. 1. Type I Supported Catalysts

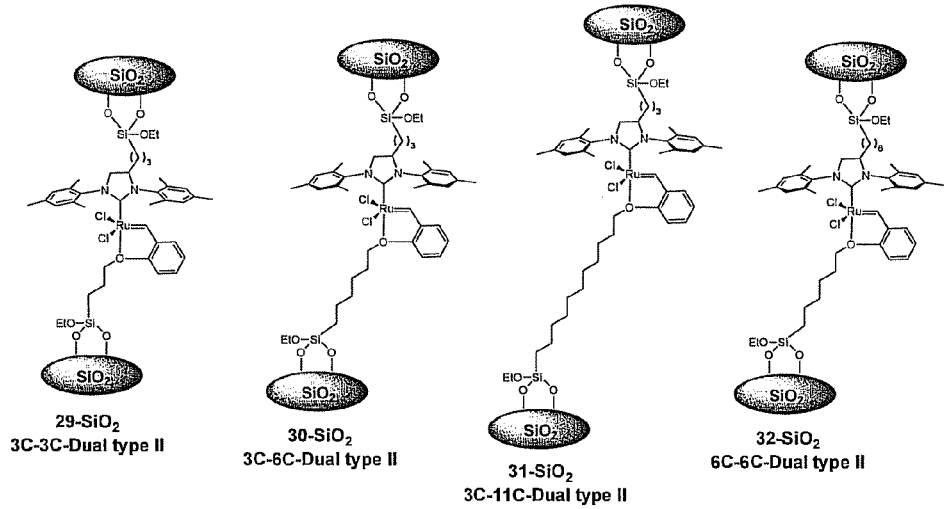
FIG. 2. Type II Supported Catalysts
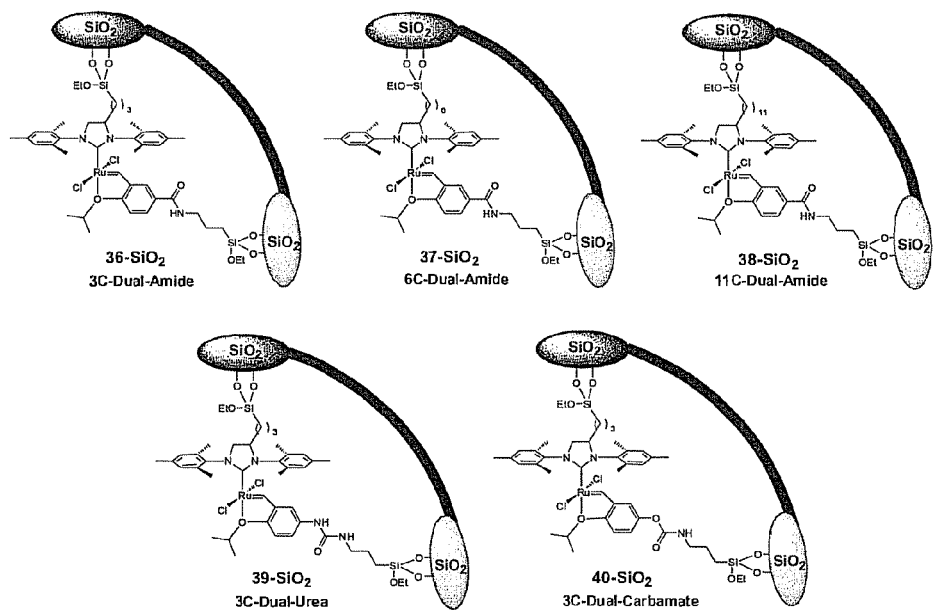
FIG. 3. Supported Catalysts derived from Styrenic Amide 33, Styrenic Urea 34 and Styrenic Carbamate 35

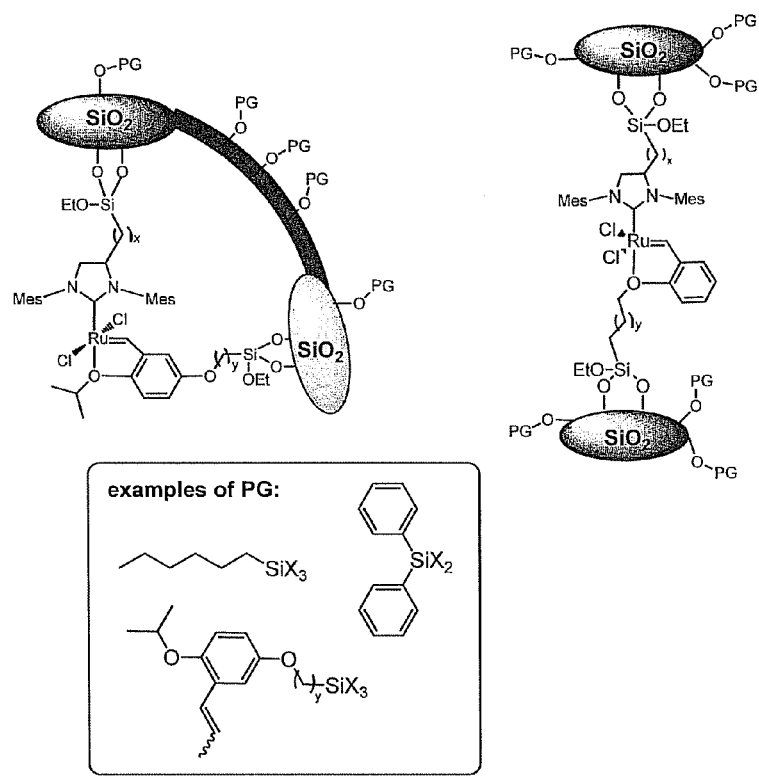
FIG. 4. Post-silica surface modification of supported catalysts with inert or functionalized silane precursors

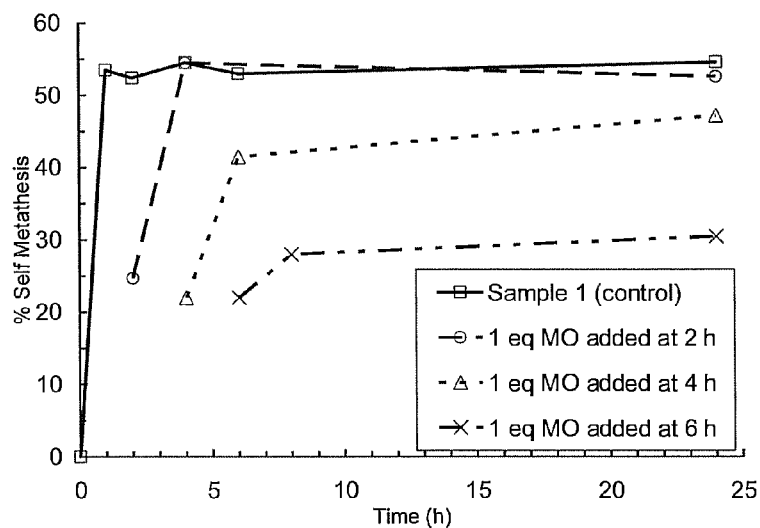
FIG. 5. Self-metathesis of methyl oleate using 3-C-mono-supported catalyst 627
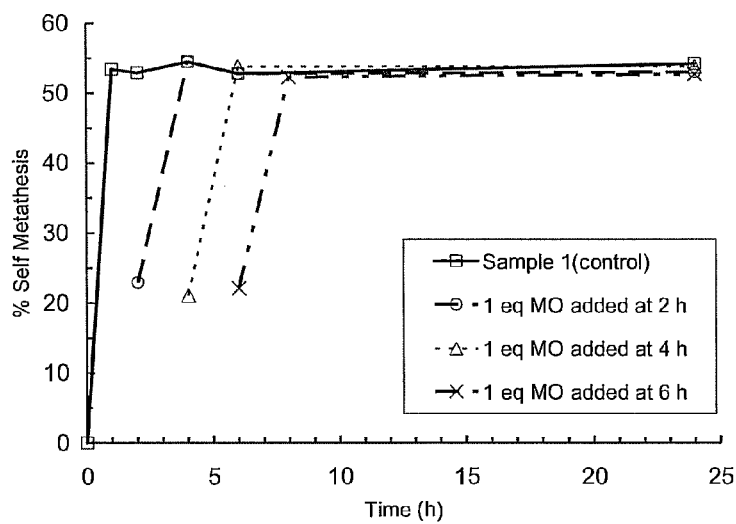
FIG. 6. Self-metathesis of methyl oleate using 17-SiO$_2$

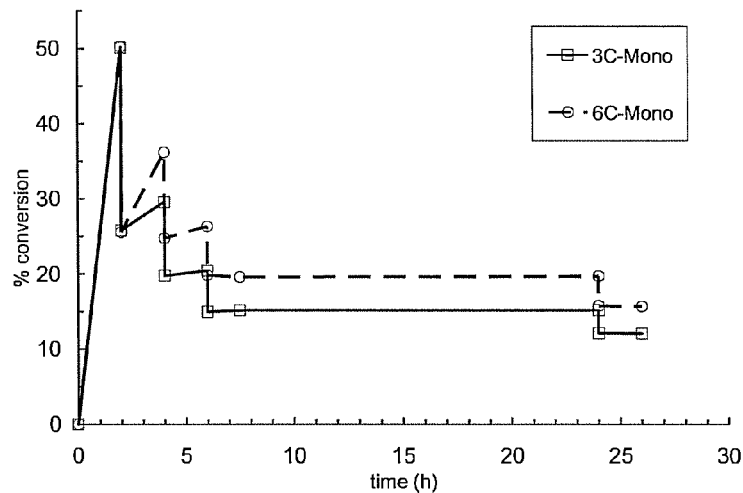
FIG. 7. Self-metathesis of methyl oleate using 3-C and 6-C-mono-supported catalysts 627
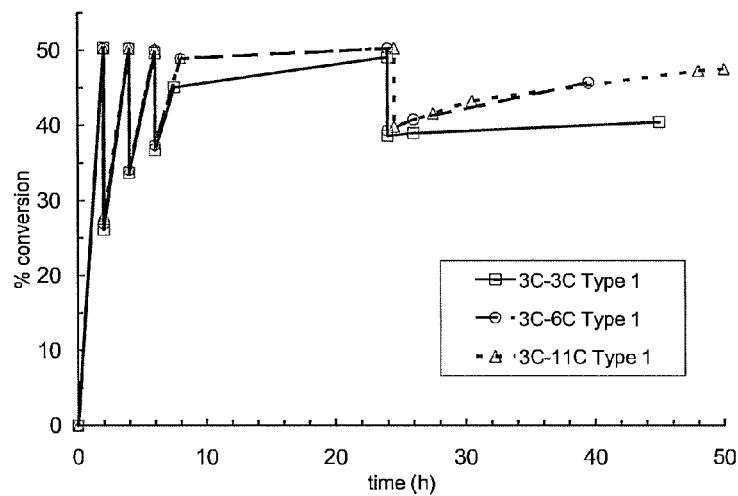
FIG. 8. Self-metathesis of methyl oleate using 17-, 18-, and 19-$SiO_2$

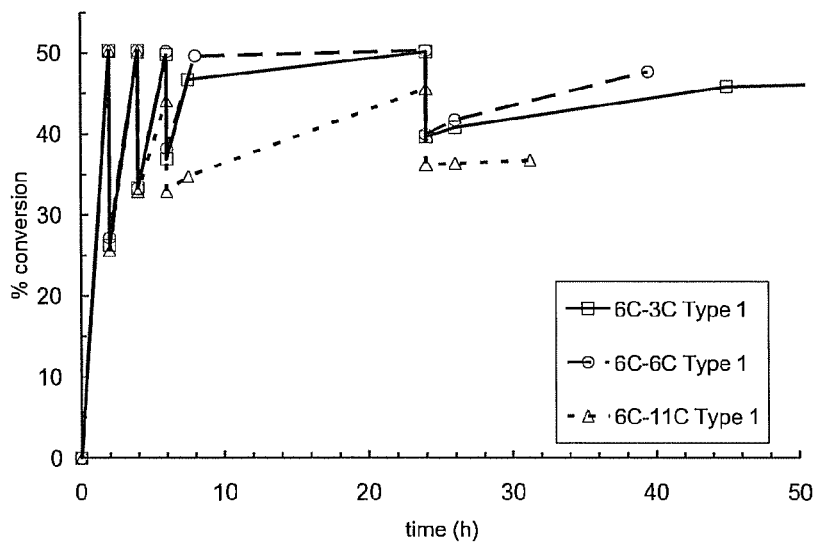
FIG. 9. Self-metathesis of methyl oleate using 20-, 21-, and 22-SiO$_2$
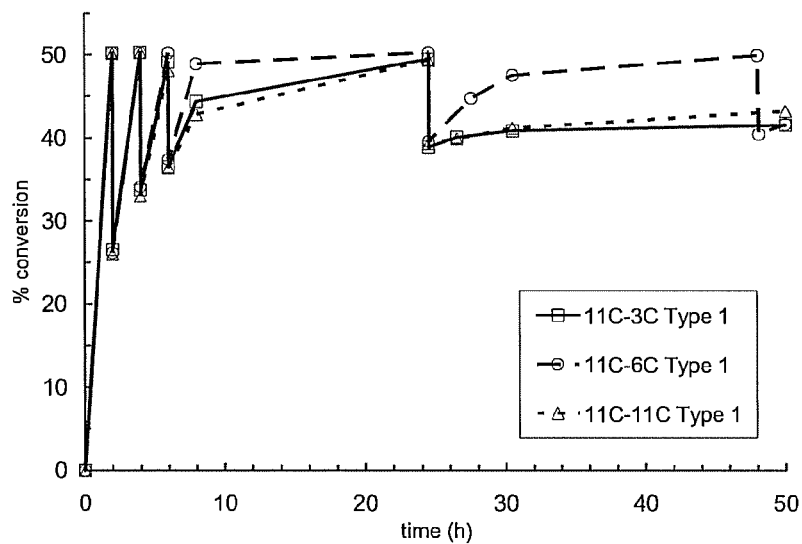
FIG. 10. Self-metathesis of methyl oleate using 23-, 24-, and 25-SiO$_2$

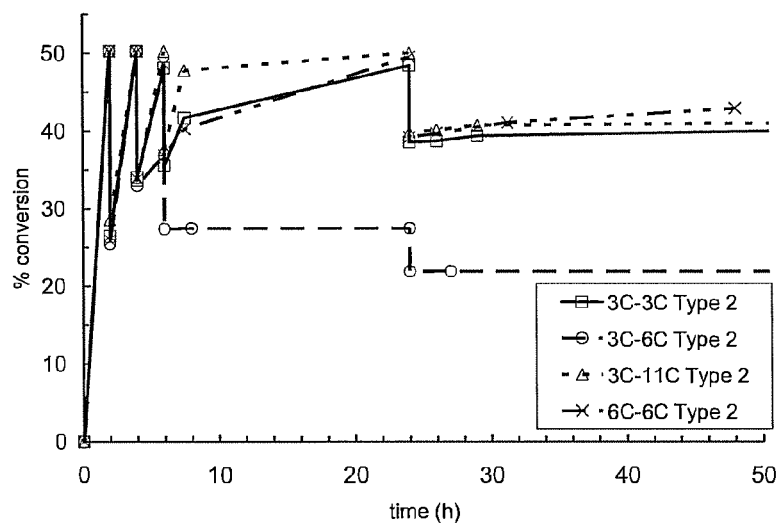
FIG. 11. Self-metathesis of methyl oleate using 29-, 30-, and 31-, and 32-SiO$_2$
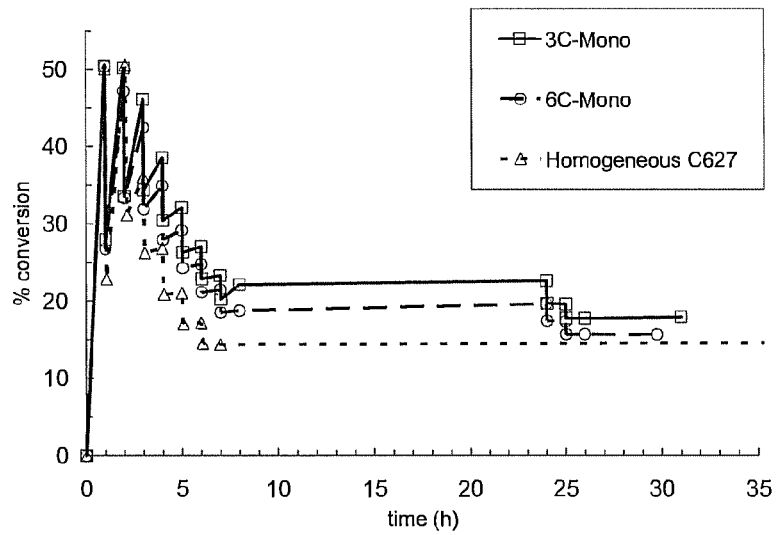
FIG. 12. Self-metathesis of 5-decenyl acetate using 3-C-and 6-C-mono-supported catalysts 627 and homogeneous catalyst 627

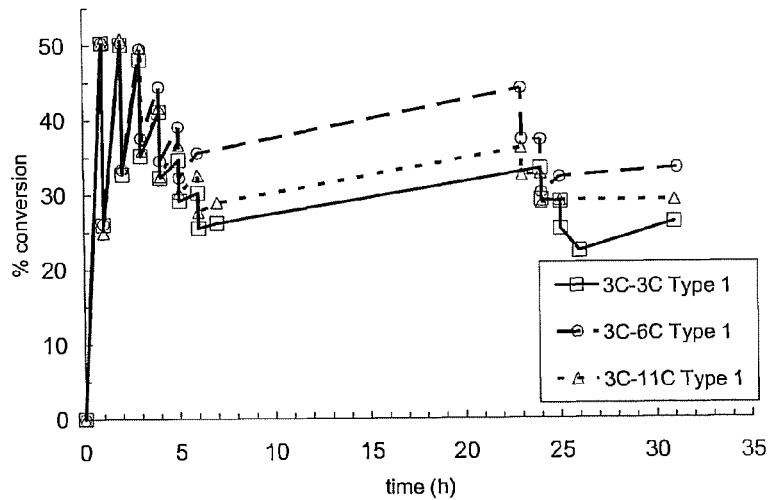
FIG. 13. Self-metathesis of 5-decenyl acetate using 17-, 18-, and 19-SiO$_2$
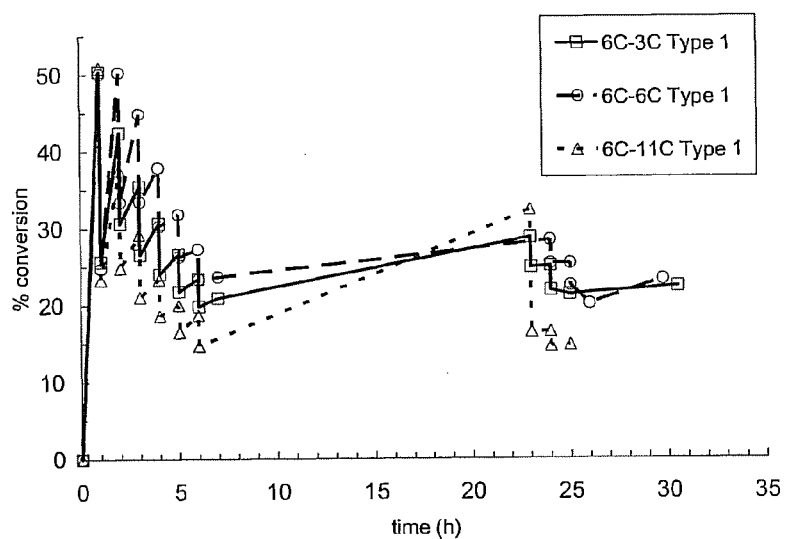
FIG. 14. Self-metathesis of 5-decenyl acetate using 20-, 21-, and 22-SiO$_2$

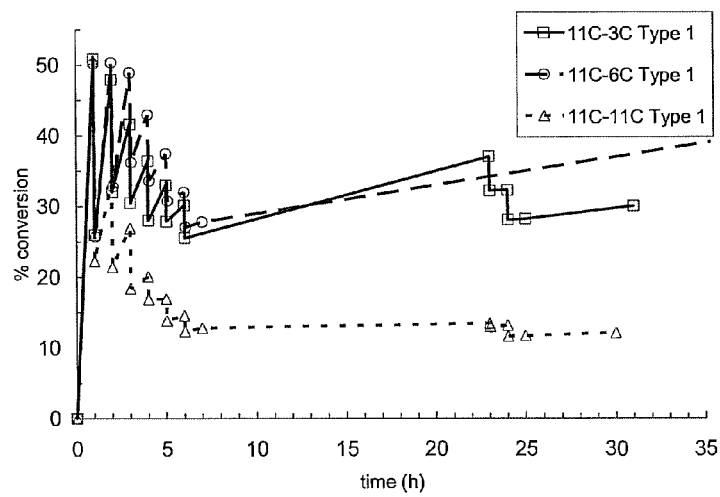
FIG. 15. Self-metathesis of 5-decenyl acetate using 23-, 24-, and 25-SiO$_2$
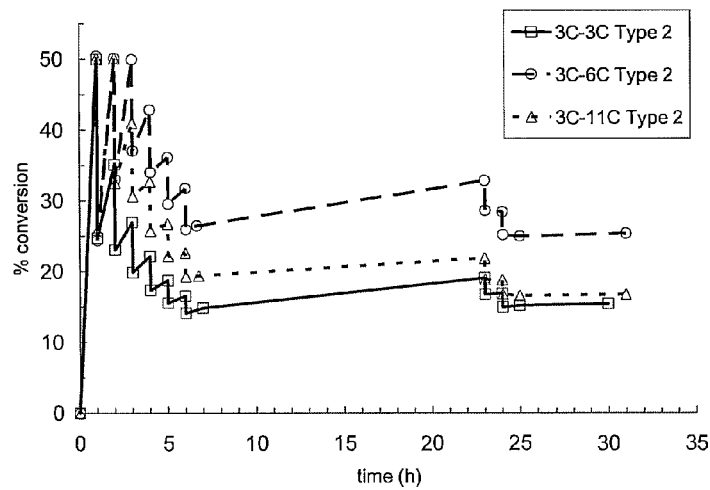
FIG. 16. Self-metathesis of 5-decenyl acetate using 29-, 30-, and 31-SiO$_2$

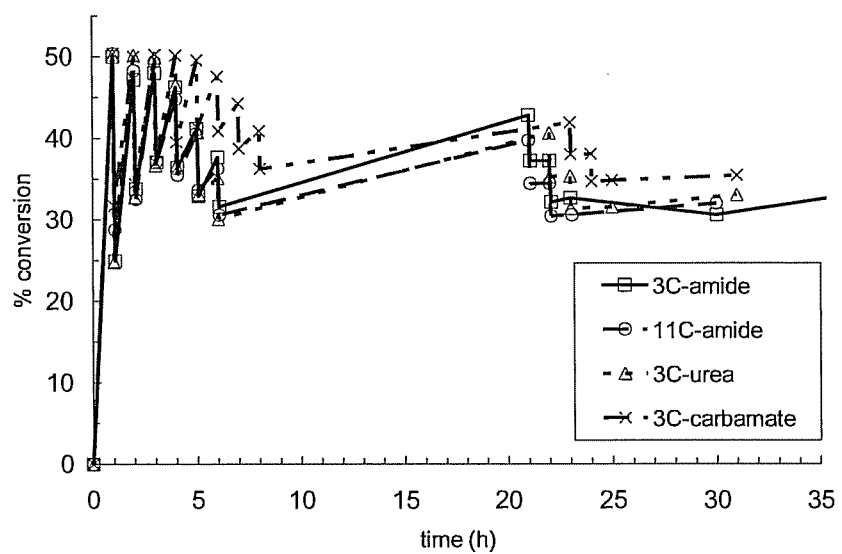
FIG. 17. Self-metathesis of 5-decenyl acetate using 35-, 37-, 38-, and 39-SiO$_2$

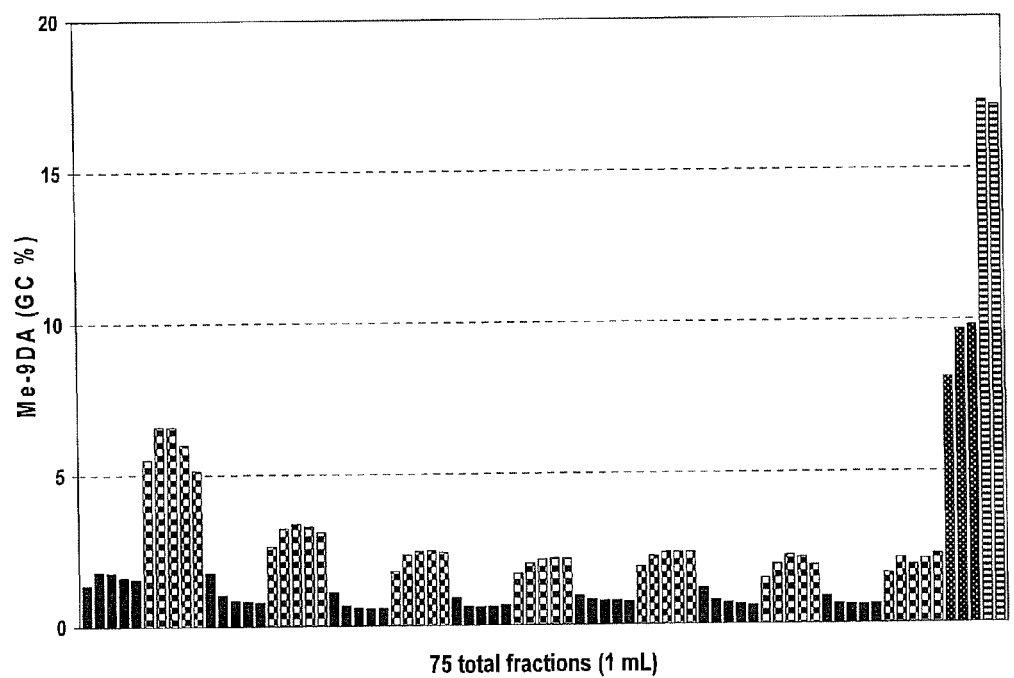
FIG. 18. HPLC standard screening protocol for the octenolysis of Soy FAME

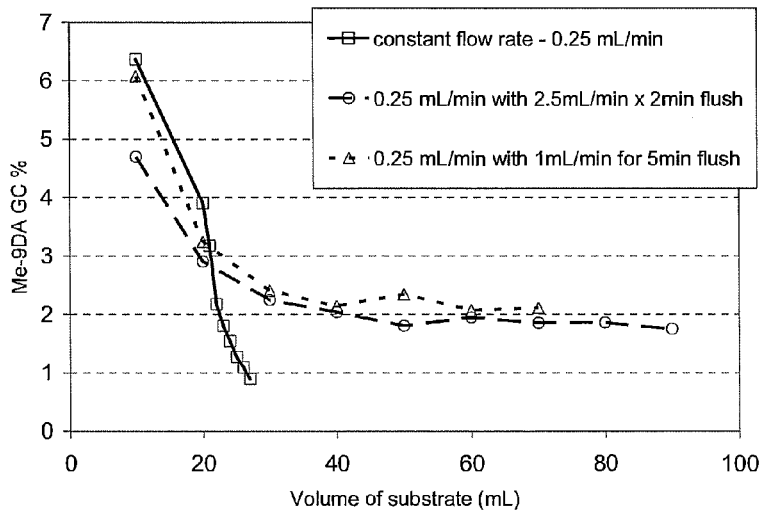
FIG. 19. Difference observed between constant flow rate and variable flow rates for the octenolysis of soy FAME using catalyst 24-SiO$_2$ under the HPLC screening conditions
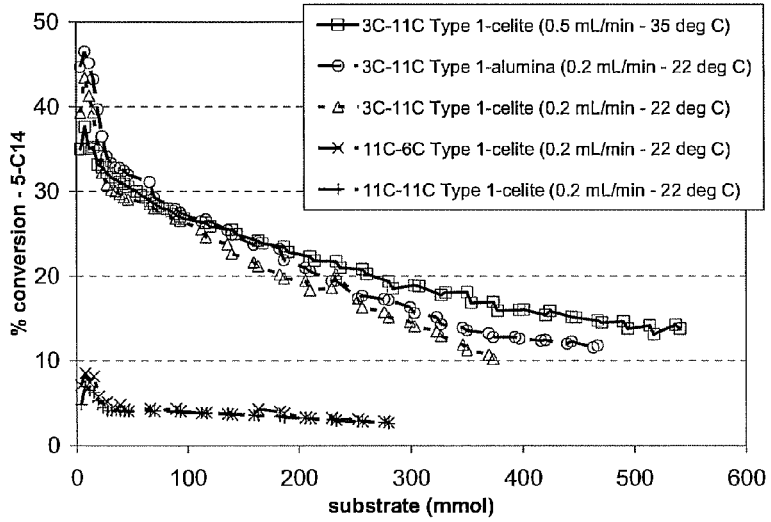
FIG. 20. Self-metathesis of 5-C$_{14}$ substrate using 19-, 24-, and 25-SiO$_2$ under various conditions

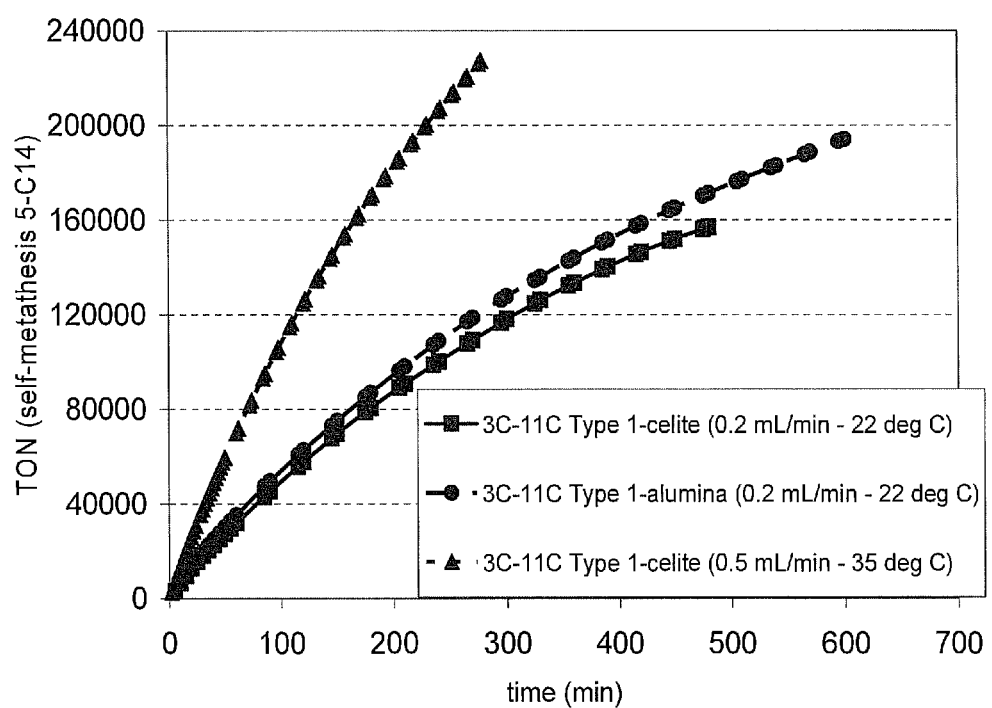
FIG. 21. Turnover number for the self-metathesis of 5-$C_{14}$ substrate using 19-$SiO_2$ under various conditions.

Di-substituted RCM:
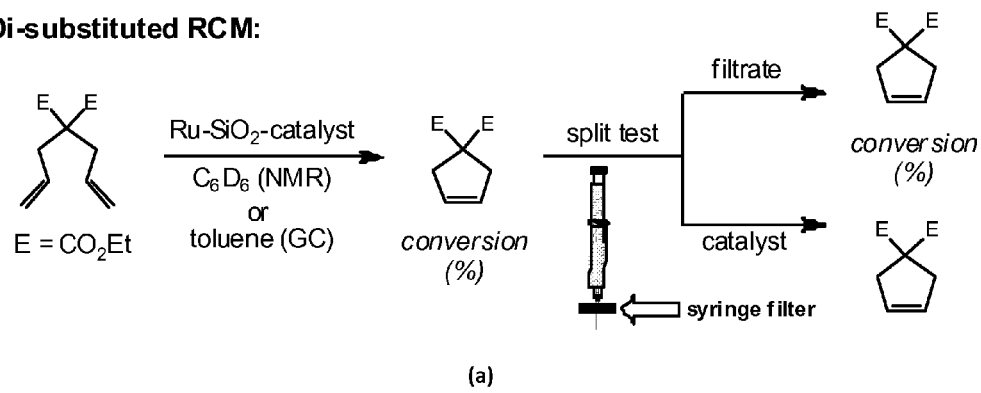
(a)
Tri-substituted RCM:
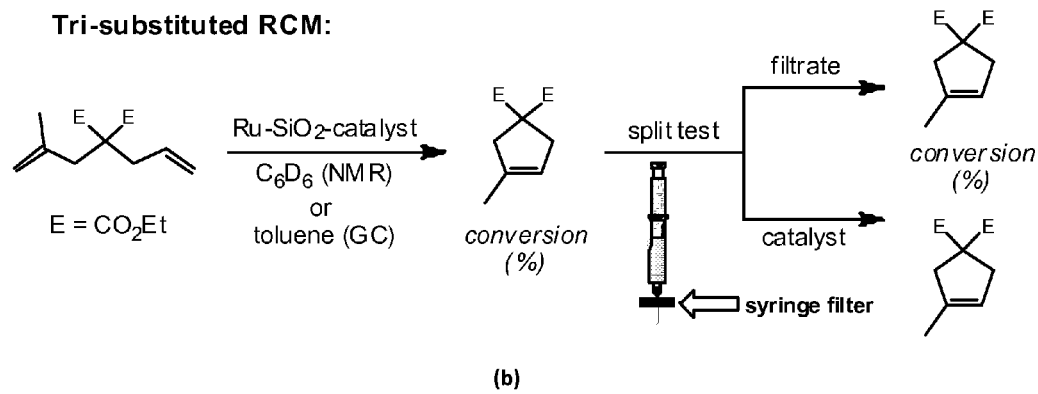
(b)
Figure 22

SUPPORTED OLEFIN METATHESIS CATALYSTS

CROSS REFERENCE TO RELATED APPLICATIONS

This application is a continuation of international application no. PCT/US2010/058997, having an international filing date of Dec. 3, 2010, and which claims priority to U.S. Provisional Application Ser. No. 61/283,567, filed Dec. 3, 2009, the contents of which are herein incorporated by reference.

TECHNICAL FIELD

This invention relates generally to organometallic olefin metathesis catalysts, and more particularly to the preparation of such catalysts and supported catalysts derived therefrom, as well as the use of such catalysts and supported catalysts in the metathesis of olefins and olefin compounds. The invention has utility in the fields of catalysis, organic synthesis, polymer chemistry, and industrial and fine chemicals chemistry.

BACKGROUND

Olefin metathesis has emerged as a unique and powerful transformation for the interconversion of olefinic hydrocarbons, namely due to the development of well-defined catalysts. See Grubbs, R. H. *Handbook of Metathesis*, Wiley-VCH: Weinheim, Germany (2003). The use of ruthenium alkylidene complexes has greatly expanded the scope of this process due to increased tolerance of organic functionality, moisture and oxygen. However, even with these advances, catalyst lifetime and efficiency represent the major limiting factors in the further development of this technology. Thus, the development of methods to reduce catalyst decomposition and increase the overall efficiency is highly desired. One such approach is to anchor the catalyst onto a solid support, such as silica gel, which is known to prevent bimolecular decomposition via site isolation. See, e.g. Collman, J. P. et al. *J. Am. Chem. Soc.*, 105, 7288-7294 (1983); Drago, R. S. et al., *Inorg. Chem.*, 24, 1983-1985 (1985); Tollner, K. et al., *Science*, 278, 2100-2102 (1997); and Annis, D. A. et al., *J. Am. Chem. Soc.*, 121, 4147-4154 (1999). Likewise, the resulting supported catalysts have the added benefit of being recyclable which will increase the overall catalytic efficiency, as well as the production of materials that are free of ruthenium contamination.

A number of reports have been published employing various strategies to obtain solid supported olefin metathesis catalysts. See, e.g. Buchmeiser, M. R. *New. J. Chem.*, 28, 549-557 (2004); Coperet, C.; Basset, J.-M. *Adv. Synth. Catal.*, 349, 78-92 (2007); Clavier, H.; Grela, K.; and Kirschning, A.; Mauduit, M.; Nolan, S. P. *Angew. Chem. Int. Ed.*, 46, 6786-6801 (2007). These consist of anchoring the catalytic moiety, via a number of positions within the catalyst framework, to a variety of solid supports, such as organic polymers or inorganic oxides. Of the various strategies, immobilization through a chelating alkylidene ligand has been the most widely employed [see Garber, S. B.; Kingsbury, J. S.; Gray, B. L.; Hoveyda, A. H. *J. Am. Chem. Soc.* 122, 8168, (2000); A. H. Hoveyda U.S. Pat. No. 6,921,735; Chen, S.-W.; Kim, J. H.; Song, C. E.; Lee, S.-g *Organic Letters*. 9, 3845 (2007); Connon, S.; Dunne, A. M.; Blechert, S. *Angew. Chem. Int. Ed.*, 39, 3898-3901 (2000); Lee, B. S.; Namgoong, S. K.; Lee, S.-g *Tetrahedron Letters* 46, 4501 (2005); Elias, X.; Pleixats, R.; Man, M. W. C.; Moreau, J. J. E. *Adv. Syn. Catal.* 348, 751, 2006. These catalysts operate via a release/return phenomenon with all the catalytic activity arising from a homogeneous species, which is susceptible to the same bimetallic decomposition pathways. Likewise, such systems cannot realize all the benefits of solid-phase catalysis, such as desirable continuous flow processes. Other approaches to catalyst immobilization have been carried out by exchanging the phosphine ligands of a Grubbs first generation catalyst with phosphines incorporated on a polystyrene-divinylbenzene polymer (PS-DVB) [see, e.g., S. T. Nguyen; R. H. Grubbs *J. Organomet. Chem.* 497, 195 (1995).]. Catalysts immobilized by such techniques, however, have been generally reviewed as providing reduced performance compared with homogeneous equivalents and as not being adaptable to flow-through technologies due to catalyst leaching [see, e.g., Coperet, C.; Basset, J.-M. *Adv. Synth. Catal.*, 349, 78-92 (2007)]. Still other strategies involve immobilization via alternative X-type ligands that replace the ancillary chlorides, such as fluorinated carboxylates, [see, e.g. Halbach, T. S.; Mix, S.; Fischer, D.; Maechling, S.; Krause, J. O.; Sievers, C.; Blechert, S.; Nuyken, O.; Buchmeiser, M. R. *J. Org. Chem.*, 70, 4687-4694 (2005)], or via functionalized NHC ligands. See, e.g. Schürer, S. C.; Gessler, S.; Buschmann, N.; Blechert, S. *Angew. Chem. Int. Ed.*, 39, 3898-3901 (2000); Mayer, M.; Buchmeiser, M. R.; Wurst, K. *Adv. Synth. Catal.*, 344, 712-719 (2002); Prühs, S.; Lehmann, C. W.; Fürstner, A. *Organometallics*, 23, 280-287 (2004); Koehler WO 2007/017047; WO 2007/017041; WO 2005/016522; and WO 2005/016524]. The latter is a very attractive approach as NHC ligands generally form strong bonds to the ruthenium center and are often the most substitutionally inert ligand within the catalyst coordination sphere.

However, anchoring the catalyst on a support can be problematic since various factors may affect the performance of such supported catalysts, including the reactivity of the functional group on the catalyst, the stability of the catalyst once anchored on the support, and the ability of the catalyst to perform as an effective catalyst after it has been grafted onto a support.

Despite the advances achieved in preparing olefin metathesis catalysts, including supported catalysts, a continuing need in the art exists for improved supported catalyst systems, as well as precursor complexes that are capable of being used in such systems.

SUMMARY OF THE DISCLOSURE

The invention is directed to addressing one or more of the aforementioned concerns, and, in one embodiment, provides a supported catalyst complex comprising a catalyst composed of a Group 8 transition metal complex comprising a labile ligand and a non-labile ligand and a support, wherein the metal complex and the support are linked together by one or more linkers, in which one of the linkers connects the labile ligand of the complex to the support and the same or a different linker connects the non-labile ligand of the complex to the support.

The invention is further directed to a method for preparing a supported catalyst complex, comprising contacting at least one non-labile ligand precursor and at least one labile ligand precursor with at least one Group 8 transition metal complex having multiple coordinated ligands, in which the non-labile ligand and the labile ligand precursors are exchanged via ligand exchange reactions with the coordinated ligands of the metal complex. Both the non-labile and the labile ligands comprise linkers for attachment to a support. The metal complex is further contacted with a support in order to link the metal complex to the support via the linkers.

In another aspect, the invention relates to the use of the supported olefin metathesis catalyst in performing metathesis reactions, and in particular to a method of performing an olefin metathesis reaction comprising the step of contacting an olefin with the supported catalyst described herein. The metathesis reaction may be a ring-closing metathesis reaction, a ring-opening cross metathesis reaction, a ring-opening metathesis polymerization reaction, a cross metathesis reaction, a self-metathesis reaction, an ethenolysis reaction, an alkenolysis reaction, or an acyclic diene metathesis polymerization reaction, as well as combinations of such metathesis reactions.

BRIEF DESCRIPTION OF THE DRAWINGS

FIG. 1 depicts Type I dual-supported catalyst complexes as described in the Examples.

FIG. 2 depicts Type II dual-supported catalyst complexes as described in the Examples.

FIG. 3 depicts various other linked dual-supported catalyst complexes as described in the Examples.

FIG. 4 depicts the post silica surface modified dual-supported catalyst complexes described in the Examples.

FIGS. 5-11 depict self-metathesis results of methyl oleate using mono- and dual-supported catalysts as described in the Examples.

FIGS. 12-17 depict self-metathesis results of 5-decenyl acetate using homogeneous, mono- and dual-supported catalysts as described in the Examples.

FIGS. 18-19 depict the hexenolysis of soybean FAME using HPLC flow conditions through a fixed catalysts bed employing dual-supported catalysts as described in the Examples.

FIGS. 20-21 depict the self-metathesis of the 5-$C_{14}$ substrate using HPLC flow conditions through a fixed catalysts bed employing dual-supported catalysts as described in the Examples.

FIG. 22(a) depicts an RCM formation of a di-substituted olefin for split testing of dual-supported catalysts.

FIG. 22(b) depicts an RCM formation of a tri-substituted olefin for split testing of dual-supported catalysts.

DETAILED DESCRIPTION OF THE DISCLOSURE

Terminology and Definitions

Unless otherwise indicated, the invention is not limited to specific reactants, substituents, catalysts, reaction conditions, or the like, as such may vary. It is also to be understood that the terminology used herein is for the purpose of describing particular embodiments only and is not to be interpreted as being limiting.

As used in the specification and the appended claims, the singular forms "a," "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "including" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above.

A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, or —(CO)-aralkyl, and the term "acyloxy" refers to substituents having the formula —O(CO)-alkyl, —O(CO)-aryl, or —O(CO)-aralkyl, wherein "alkyl," "aryl, and "aralkyl" are as defined above.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic, or polycyclic.

The terms "halo" and "halogen" are used in the conventional sense to refer to a chloro, bromo, fluoro, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)-X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ alkyl)), di-($C_1$-$C_{24}$ haloalkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl, thiocarbamoyl (—(CS)—$NH_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—$NH_2$), cyano(—C≡N), cyanato (—O—C≡N), thiocyanato (—S—C≡N), formyl (—(CO)—H), thioformyl (—(CS)—H), amino (—$NH_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl —$SO_2$—N(H) alkyl), $C_1$-$C_{24}$ dialkylaminosulfonyl —$SO_2$—N(alkyl)$_2$, $C_5$-$C_{24}$ arylsulfonyl (—$SO_2$-aryl), boryl (—$BH_2$), boron (—B(OH)$_2$), boronato (—B(OR)$_2$ where R is alkyl or other hydrocarbyl), phosphono (—P(O)(OH)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described hereinabove. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "labile and "non-labile", as used herein, refer to the relative ability of ligands so-described to remain coordinated to the transition metal complex. In this regard, and without being limited to this understanding, the non-labile ligand is thought to act as an anchoring ligand and remains coordinated to the metal center and attached to the support via a linker and optionally attached to the non-labile ligand and the support during an olefin metathesis reaction, while the labile ligand dissociates from the metal complex, but still remains attached to the support via a linker connecting the labile ligand and the support. The term "hemi-labile" generally refers to ligands having more than one attachment to a Group 8 transition metal complex, wherein one or more of the attachments to the complex may be labile and/or non-labile.

Supported Catalyst Complex

In a first aspect, the invention provides a supported catalyst complex comprising a catalyst composed of a Group 8 transition metal complex comprising a labile ligand and a non-labile ligand and a support. The metal complex and the support are linked together by one or more linkers, in which one of the linkers connects the labile ligand of the complex to the support and the same or a different linker connects the non-labile ligand of the complex to the support.

The labile ligand and the non-labile ligand are independently selected from a neutral electron donor ligand, an anionic ligand, a hemi-labile ligand, or a combination thereof. Preferably, both ligands are selected from a neutral electron donor ligand, an anionic ligand, a cationic ligand, a hemi-labile ligand, or a combination thereof. In certain embodiments, the non-labile and labile ligands may be the same, provided one of the ligands functions as a non-labile ligand while another functions as a labile ligand and both remain attached to the support. The non-labile and labile ligands are preferred to be different, however. In addition, it is generally preferred that at least one of the ligands be a non-phosphine ligand, or that the complex is not a bis-phosphine ruthenium-based catalyst. The catalyst may contain more than one labile and/or non-labile ligand, provided at least one labile ligand and at least one non-labile ligand is attached to the support.

In particular embodiments, the non-labile ligand is selected from N-heterocyclic carbenes, acyclic diaminocarbenes, cyclic alkyl amino carbenes, 1,2,4-triazol-5-ylidene ligands, thiazol-2-ylidene ligands, salen ligands, Schiff base ligands, or a combination thereof. More particularly, the non-labile ligand is selected from halogen, pseudo halide, alkyl, aryl, alkoxide, aryloxide, alkyldiketonate, aryldiketonate, carboxylate, alkylsulfonate, arylsulfonate, alkylthio, alkylsulfonyl, alkylsulfinyl, siloxy, or a combination thereof. In a more preferred embodiment, the non-labile ligand is selected from F, Cl, Br, I, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, trifluoromethanesulfonate or a combination thereof. Of course, when such ligands contain monovalent moieties, such as halogens, any attachment to the support and the complex will occur through other moieties that can be functionalized with a linker group for attachment to the support.

In more particular embodiments, the labile ligand is selected from an N-heterocyclic carbene, alkylidenes, phosphine, pyridine, substituted pyridine, chelating ligands, thiophene, pyrrole, imines, amines, alcohols, silanols or a combination thereof.

The linkers are independently selected from hydrocarbylene, substituted hydrocarbylene, heteroatom-containing hydrocarbylene, and substituted heteroatom-containing hydrocarbylene, each of which may optionally comprise one or more functional groups. Preferably, the linkers comprise a functional group selected from siloxy, siloxane, silanol, amine, amide, imine, alcohol, alkoxide, phenoxide, acetal, aldehyde, carboxylic acid, urea, ether, ester, anhydride, carbamate, carbonates, thiols, sulfonyl, amino sulfonyl, hydrazine, phosphate, phosphite, phosphonate, phosphonite, phosphinate, phosphinite, phosphine, phosphine oxide, or a combination thereof. In particular embodiments, the linkers advantageously comprise a siloxy and/or siloxane group and, optionally, one or more amide, urea, ether, ester, anhydride, or carbamate groups. The linkers may also simply be one or more such functional groups that provide direct attachment between the support and the non-labile and/or labile ligands (i.e., without the hydrocarbylene groups described above).

In certain aspects of the invention, the linkers have the structure -A-Fn, wherein A is a divalent hydrocarbon moiety (i.e., methylenes (—CH$_2$—)$_n$, wherein n is an integer ranging from 0-24) selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the of arylalkylene can be substituted or unsubstituted, and wherein heteroatoms and/or functional groups may be present in either the aryl or the alkyl portions of the alkylene groups, arylalkylene groups, and Fn is a functional group. While the functional groups are not necessarily limited, suitable functional groups include siloxy, siloxane, silanol, amine, amide, imine, alcohol, alkoxide, phenoxide, acetal, aldehyde, carboxylic acid, urea, ether, ester, anhydride, carbamate, carbonates, thiols, sulfonyl, amino sulfonyl, hydrazine, phosphate, phosphite, phosphonate, phosphonite, phosphinate, phosphinite, phosphine, phosphine oxide, or a combination thereof. Both the divalent hydrocarbon moiety A or the functional group Fn may also be absent, i.e., they are optionally present, with the remaining moiety A or the functional group Fn serving to provide attachment between the support and the non-labile ligand or the labile ligand.

Suitable linkers include those having the structure -A-Si(O(CH$_2$)$_n$CH$_3$)$_3$, wherein n is an integer ranging from 0-3 and A is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the of arylalkylene can be substituted or unsubstituted, and wherein heteroatoms and/or functional groups may be present in either the aryl or the alkyl portions of the alkylene and arylalkylene groups.

In some aspects of the invention, the linkers may comprise heteroatoms and/or functional groups in either the aryl or alkyl portions of the alkylene or arylalkylene groups A, in addition to the functional groups Fn. Such heteroatoms and/or functional groups may be located at any position in the alkylene or arylalkylene groups. In a preferred embodiment, such heteroatoms and/or functional groups are located at the attachment point of the linker to the ligand. While not limited thereto, the introduction of such heteroatoms and/or functional groups may be accomplished through a reaction between a ligand precursor and a linker having the structure -A-Fn, where A and Fn are as described above. Suitable heteroatoms introduced through such reactions include, O, N, and S, while representative functional groups formed by the reaction between a ligand precursor and a linker include amide, urea, and carbamate groups. Other combinations based on the selection of suitable functional groups present on a ligand precursor and the linker will be apparent to the skilled artisan, including, but not limited to, siloxy and amide, siloxy and urea, siloxy and ether, siloxy and ester, siloxy and anhydride, siloxy and carbamate, siloxane and amide, siloxane and urea, siloxane and ether, siloxane and ester, siloxane and anhydride, and siloxane and carbamate attachments.

In general, the support also comprises a functional group selected from hydroxyl, siloxy, siloxane, amide, urea, ether, ester, anhydride, carbamate, or a combination thereof. Suitable combinations of functional groups for the support and the linkers may be selected to provide attachments for the non-labile and labile ligands as desired. Suitable combinations include siloxy and amide, siloxy and urea, siloxy and ether, siloxy and ester, siloxy and anhydride, siloxy and carbamate, siloxane and amide, siloxane and urea, siloxane and ether, siloxane and ester, siloxane and anhydride, siloxane and carbamate attachments. Other combinations will be apparent to the skilled artisan, The olefin metathesis catalyst complex according to the invention is preferably a Group 8 transition metal complex having the structure of formula (II)

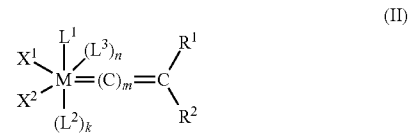

(II)

in which the various substituents are as follows:

M is a Group 8 transition metal;
L$^1$, L$^2$ and L$^3$ are neutral electron donor ligands;
n is 0 or 1, such that L$^3$ may or may not be present;
m is 0, 1, or 2;
k is 0 or 1;
X$^1$ and X$^2$ are anionic ligands; and
R$^1$ and R$^2$ are independently selected from hydrogen, hydrocarbyl, substituted hydrocarbyl, heteroatom-containing hydrocarbyl, substituted heteroatom-containing hydrocarbyl, and functional groups,
wherein any two or more of X$^1$, X$^2$, L$^1$, L$^2$, L$^3$, R$^1$, and R$^2$ can be taken together to form one or more cyclic groups, and further wherein any one or more of X$^1$, X$^2$, L$^1$, L$^2$, L$^3$, R$^1$, and R$^2$ may be attached to a support. In addition, any two or more of X$^1$, X$^2$, L$^1$, L$^2$, L$^3$, R$^1$, and R$^2$ are attached to the support via the linkers, such that the complex comprises a labile ligand connected to the support and the same or a different linker connects a non-labile ligand of the complex to the support.

Preferred catalysts contain Ru or Os as the Group 8 transition metal, with Ru particularly preferred.

Numerous embodiments of the catalysts useful in the reactions disclosed herein are described in more detail infra.

For the sake of convenience, the catalysts are described in groups, but it should be emphasized that these groups are not meant to be limiting in any way. That is, any of the catalysts useful in the invention may fit the description of more than one of the groups described herein.

A first group of catalysts, then, are commonly referred to as First Generation Grubbs-type catalysts, and have the structure of formula (II). For the first group of catalysts, M and m are as described above, and n, $X^1$, $X^2$, $L^1$, $L^2$, $L^3$, $R^1$, and $R^2$ are described as follows.

For the first group of catalysts, n is 0, and $L^1$ and $L^2$ are independently selected from phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and thioether. Exemplary ligands are trisubstituted phosphines.

$X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

$R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or —C=C(CH$_3$)$_2$.

Any two or more (typically two, three, or four) of $X^1$, $X^1$, $L^1$, $L^2$, $L^3$, $R^1$, and $R^2$ can be taken together to form a cyclic group, including bidentate or multidentate ligands, as disclosed, for example, in U.S. Pat. No. 5,312,940 to Grubbs et al. When any of $X^1$, $X^1$, $L^1$, $L^2$, $L^3$, $R^1$, and $R^2$ are linked to form cyclic groups, those cyclic groups may contain 4 to 12, preferably 4, 5, 6, 7 or 8 atoms, or may comprise two or three of such rings, which may be either fused or linked. The cyclic groups may be aliphatic or aromatic, and may be heteroatom-containing and/or substituted. The cyclic group may, in some cases, form a bidentate ligand or a tridentate ligand. Examples of bidentate ligands include, but are not limited to, bisphosphines, dialkoxides, alkyldiketonates, and aryldiketonates.

A second group of catalysts, commonly referred to as Second Generation Grubbs-type catalysts, have the structure of formula (II), wherein $L^1$ is a carbene ligand having the structure of formula (III)

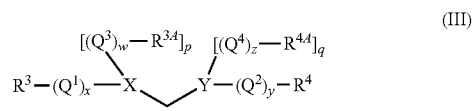

such that the complex may have the structure of formula (IV)

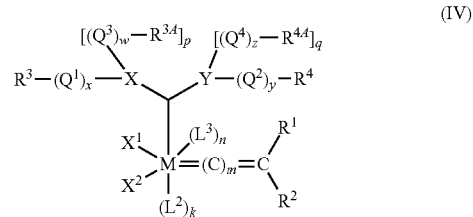

wherein M, m, n, $X^1$, $X^2$, $L^2$, $L^3$, $R^1$, and $R^2$ are as defined for the first group of catalysts, and the remaining substituents are as follows.

X and Y are heteroatoms typically selected from N, O, S, and P. Since O and S are divalent, p is necessarily zero when X is O or S, q is necessarily zero when Y is O or S, and k is zero or 1. However, when X is N or P, then p is 1, and when Y is N or P, then q is 1. In a preferred embodiment, both X and Y are N.

$Q^1$, $Q^2$, $Q^3$, and $Q^4$ are linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. Preferably, w, x, y, and z are all zero. Further, two or more substituents on adjacent atoms within $Q^1$, $Q^2$, $Q^3$, and $Q^4$ may be linked to form an additional cyclic group.

$R^3$, $R^{3A}$, $R^4$, and $R^{4A}$ are independently selected from hydrogen, hydrocarbyl, substituted hydrocarbyl, heteroatom-containing hydrocarbyl, and substituted heteroatom-containing hydrocarbyl.

In addition, any two or more of $X^1$, $X^2$, $L^1$, $L^2$, $L^3$, $R^1$, $R^2$, $R^3$, $R^{3A}$, $R^4$, and $R^{4A}$ can be taken together to form a cyclic group, and any two or more of $X^1$, $X^2$, $L^1$, $L^2$, $L^3$, $Q^1$, $Q^2$, $Q^3$, $Q^4$, $R^1$, $R^2$, $R^3$, $R^{3A}$, $R^4$, and $R^{4A}$ are attached to the support via the linkers. Any two or more of $X^1$, $X^2$, $L^1$, $L^2$, $L^3$, $R^1$, $R^2$, $R^3$, $R^{3A}$, $R^4$, and $R^{4A}$ can also be taken to be -A-Fn, wherein A and Fn have been defined above, or together to form a cyclic group, and any two or more of $X^1$, $X^2$, $L^2$, $L^3$, $Q^1$, $Q^2$, $Q^3$, $Q^4$, $R^1$, $R^2$, $R^3$, $R^{3A}$, $R^4$, and $R^{4A}$ may be attached to the support via the linkers.

Preferably, $R^{3A}$ and $R^{4A}$ are linked to form a cyclic group so that the carbene ligand has the structure of formula (V)

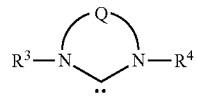

(V)

wherein $R^3$ and $R^4$ are defined above, with preferably at least one of $R^3$ and $R^4$, and more preferably both $R^3$ and $R^4$, being alicyclic or aromatic of one to about five rings, and optionally containing one or more heteroatoms and/or substituents. Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q is often, although again not necessarily, a two-atom linkage or a three-atom linkage.

Examples of N-heterocyclic carbene ligands and acyclic diaminocarbene ligands suitable as $L^1$ thus include, but are not limited to, the following where DIPP is diisopropylphenyl and Mes has been defined earlier:

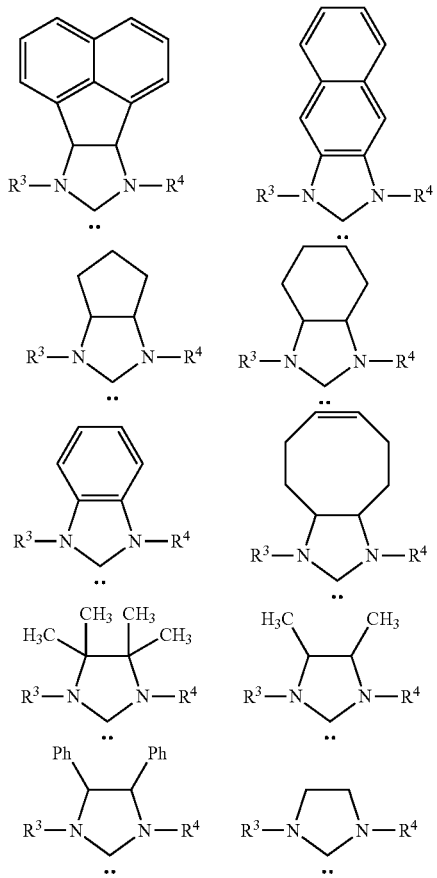

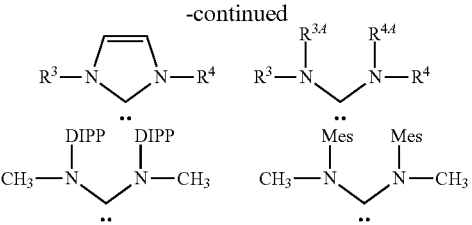

When M is ruthenium, then, the preferred complexes have the structure of formula (VI)

(VI)

In a more preferred embodiment, Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups here include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ are preferably independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Alternatively, any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents. In one further aspect, any one or more of $R^{11}$, $R^{12}$, $R^{13}$, and $R^{14}$ comprises one or more of the linkers.

In more particular aspects, $R^3$ and $R^4$ may be independently selected from alkyl, cycloalkyl, heteroalkyl, alkenyl, alkynyl, aryl, aryloxy, alkaryl, aralkyl, heteroaryl, and halo or halogen-containing groups. More specifically, $R^3$ and $R^4$ may be independently selected from $C_1$-$C_{20}$ alkyl, $C_5$-$C_{14}$ cycloalkyl, $C_1$-$C_{20}$ heteroalkyl, $C_5$-$C_{24}$ aryl, $C_5$-$C_{24}$ heteroaryl, $C_2$-$C_{24}$ alkenyl, $C_2$-$C_{12}$ alkynyl, $C_6$-$C_{24}$ aralkyl, $C_6$-$C_{24}$ alkaryl, or halide. Suitable alkyl groups include, without limitation, methyl, ethyl, n-propyl, isopropyl, isopropyl, n-butyl, isobutyl, t-butyl, octyl, decyl, and the like; suitable cycloalkyl groups include cyclopentyl, cyclohexyl and the like; suitable alkenyl groups include ethenyl, n-propenyl, isopropenyl, n-butenyl, isobutenyl, octenyl, decenyl, tetradecenyl, hexadecenyl, eicosenyl, tetracosenyl, and the like; suitable alkynyl groups include ethynyl, n-propynyl, and the like; suitable aryl groups include aryl groups containing one aromatic ring or two fused or linked aromatic rings, e.g., phenyl, naphthyl, biphenyl, diphenylether, diphenylamine, benzophenone, and the like; suitable aryloxy groups include phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like; suitable alkaryl groups include p-methylphenyl, 2,4-dimethylphenyl, p-cyclohexyl-phenyl, 2,7-dimethylnaphthyl, 7-cyclooctylnaphthyl, 3-ethyl-cyclopenta-1,4-diene, and the like; suitable aralkyl groups include p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like; suitable heteroaryl groups include pyrrolyl, pyrrolidinyl, pyridinyl, quinolinyl, indolyl, pyrimidinyl, imidazolyl, 1,2,4-triazolyl, tetrazolyl, and the like; and suitable heteroatom-containing alicyclic groups include pyrrolidino, morpholino, piperazino, piperidino, and the like.

By the description of $R^3$ and $R^4$ as independently selected from "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: hydroxyl, carbamido (—NH—(CO)—$NH_2$), cyano(—C≡N), cyanato (—O—C≡N), thiocyanato (—S—C≡N), formyl (—(CO)—H), thioformyl (—(CS)—H), amino (—$NH_2$), nitro (—$NO_2$), nitroso (—NO), sulfo (—$SO_2$—OH), sulfonato (—$SO_2$—$O^-$), boryl (—$BH_2$), borono (—$B(OH)_2$), boronato (—$B(OR)_2$ where R is alkyl or other hydrocarbyl), phosphono (—$P(O)(OH)_2$), phosphonato (—$P(O)(O^-)_2$), phosphinato (—$P(O)(O^-)$), phospho (—$PO_2$), and phosphino (—$PH_2$).

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. More particularly, $R^3$ and $R^4$ may be independently substituted with hydrogen, $C_1$-$C_4$ alkyl, $C_1$-$C_4$ alkoxy, $C_5$-$C_{14}$ aryl, substituted $C_5$-$C_{14}$ aryl, or halide. As an example, $R^3$ and $R^4$ are mesityl, or, more generally, phenyl substituted with one, two or three $C_1$-$C_4$ alkyl or $C_1$-$C_4$ alkoxy groups, or a combination thereof.

In some specific embodiments, $R^3$ and $R^4$ are independently selected from mesityl, mono-orthomethylphenyl, mono-ortho isopropylphenyl, 2,6-dimethylphenyl, 2,6-diisopropylphenyl, mono-orthofluorolphenyl, mono-ortho chlorolphenyl, 2,6-difluorophenyl, 2,6-dichlorophenyl, 3,5-bis-tert-butylphenyl, anthracenyl, acyclic N-heterocarbenes methyl-diisopropylphenyl amine and methyl-mesityl amine.

In a third group of catalysts having the structure of formula (II), M, m, n, $X^1$, $X^2$, $R^1$, and $R^2$ are as defined for the first group of catalysts, $L^1$ is a strongly coordinating neutral electron donor ligand such as any of those described for the first and second group of catalysts, and $L^2$ and $L^3$ are weakly coordinating neutral electron donor ligands in the form of optionally substituted heterocyclic groups. Again, n is zero or 1, such that $L^3$ may or may not be present. Generally, in the third group of catalysts, $L^2$ and $L^3$ are optionally substituted five- or six-membered monocyclic groups containing 1 to 4, preferably 1 to 3, most preferably 1 to 2 heteroatoms, or are optionally substituted bicyclic or polycyclic structures composed of 2 to 5 such five- or six-membered monocyclic groups. If the heterocyclic group is substituted, it should not be substituted on a coordinating heteroatom, and any one cyclic moiety within a heterocyclic group will generally not be substituted with more than 3 substituents.

For the third group of catalysts, examples of $L^2$ and $L^3$ include, without limitation, heterocycles containing nitrogen, sulfur, oxygen, or a mixture thereof.

Examples of nitrogen-containing heterocycles appropriate for $L^2$ and $L^3$ include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole.

Examples of sulfur-containing heterocycles appropriate for $L^2$ and $L^3$ include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

Preferred $L^2$ and $L^3$ ligands are aromatic nitrogen-containing and oxygen-containing heterocycles, and particularly preferred $L^2$ and $L^3$ ligands are monocyclic N-heteroaryl ligands that are optionally substituted with 1 to 3, preferably 1 or 2, substituents. Specific examples of particularly preferred $L^2$ and $L^3$ ligands are pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

In general, any substituents present on $L^2$ and/or $L^3$ are selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, $C_6$-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl), N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to 3 heteroatoms and 1 to 3 substituents as above.

Preferred substituents on $L^2$ and $L^3$ include, without limitation, halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroaralkyl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, and nitro.

Of the foregoing, the most preferred substituents are halo, $C_1$-$C_6$ alkyl, $C_1$-$C_6$ haloalkyl, $C_1$-$C_6$ alkoxy, phenyl, substituted phenyl, formyl, N,N-di($C_1$-$C_6$ alkyl)amino, nitro, and nitrogen heterocycles as described above (including, for example, pyrrolidine, piperidine, piperazine, pyrazine, pyrimidine, pyridine, pyridazine, etc.).

In general, the non-labile ligands comprise one or more linkers that provide attachment to the support. The linkers may be attached to any suitable point of attachment on the ligand and may be directly or indirectly attached to the support or further connected to one or more other ligands. Any of the non-labile ligands described herein, or as may be known in the art, may contain one or more such linkers for attachment to a support. Not all of the non-labile ligands and/or the labile ligands need be attached to the support, or attached through the linkers. To illustrate the numerous possibilities, suitable N-heterocyclic carbenes according to formula (V) containing linkers include:

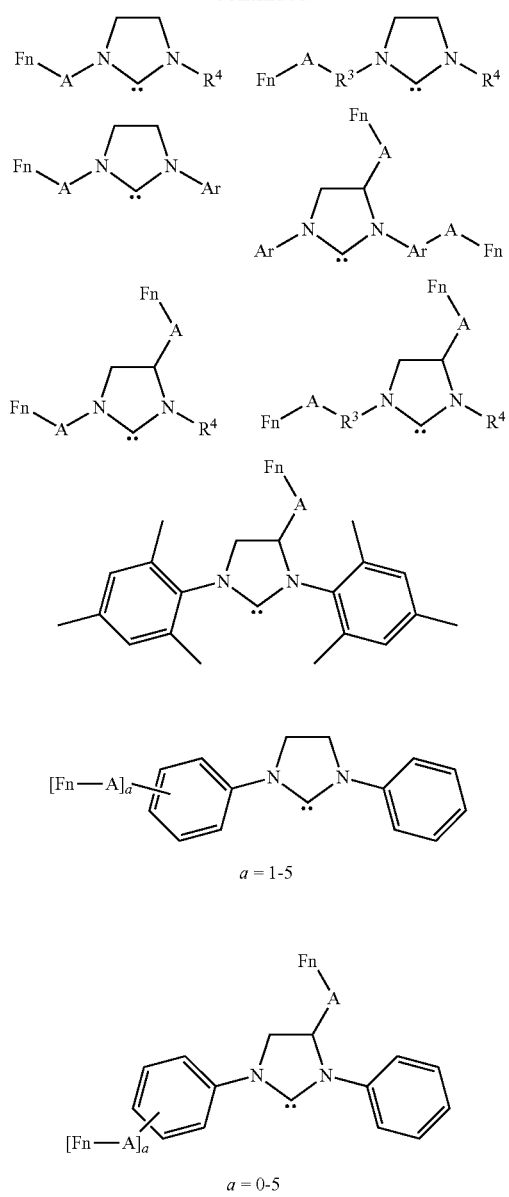

$a = 1\text{-}5$ $a = 0\text{-}5$

More preferred structures for the non-labile ligand used for attachment to the support comprise a functionalized N-heterocyclic carbene ligand according to formula (V) in which one or more of Q, $R^3$, and/or $R^4$ contains a trialkoxysilyl functionalized linker. Non-limiting examples include the following:

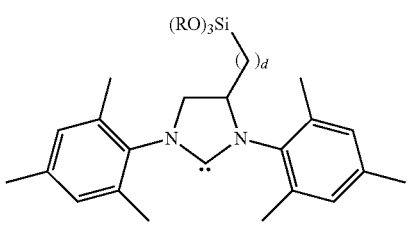

-continued
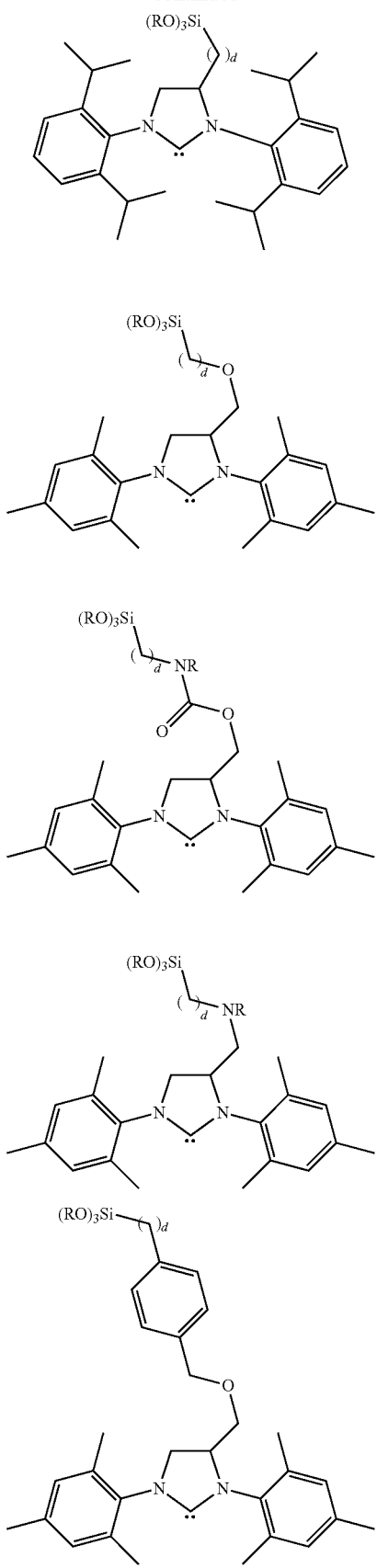
-continued
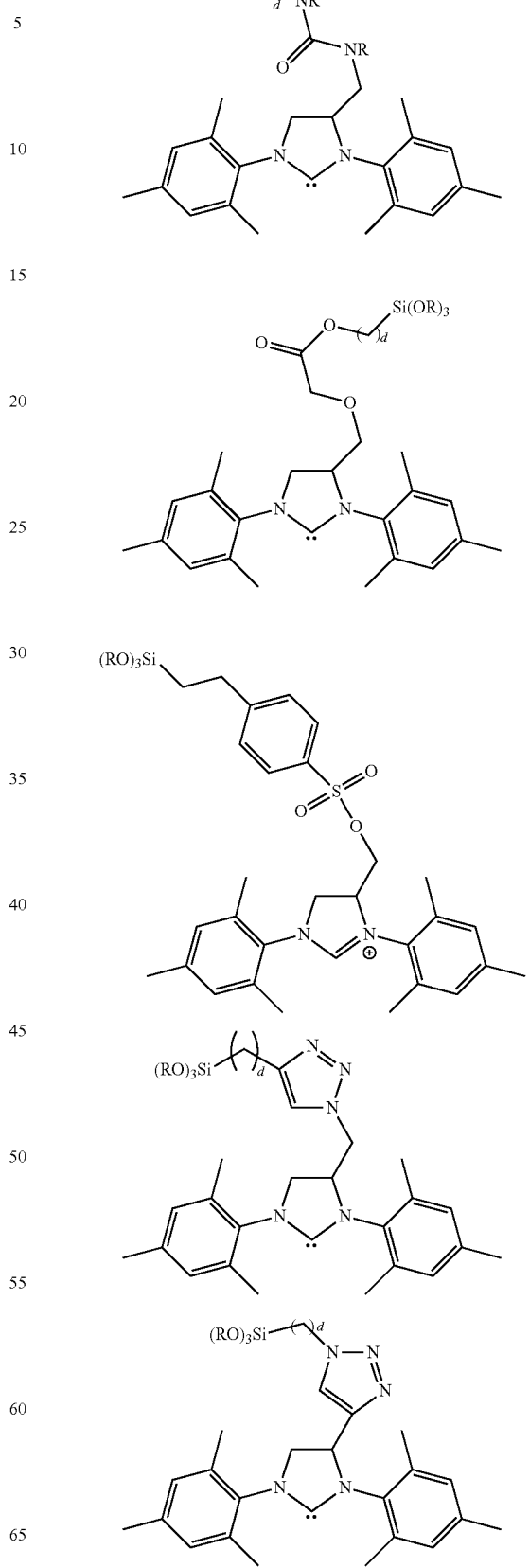

-continued

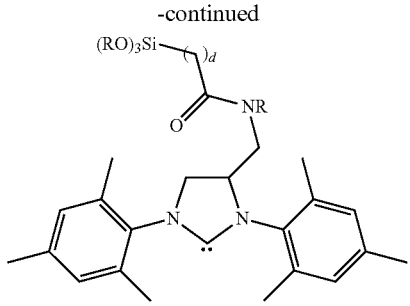

Further illustrative examples of non-labile ligands containing linkers useful in the invention include:

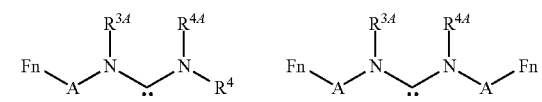
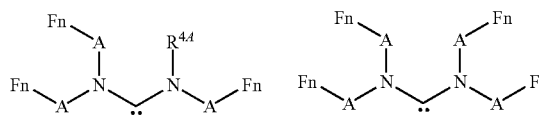
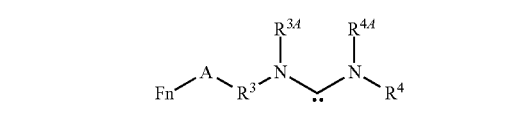
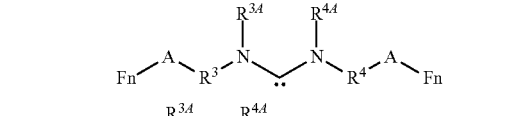
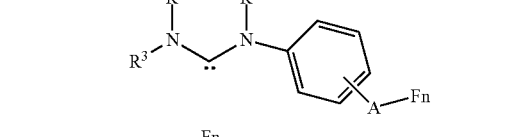
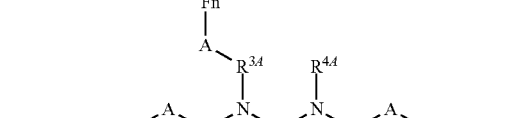
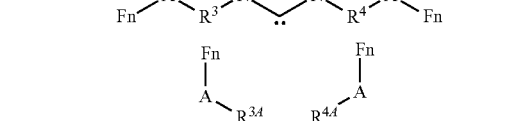
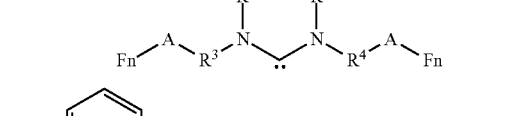
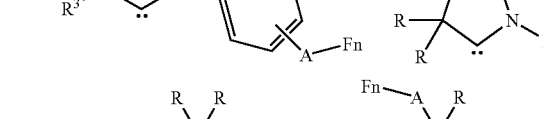

-continued

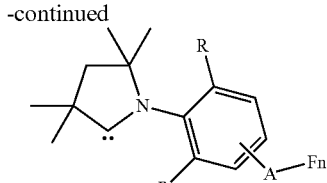
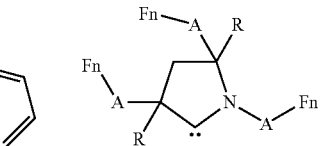
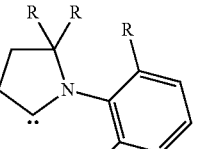
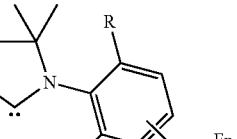
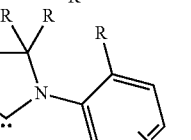
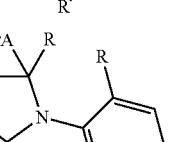
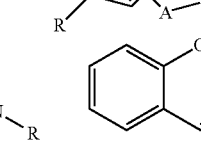
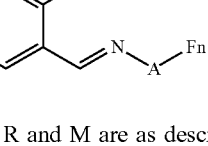
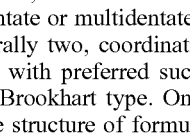

wherein each of A, Fn, R and M are as described above.

In certain embodiments, $L^2$ and $L^3$ may also be taken together to form a bidentate or multidentate ligand containing two or more, generally two, coordinating heteroatoms such as N, O, S, or P, with preferred such ligands being diimine ligands of the Brookhart type. One representative bidentate ligand has the structure of formula (VII)

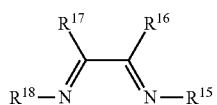

(VII)

wherein $R^{15}$, $R^{16}$, $R^{17}$, and $R^{18}$ hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

In a fourth group of catalysts that have the structure of formula (II), two of the substituents are taken together to form a bidentate ligand or a tridentate ligand. Examples of bidentate ligands include, but are not limited to, bisphosphines, dialkoxides, alkyldiketonates, and aryldiketonates. Specific examples include —P(Ph)$_2$CH$_2$CH$_2$P(Ph)$_2$-, —As(Ph)$_2$CH$_2$CH$_2$As(Ph$_2$)-, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N(CH$_3$)$_2$. Other preferred tridentate ligands are those in which any three of $X^1$, $X^2$, $L^1$, $L^2$, $L^3$, $R^1$, and $R^2$ (e.g., $X^1$, $L^1$, and $L^2$) are taken together to be cyclopentadienyl, indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy or with a phenyl group optionally substituted with halide, $C_1$-$C_6$ alkyl, or $C_1$-$C_6$ alkoxy. More preferably, in compounds of this type, X, $L^1$, and $L^2$ are taken together to be cyclopentadienyl or indenyl, each optionally substituted with vinyl, $C_1$-$C_{10}$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy or with a phenyl group optionally substituted with halide, $C_1$-$C_6$ alkyl or $C_1$-$C_6$ alkoxy. Most preferably, X, $L^1$ and $L^2$ may be taken together to be cyclopentadienyl, optionally substituted with vinyl, hydrogen, methyl, or phenyl. Tetradentate ligands include, but are not limited to O$_2$C(CH$_2$)$_2$P(Ph)(CH$_2$)$_2$P(Ph)(CH$_2$)$_2$CO$_2$, phthalocyanines, and porphyrins.

Complexes wherein Y is coordinated to the metal are examples of the fourth group of catalysts, and are commonly called "Grubbs-Hoveyda" catalysts. Grubbs-Hoveyda metathesis-active metal carbene complexes may be described by the formula

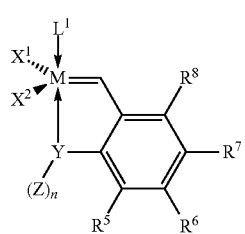

(VIII)

wherein,

M is a Group 8 transition metal, particularly Ru or Os, or, more particularly, Ru;

$X^1$, $X^2$, and $L^1$ are as previously defined herein;

Y is a heteroatom selected from N, O, S, and P; preferably Y is O or N;

$R^5$, $R^6$, $R^7$, and $R^8$ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, borate, or -A-Fn, wherein A and Fn have been defined above; and any combination of $R^5$, $R^6$, $R^7$, and $R^8$ can be linked to form one or more cyclic groups;

n is 1 or 2, such that n is 1 for the divalent heteroatoms O or S, and n is 2 for the trivalent heteroatoms N or P;

Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl; and wherein any combination or combinations of $X^1$, $X^2$, $L^1$, Y, Z, $R^5$, $R^6$, $R^7$, and $R^8$ are linked to a support. In general, Grubbs-Hoveyda complexes useful in the invention contain a chelating alkylidene moiety of the formula

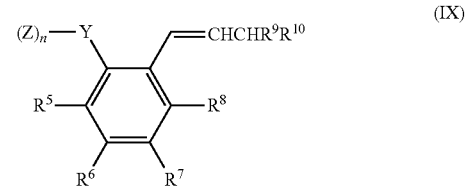

(IX)

wherein Y, n, Z, $R^5$, $R^6$, $R^7$, and $R^8$ are as previously defined herein;

$R^9$ and $R^{10}$ are each, independently, selected from hydrogen or a substitutent group selected from alkyl, aryl, alkoxy, aryloxy, $C_2$-$C_{20}$ alkoxycarbonyl, or $C_1$-$C_{20}$ trialkylsilyl, wherein each of the substituent groups is substituted or unsubstituted; and wherein any combination or combinations of Z, Y, $R^5$, $R^6$, $R^7$, $R^8$, $R^9$, and $R^{19}$ may be linked to a support.

Examples of complexes comprising Grubbs-Hoveyda ligands suitable in the invention include:

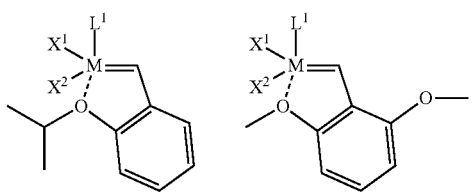

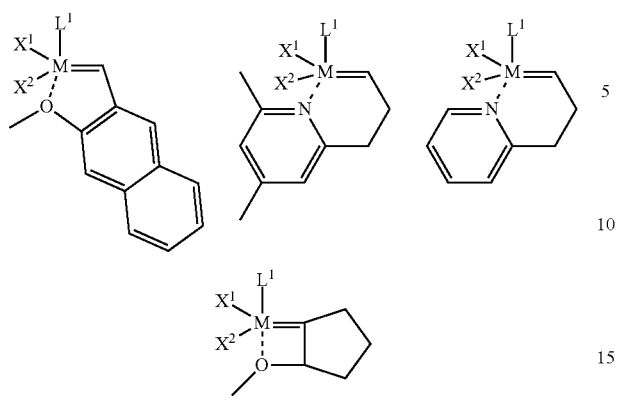

wherein, $L^1$, $X^1$, $X^2$, and M are as described for any of the other groups of catalysts. Suitable chelating carbenes and carbene precursors are further described by Pederson et al. (U.S. Pat. Nos. 7,026,495; 6,620,955) and Hoveyda et al. (U.S. Pat. No. 6,921,735; WO0214376).

The labile ligands generally comprise one or more linkers that provide attachment to the support. The linkers may be attached to any suitable point of attachment on the ligand and may be directly or indirectly attached to the support or further connected to one or more other ligands. Any of the labile ligands described herein, or as may be known in the art, may contain one or more such linkers for attachment to a support. To illustrate the numerous possibilities, suitable chelating carbenes according to formula (IX) containing linkers include:

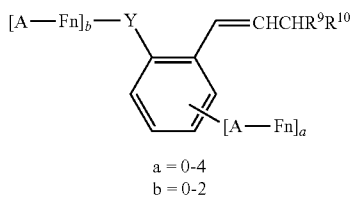

a = 0-4
b = 0-2

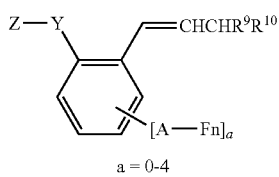

a = 0-4

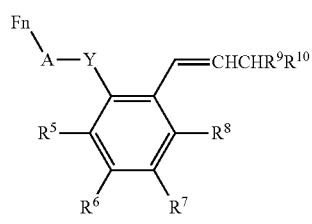

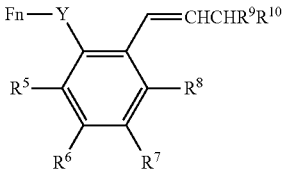

In certain embodiments, and as shown in the above structures, chelating carbene labile ligands may comprise linkers at one or more of the Z, $R^5$, $R^6$, $R^7$, and $R^8$ positions of formula (IX). That is, each of Z, $R^5$, $R^6$, $R^7$, and $R^8$ may be a linker that provides attachment to a support, or may be a substituent (as described above) that is attached to the linker. For convenience, some of the possible linker attachments are referred to herein as "Type I" and "Type II" as follows:

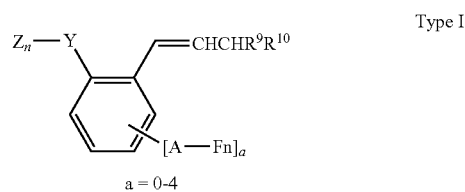

Type I a = 0-4
n = 1 or 2

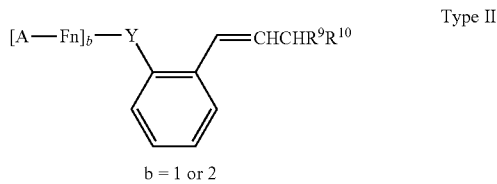

Type II b = 1 or 2

Further suitable examples of Grubbs-Hoveyda ligand complexes (Type I and Type II according to the invention) include:

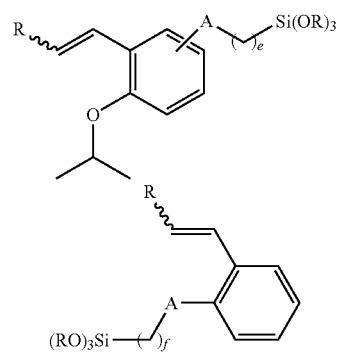

where the R groups correspond to those substituents noted for formula (IX) and the trialkoxysilyl groups described above.

More preferred complexes include structures wherein $L^2$ and $R^2$ according to formulae (II), (IV), or (VI) are linked, such as styrenic compounds that also include a functional group for attachment to the support. Examples in which the functional group is a trialkoxysilyl functionalized moiety include, but are not limited to, the following:

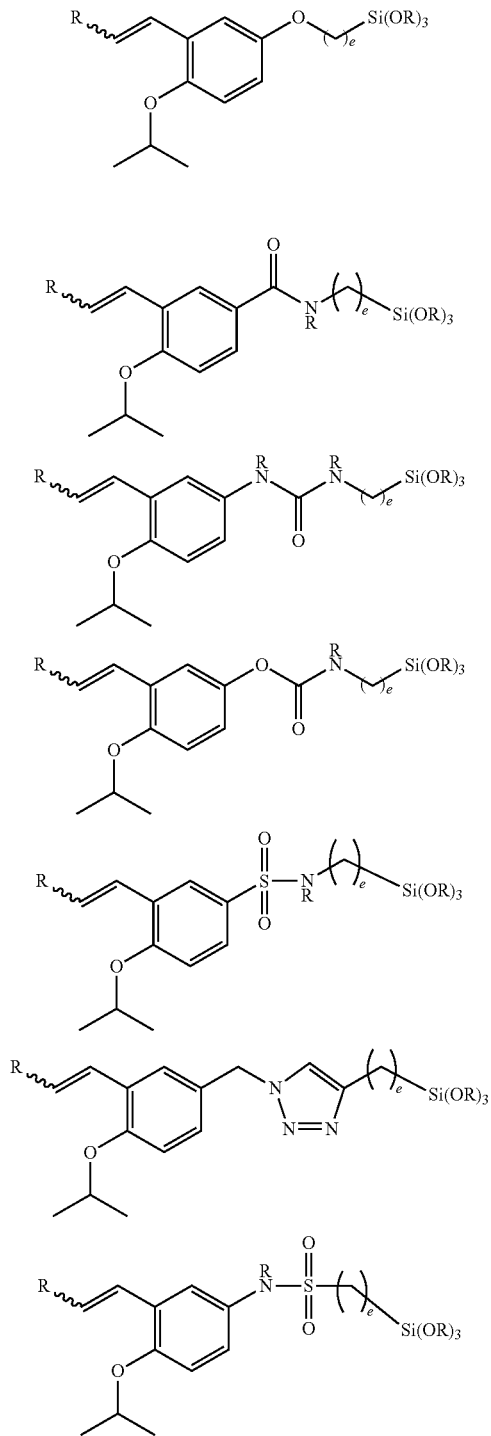
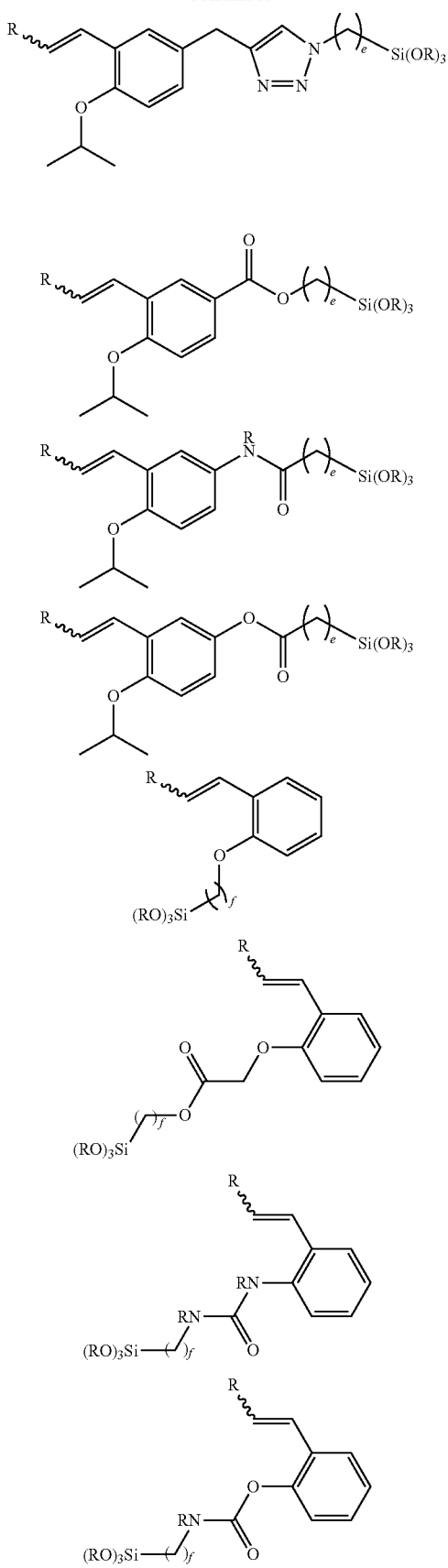

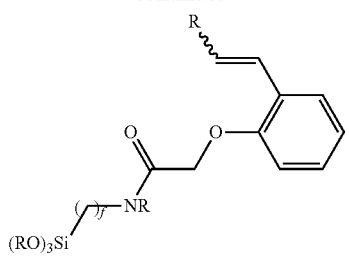

Further examples of complexes having linked ligands include those having linkages between a neutral NHC ligand and an anionic ligand, a neutral NHC ligand and an alkylidine ligand, a neutral NHC ligand and a non-labile L² ligand, a neutral NHC ligand and a non-labile L³ ligand, an anionic ligand and an alkylidine ligand, and any combination thereof. While the possible structures are too numerous to list herein, some suitable structures based on formula (IV) include:

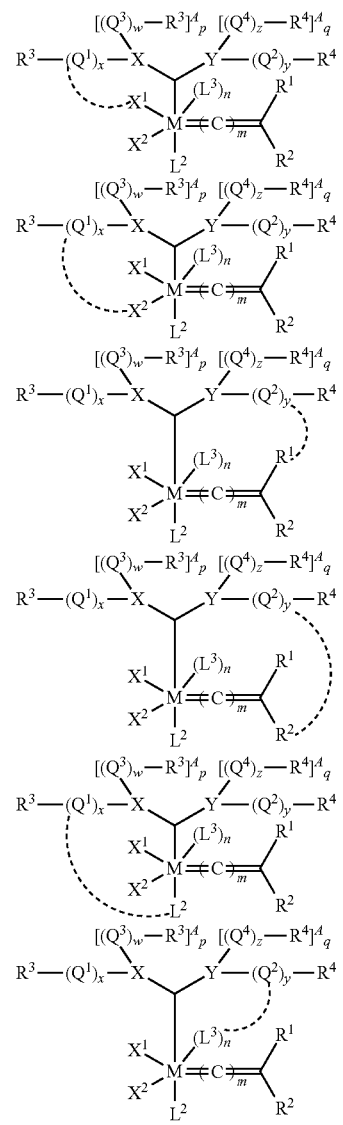

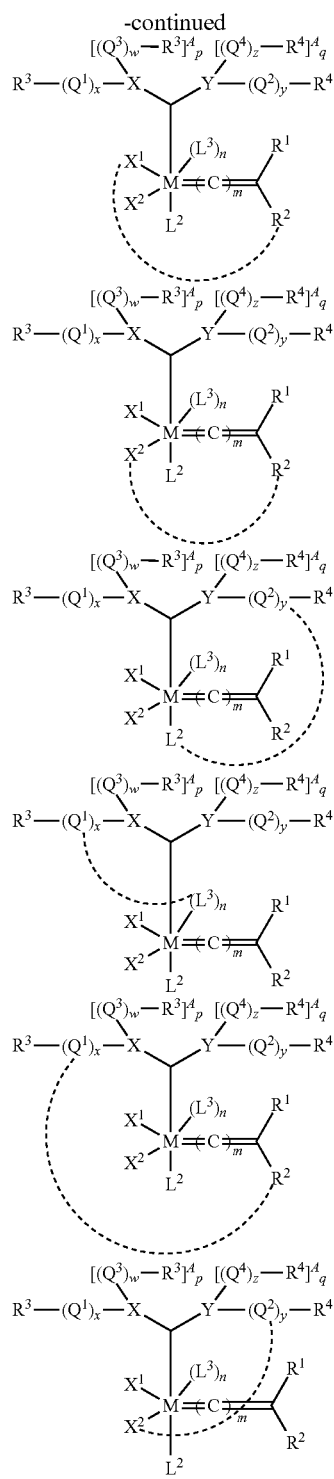

In addition to the catalysts that have the structure of formula (II), as described above, other transition metal carbene complexes include, but are not limited to:

neutral ruthenium or osmium metal carbene complexes containing metal centers that are formally in the +2 oxidation state, have an electron count of 16, are penta-coordinated, and are of the general formula (VIII);

neutral ruthenium or osmium metal carbene complexes containing metal centers that are formally in the +2 oxidation state, have an electron count of 18, are hexa-coordinated, and are of the general formula (IX);

cationic ruthenium or osmium metal carbene complexes containing metal centers that are formally in the +2 oxidation state, have an electron count of 14, are tetra-coordinated, and are of the general formula (X); and cationic ruthenium or osmium metal carbene complexes containing metal centers that are formally in the +2 oxidation state, have an electron count of 14, are penta-coordinated, and are of the general formula (XI)

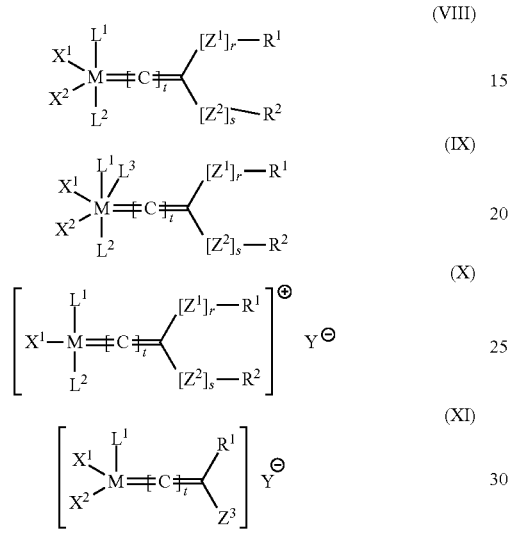

wherein: $X^1$, $X^2$, $L^1$, $L^2$, n, $L^3$, $R^1$, and $R^2$ are as defined for any of the previously defined four groups of catalysts; r and s are independently zero or 1; t is an integer in the range of zero to 5; Y is any non-coordinating anion (e.g., a halide ion, $BF_4^-$, etc.); $Z^1$ and $Z^2$ are independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, and —S(=O)$_2$—; $Z^3$ is any cationic moiety such as —P($R^2$)$_3$' or —N($R^2$)$_3$; and any two or more of $X^1$, $X^2$, $L^1$, $L^2$, $L^3$, n, $Z^1$, $Z^2$, $Z^3$, $R^1$, and $R^2$ may be taken together to form a cyclic group, e.g., a multidentate ligand, and wherein any one or more of $X^1$, $X^2$, $L^1$, $L^2$, n, $L^3$, $Z^1$, $Z^2$, $Z^3$, $R^1$, and $R^2$ may be attached to a support via the linkers.

Non-limiting examples of catalysts that may be used to prepare supported complexes and in the reactions disclosed herein include the following, some of which for convenience are identified throughout this disclosure by reference to their molecular weight:

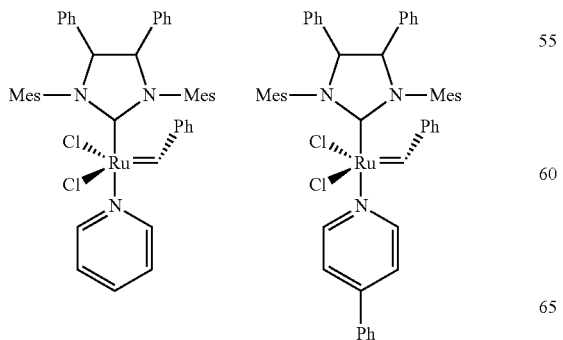

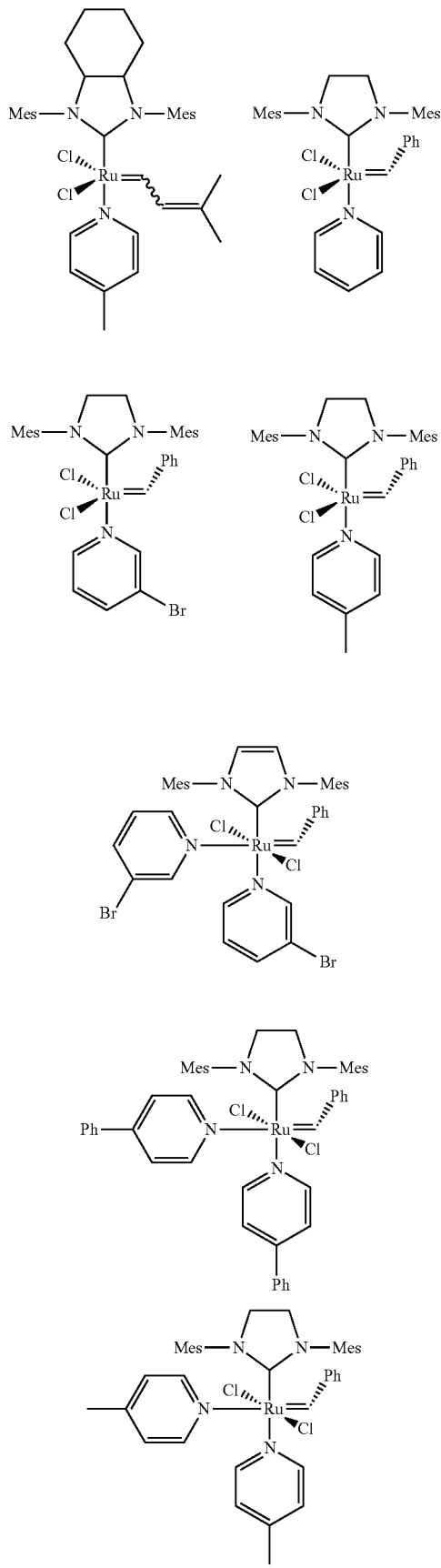

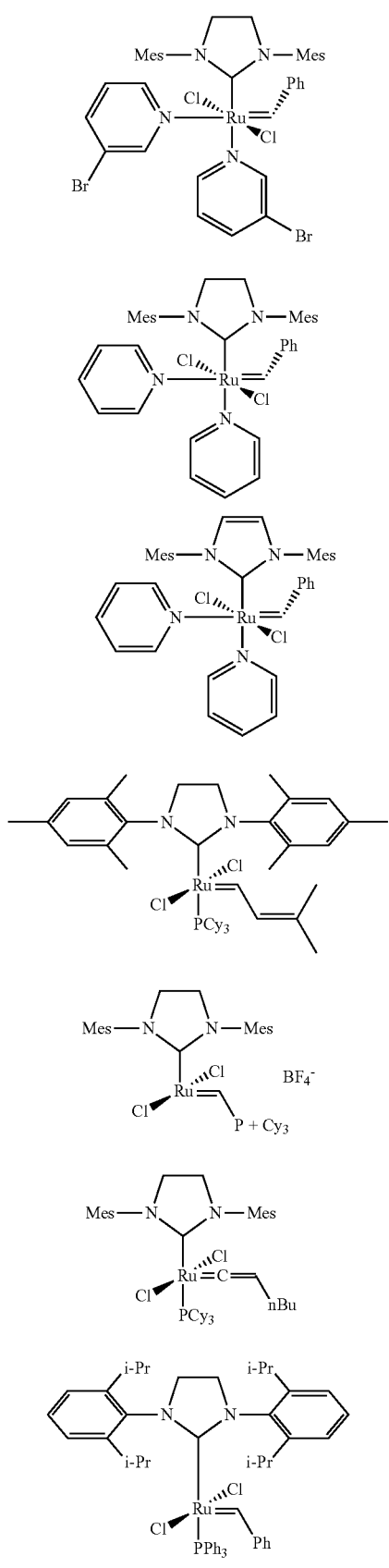
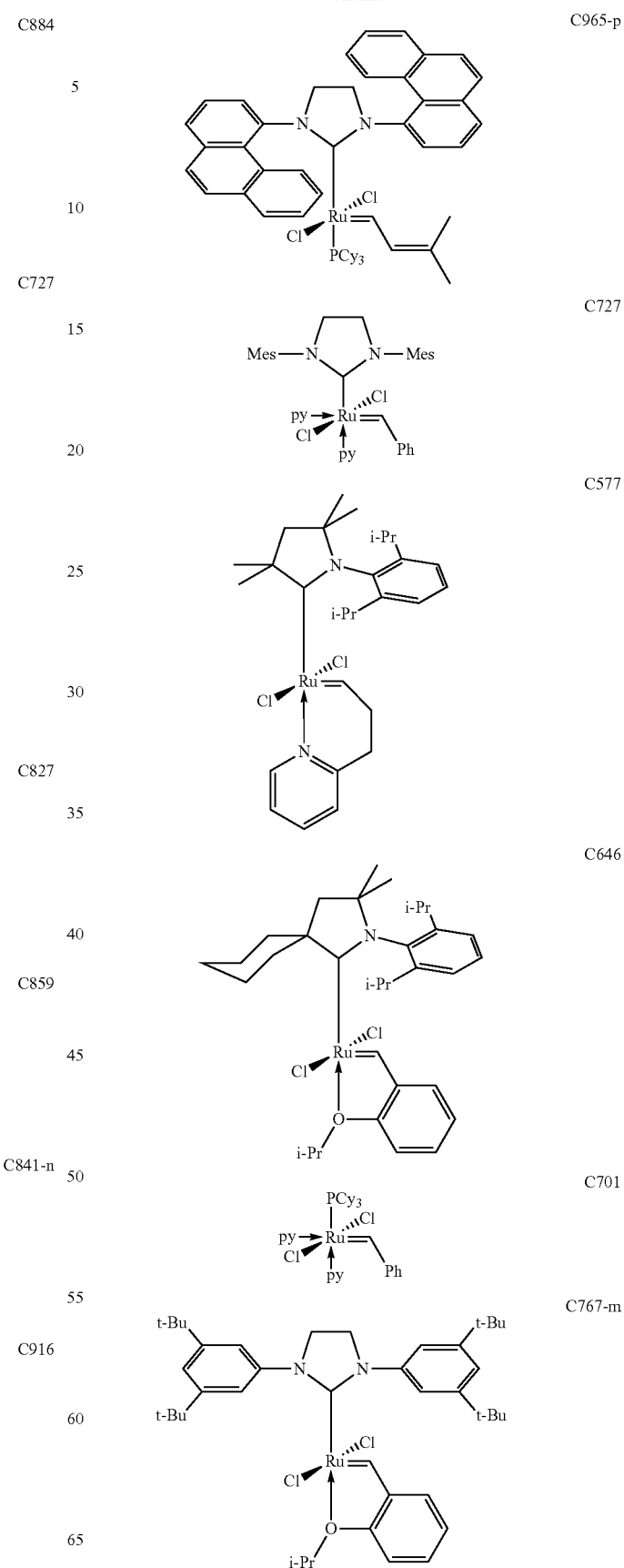

-continued
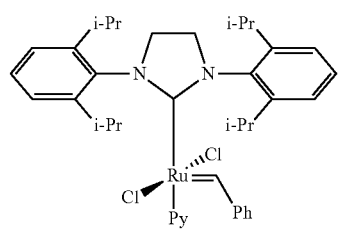
C811
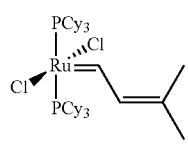
C801
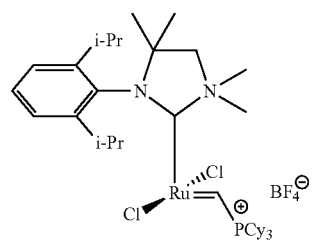
C838
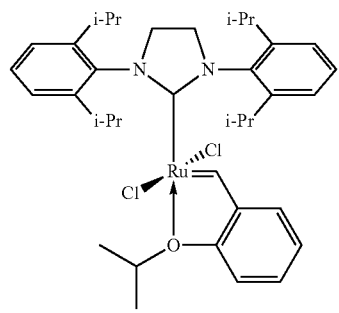
C712
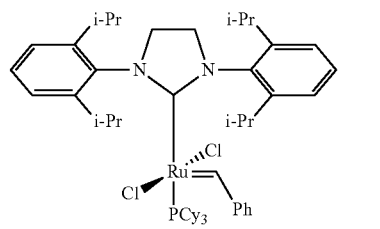
C933
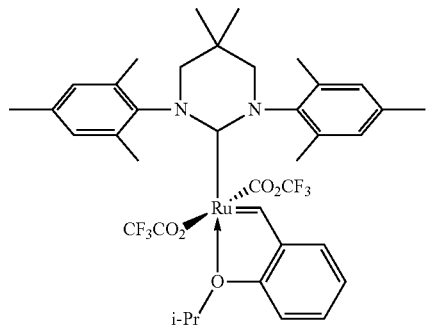
C824
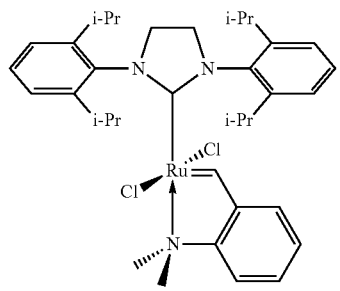
C697 (X = Cl)
C785 (X = Br)
C879 (X = I)
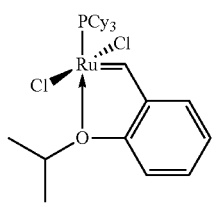
C601
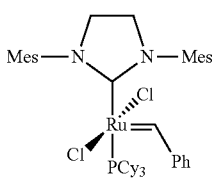
C848
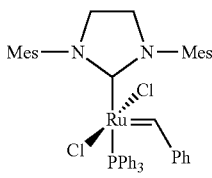
C831
C627
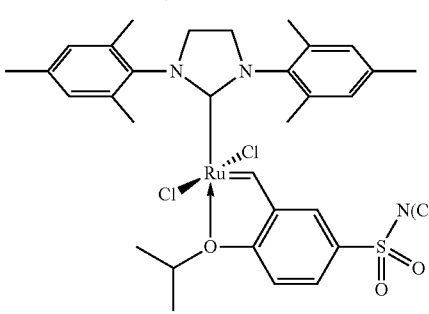

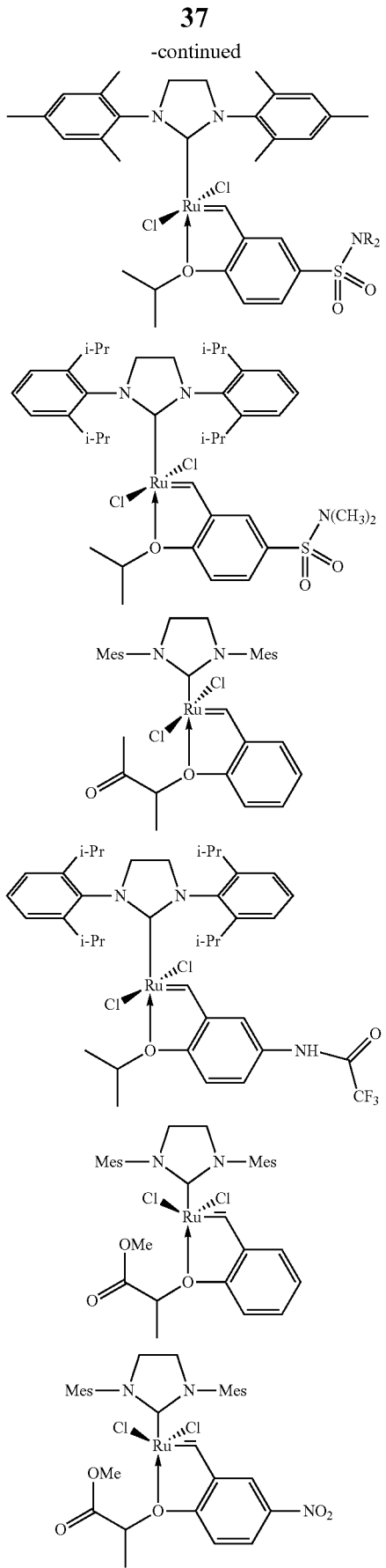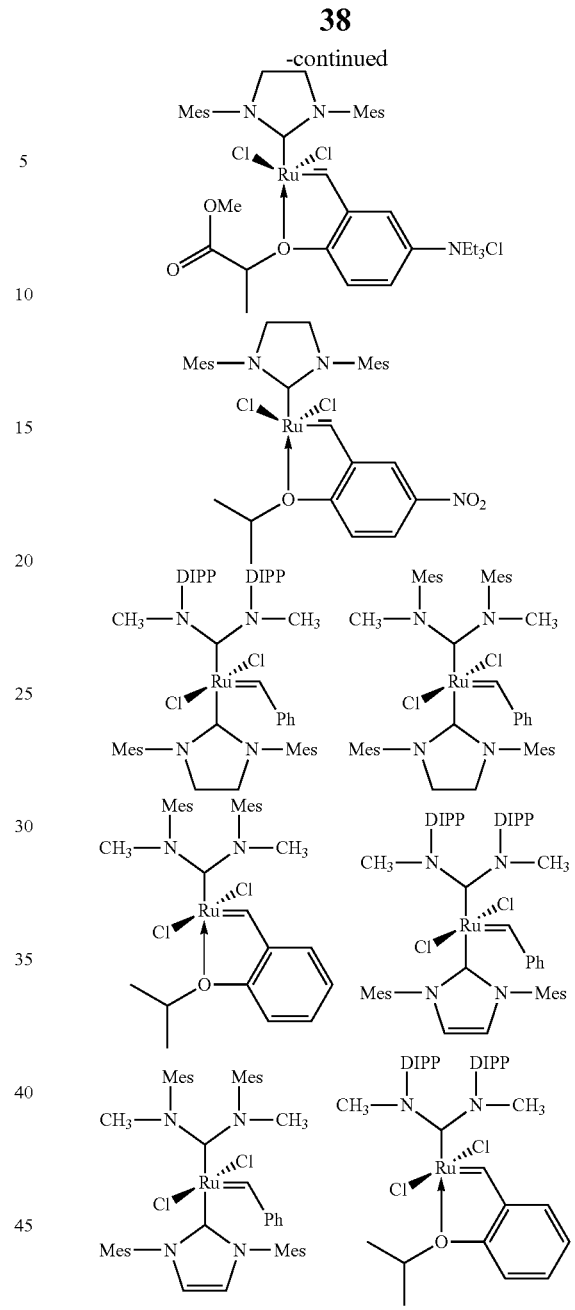

In the foregoing molecular structures and formulae, Ph represents phenyl, Cy represents cyclohexyl, Me represents methyl, nBu represents n-butyl, i-Pr represents isopropyl, py represents pyridine (coordinated through the N atom), Mes represents mesityl (i.e., 2,4,6-trimethylphenyl) and DIPP represents 2,6-diisopropylphenyl.

Further examples of catalysts useful to prepare supported complexes and in the reactions disclosed herein include the following: ruthenium (II) dichloro (3-methyl-1,2-butenylidene) bis(tricyclopentyl-phosphine) (C716); ruthenium (II) dichloro (3-methyl-1,2-butenylidene) bis(tricyclohexyl-phosphine) (C801); ruthenium (II) dichloro(phenylmethylene) bis(tricyclohexylphosphine) (C823); ruthenium (II) [1,3-bis-(2,4,6-trimethylphenyl)-2-imidazolidinylidene] dichloro (phenylmethylene) (triphenylphosphine) (C830), and ruthenium (II) dichloro (vinyl phenylmethylene) bis (tricyclohexylphosphine) (C835); ruthenium (II) dichloro (tricyclohexylphosphine) (o-isopropoxyphenylmethylene) (C601), and ruthenium (II) (1,3-bis-(2, 4, 6,-trimethylphenyl)-2-imidazolidinylidene) dichloro (phenylmethylene) (bis 3-bromopyridine (C884)).

Still further catalysts useful in ring-closing metathesis, ring-opening metathesis polymerization, cross metathesis, ring-opening cross metathesis, self-metathesis, ethenolysis, alkenolysis, acyclic diene metathesis polymerization, and combinations thereof. Are disclosed herein include the following structures:

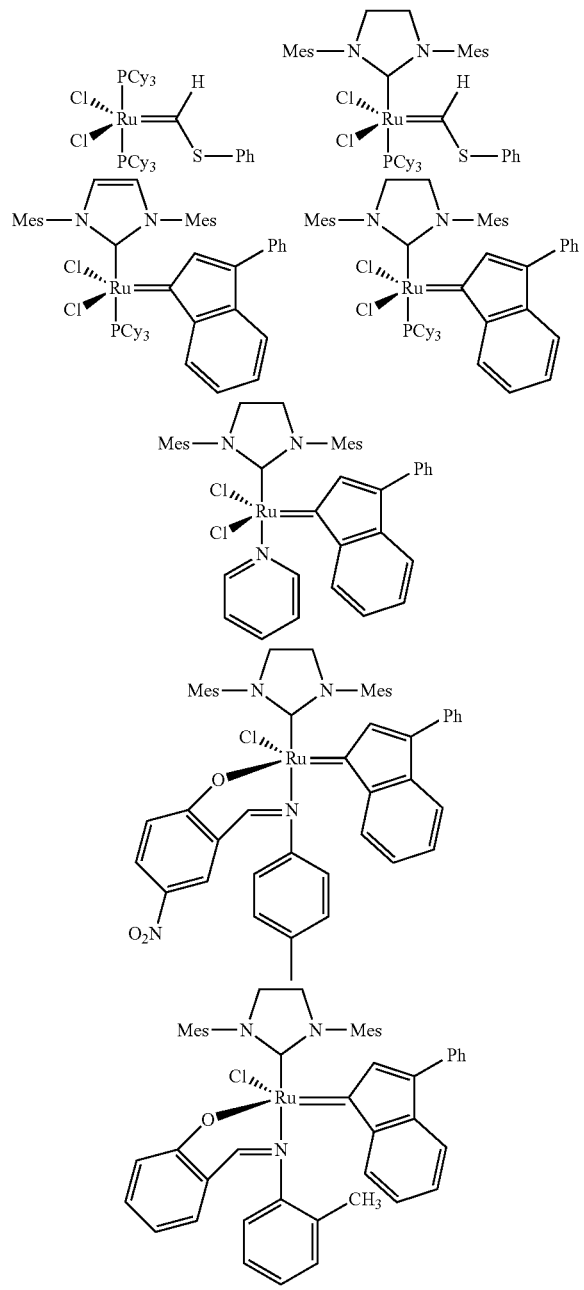

Suitable supports for any of the catalysts described herein may be of synthetic, semi-synthetic, or naturally occurring materials, which may be organic or inorganic, e.g., polymeric, ceramic, or metallic. Attachment to the support will generally, although not necessarily, be covalent, and the covalent linkage may be direct or indirect. Indirect covalent linkages are typically, though not necessarily, through a functional group on a support surface. Ionic attachments are also suitable, including combinations of one or more anionic groups on the metal complexes coupled with supports containing cationic groups, or combinations of one or more cationic groups on the metal complexes coupled with supports containing anionic groups. Another suitable mode of attachment would be via a Lewis acid/Lewis base interaction as described in Huang, Z.; Brookhart, M.; Goldman, A. S.; Kundu, S.; Ray, A.; Scott, S. L.; Vicente, B. C. Adv. Synth. Catal., 351, 188-206 (2009). This type of attachment could include combinations of one or more Lewis basic groups on the metal complexes coupled with supports containing Lewis acid groups, or combinations of one or more Lewis acid groups on the metal complexes coupled with supports containing Lewis basic groups.

In general, the support is selected from silicas, silicates, aluminas, aluminum oxides, silica-aluminas, aluminosilicates, zeolites, titanias, titanium dioxide, magnetite, magnesium oxides, boron oxides, clays, zirconias, zirconium dioxide, carbon, polymers, cellulose, cellulosic polymers amylose, amylosic polymers, or a combination thereof. The support preferably comprises silica, a silicate, or a combination thereof.

In certain embodiments, it is also possible to use a support that has been treated to include functional groups, inert moieties, and/or excess ligands. Any of the functional groups described herein are suitable for incorporation on the support, and may be generally accomplished through techniques known in the art. Inert moieties may also be incorporated on the support to generally reduce the available attachment sites on the support, e.g., in order to control the placement, or amount, of complex linked to the support. Still further, the addition of excess ligand(s) on the support, particularly excess labile ligand(s), is possible, and may help to improve catalyst performance in some cases. In particular embodiments of the invention, excess Hoveyda chelating carbene ligands may be attached to the support.

Methods of Making the Supported Catalyst Complex

The supported complex may be prepared by a number of techniques, and is not generally limited to one particular method. Suitable techniques include:

(a) formation of a functionalized homogeneous complex comprising a non-labile ligand and a labile ligand, wherein each of the ligands comprise linkers for attachment to a support, via direct synthesis, or via ligand exchange reactions in which ligands, or ligand precursors, containing linkers are exchanged for ligands of a homogeneous complex comprising ligands to thereby form a functionalized homogeneous complex, followed by attachment of the complex to a support via the linkers of the non-labile and labile ligands;

(b) formation of a functionalized heterogeneous support comprising a non-labile ligand and a labile ligand, wherein the ligands are attached to the support and the attached ligands comprise linkers for attachment of a homogeneous complex to the support, and contacting a homogeneous complex comprising ligands with the support such that ligands of the complex are exchanged for ligands attached to the support to thereby attach the complex to the support via the linkers of the non-labile and labile ligands;

(c) formation of a functionalized heterogeneous support comprising a non-labile ligand or a labile ligand, wherein the non-labile ligand or the labile ligand is attached to the support and the ligand comprises a linker for attachment of a homogeneous complex to the support, and contacting a homogeneous complex comprising a labile ligand, and optionally a non-labile ligand, with the support, wherein the non-labile and/or labile ligands of the complex comprises a linker for attachment to the support, such that the labile ligands of the complex are exchanged for the ligands attached to the support to thereby attach the complex to the support via the linkers of the non-labile and labile ligands; and d) formation of a functionalized heterogeneous support comprising a non-labile ligand and a labile ligand, wherein the non-labile ligand and the labile ligand are attached to the support and the ligands comprise a linker for attachment of a homogeneous complex to the support, and contacting the support with a Group 8 transition metal or Group 8 transition metal complex to thereby form a Group 8 transition metal catalyst complex directly attached to the support via the linkers of the non-labile and labile ligands.

The supported catalyst complexes can be prepared to include any combination of labile ligand containing linkers, non-labile ligand containing linkers, optionally metal complex containing linkers, and optionally hemi-labile ligand containing linkers, wherein each linker may contain one or more functional groups capable of reacting, or have reacted, with a heterogeneous surface. The supported complexes may be prepared to contain supported ligands and/or supported metal complexes. They may also be prepared by reactions involving homogenous metal complexes, homogenous metal intermediates, and/or homogenous ligand intermediates by ligand exchange reactions, or by traditional organometallic and organic chemical synthesis.

In one particular aspect, the use of ligand exchange reactions provides a suitable means of introducing ligands comprising linkers onto a homogeneous catalyst, or in linking a heterogeneous support comprising non-labile or labile ligands to a homogeneous catalyst. For example, as is more fully detailed in the examples, non-labile and/or labile ligands comprising linkers may be exchanged for non-labile and/or labile linkers on a homogeneous complex, e.g., wherein the complex ligands do not comprise linkers, such that the linker-containing ligand is on the support is exchanged for a complex ligand that does not contain a linker. The introduction of a linker moiety onto the complex through the ligand thereby provides a means for attaching that ligand to the support through the combination of appropriate functional groups on the linker and the support. Similarly, the attachment of linker-containing non-labile and/or labile ligands onto a support allows for the exchange of such ligands with one or both of the non-labile and labile ligands of the homogeneous complex, thereby providing a heterogeneous supported complex in which the complex is attached to the support through the linkers of the non-labile and labile ligands.

In general, the transition metal complexes used as catalysts herein can be prepared by several different methods, such as those described by Schwab et al. (1996) *J. Am. Chem. Soc.* 118:100-110, Scholl et al. (1999) *Org. Lett.* 6:953-956, Sanford et al. (2001) *J. Am. Chem. Soc.* 123: 749-750, U.S. Pat. Nos. 5,312,940 and 5,342,909. Also see U.S. Patent Publication No. 2003/0055262 to Grubbs et al. filed Apr. 16, 2002 for "Group 8 Transition Metal Carbene Complexes as Enantioselective Olefin Metathesis Catalysts", International Patent Publication No. WO 02/079208 application Ser. No. 10/115,581 to Grubbs, Morgan, Benitez, and Louie, filed Apr. 2, 2002, for "One-Pot Synthesis of Group 8 Transition Metal Carbene Complexes Useful as Olefin Metathesis Catalysts," commonly assigned herewith to the California Institute of Technology. Preferred synthetic methods are described in International Patent Publication No. WO 03/11455A1 to Grubbs et al. for "Hexacoordinated Ruthenium or Osmium Metal Carbene Metathesis Catalysts," published Feb. 13, 2003.

Methods of Using the Supported Catalyst Complex

The invention further relates to a method of performing an olefin metathesis reaction using the supported complexes described herein. In general, the method comprises contacting an olefin with the supported catalyst under conditions effective to promote the olefin metathesis reaction. Such metathesis reactions are not specifically limited, and include ring-closing metathesis, ring-opening metathesis polymerization, cross metathesis, ring-opening cross metathesis, self-metathesis, ethenolysis, alkenolysis, acyclic diene metathesis polymerization, and combinations thereof.

The metathesis catalysts that are described infra may be utilized in olefin metathesis reactions according to techniques known in the art. The catalyst is typically added to the reaction medium as a solid, or as a suspension wherein the catalyst is suspended in an appropriate liquid. It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of an olefinic substrate.

The catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate.

In a preferred embodiment, the reactions disclosed herein are carried out under a dry, inert atmosphere. Such an atmosphere may be created using any inert gas, including such gases as nitrogen and argon. The use of an inert atmosphere is optimal in terms of promoting catalyst activity, and reactions performed under an inert atmosphere typically are performed with relatively low catalyst loading. The reactions disclosed herein may also be carried out in an oxygen-containing and/or a water-containing atmosphere, and in one embodiment, the reactions are carried out under ambient conditions. The presence of oxygen or water in the reaction may, however, necessitate the use of higher catalyst loadings as compared with reactions performed under an inert atmosphere. Where the vapor pressure of the reactants allows, the reactions disclosed herein may also be carried out under reduced pressure.

The reactions disclosed herein may be carried out in a solvent, and any solvent that is inert towards cross-metathesis may be employed. Generally, solvents that may be used in the metathesis reactions include organic, protic, or aqueous solvents, such as aromatic hydrocarbons, chlorinated hydrocarbons, ethers, aliphatic hydrocarbons, alcohols, water, or mixtures thereof. Example solvents include benzene, toluene, p-xylene, methylene chloride, 1,2-dichloroethane, dichlorobenzene, chlorobenzene, tetrahydrofuran, diethylether, pentane, methanol, ethanol, water, or mixtures thereof. In a preferred embodiment, the reactions disclosed herein are carried out neat, i.e., without the use of a solvent.

It will be appreciated that the temperature at which a metathesis reaction according to methods disclosed herein is conducted can be adjusted as needed, and may be at least about −78° C., −40° C., −10° C., 0° C., 10° C., 20° C., 25° C., 35° C., 50° C., 70° C., 100° C., or 150° C., or the temperature may be in a range that has any of these values as the upper or lower bounds. In a preferred embodiment, the reactions are carried out at a temperature of at least about 35° C., and in another preferred embodiment, the reactions are carried out at a temperature of at least about 50° C.

The reactions disclosed herein can be conducted in reactors suitable for heterogeneous catalysis. This includes, but is not limited to, continuous flow fixed bed reactors, fluidized bed reactors, and catalytic distillation reactors.

Metathesis products derived from the methods disclosed herein and using the supported complexes of the invention are useful in a variety of areas, including, among others, pharmaceuticals, materials, and industrial and fine chemicals.

It is to be understood that while the invention has been described in conjunction with specific embodiments thereof, that the description above as well as the examples that follow are intended to illustrate and not limit the scope of the invention. Other aspects, advantages, and modifications within the scope of the invention will be apparent to those skilled in the art to which the invention pertains.

EXPERIMENTAL

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

The following examples are to be considered as not being limiting of the invention as described herein, and are instead provided as representative examples of the supported catalysts of the invention and the methods that may be used in their preparation.

EXAMPLES

Materials and Methods

All glassware was oven dried and reactions were performed under an atmosphere of argon using standard Schlenk techniques or in an mBraun glovebox unless otherwise noted. All organic solvents were purchased from Aldrich and used as received. Silica gel employed for grafting of Ru-complexes was Merck® Grade 60 (70-230 mesh, 60 Å, 550 m$^2$/g) which was dried under vacuum at >200° C. for 72 h. All commercial chemicals were purchased from commercial suppliers and used as received unless otherwise noted.

Synthesis of Supported Catalyst Complexes

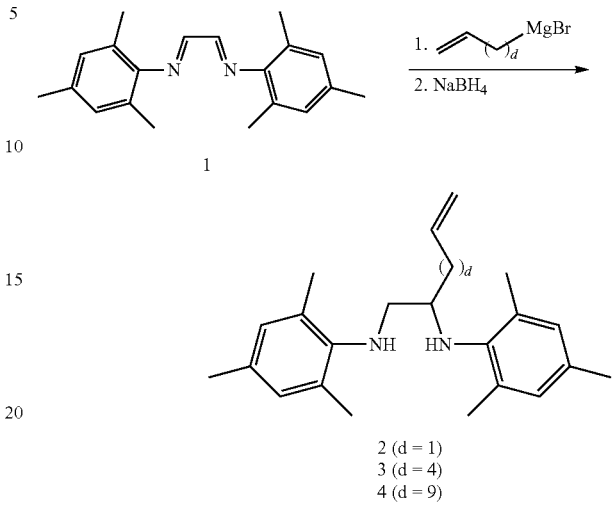

2 (d = 1)
3 (d = 4)
4 (d = 9)

Syntheses of Diamines 2-4:

Synthesis of Diamine 2:

In an oven dried 500 ml round bottomed flask (rbf) with stirbar, under an argon atmosphere, 1 (obtained by procedures described in Grasa, G. A. et al., *J. Org. Chem.*, 66, 7729-7737 (2001); 1.00 g, 3.45 mmol) was added and dissolved in 100 ml of THF. This solution was cooled to −78° C. using a dry ice/acetone bath and then allyl magnesiumbromide (4.5 ml, 0.77 M in diethylether, 3.5 mmol) was added dropwise via syringe. After the addition, the cold bath was removed and the mixture stirred for 1 hour while warming to room temperature. Then the reaction was further diluted by the addition of methanol (80 ml) and finally an excess of sodium borohydride (0.80 g, 21.2 mmol) was added in 2 portions (half at beginning and 2$^{nd}$ portion 30 min later) and the mixture stirred for a total of 2.5 hours. Then the reaction was quenched by the addition of a saturated NH$_4$Cl solution until bubbling ceased. This mixture was added to a separatory funnel and the organic layer separated. The aqueous layer was extracted with hexanes (3×75 ml) and the combined organic extracts were washed with water, brine and dried over MgSO$_4$ and finally concentrated to give a light yellow oil. The crude material was purified via column chromatography using hexanes:ethyl acetate (30:1) to yield 1.017 g (88% yield) of 2 as a faint yellow oil. $^1$H NMR (C$_6$D$_6$, 300 MHz): δ=6.81 (s, 2H), 6.79 (s, 2H), 5.71-5.57 (m, 1H), 4.98-4.92 (m, 2H), 3.57-3.49 (m, 1H), 3.34-3.16 (broad s, 2H, NH), 3.17 (dd, 1H), 2.71 (dd, 1H), 2.24-2.18 (m, 18H), 2.06-1.90 (m, 2H). $^{13}$C NMR (75 MHz, CD$_2$Cl$_2$): δ=144.3, 142.3, 136.0, 131.7, 131.2, 130.3, 130.2, 129.9, 129.6, 117.7, 57.5, 53.0, 38.7, 20.9, 19.6, 18.8.

Diamine 3: obtained 2.145 g (47% yield) starting from 1 (3.54 g, 12.1 mmol). $^1$H NMR (CDCl$_3$, 400 MHz): δ=6.81 (s, 2H), 6.80 (s, 2H), 5.81-5.70 (m, 1H), 4.99-4.91 (m, 2H), 3.48-3.40 (m, 1H), 3.40-3.00 (broad s, 2H, NH), 3.18 (dd, 1H), 2.75 (dd, 1H), 2.26-2.20 (m, 18H), 2.01 (m, 2H), 1.47 (m, 2H), 1.36 (m, 4H).

Diamine 4: obtained 1.823 g (44% yield) starting from 1 (2.70 g, 9.23 mmol).

Syntheses of NHC Salts 5-7:

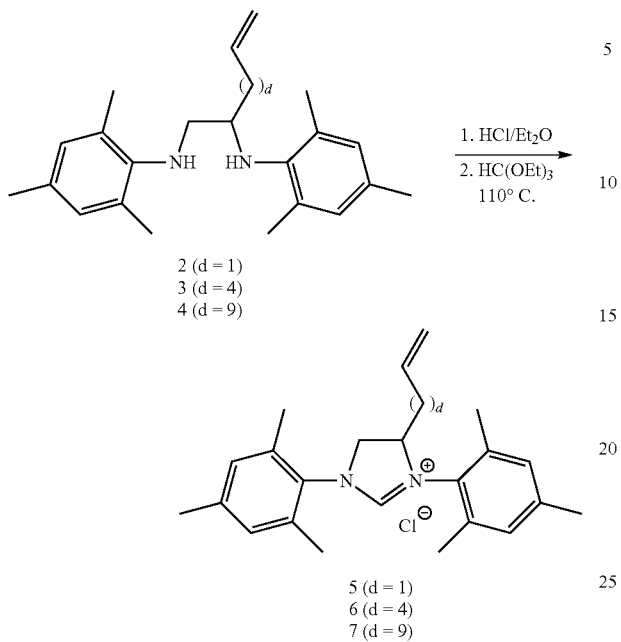

2 (d = 1)
3 (d = 4)
4 (d = 9)

5 (d = 1)
6 (d = 4)
7 (d = 9)

Synthesis of NHC Salt 5:

In an oven dried 100 ml round-bottom flask with stir bar, under an argon atmosphere, diamine 2 (1.55 g, 4.61 mmol) was dissolved in 25 ml of $Et_2O$ and cooled to 0° C. This was treated with a solution of HCl (2 M in $Et_2O$, 2.75 ml) to precipitate the diamine hydrochloride salt. The solid was isolated by filtration and washed with copious amounts of $Et_2O$ and then placed back into the round-bottom flask and quickly dried under vacuum. Then triethylorthoformate (10 ml) was added via syringe and an oven dried reflux condenser was placed on the round-bottom flask against an argon flow. The mixture was heated to 110° C. for 16 hours. Then the mixture was cooled and the volatiles removed under vacuum. The brown residue was then triturated with $Et_2O$ (2×20 ml) and the solvent decanted off each time. A final $Et_2O$ wash was then filtered and the solid washed with Ethyl acetate (10 ml), $Et_2O$ (10 ml) and finally pentane (10 ml) and then dried under vacuum to yield 1.41 g (80% yield over 2 steps) of 5 as an off-white solid. $^1H$ NMR ($CD_2Cl_2$, 300 MHz): δ=10.58 (s, 1H), 7.04 (s, 4H), 5.70-5.56 (m, 1H), 5.24-5.18 (m, 2H), 4.88-4.77 (m, 1H), 4.46 (t, J=11.7 Hz, 1H), 3.97 (dd, J=12 Hz, 8.2 Hz, 1H), 2.66-2.48 (m, 2H), 2.46-2.34 (m, 18H). $^{13}C$ NMR (75 MHz, $CD_2Cl_2$): δ=161.4, 140.8, 140.6, 136.4, 135.6, 131.3, 130.9, 130.6, 130.4, 130.3, 129.5, 120.4, 63.2, 56.2, 37.3, 21.3, 19.3, 18.8.

NHC salt 6: obtained 2.096 g (88% yield over 2 steps) starting from 3 (2.145 g, 5.67 mmol). $^1H$ NMR ($CD_2Cl_2$, 400 MHz): δ=10.60 (s, 1H), 7.05-7.03 (4H), 5.78-5.68 (m, 1H), 4.98-4.91 (m, 2H), 4.53-4.62 (m, 1H), 4.47 (t, 1H), 3.89 (dd, 1H), 2.44-2.33 (m, 18H), 2.04-1.96 (m, 2H), 1.80-1.60 (m, 4H), 1.42-1.34 (m, 2H).

NHC salt 7: obtained 1.24 g (62% yield) starting from 4 (1.823 g, 4.04 mmol). Note: purification of this NHC salt was more difficult due to the longer $C_{11}$ tail and was accomplished by trituration with $Et_2O$ (2×10 ml) and the solvent decanted off each time. A final $Et_2O$ wash was then filtered and the solid washed with pentane (2×10 ml) and then dried under vacuum. The obtained solid was stickier than the $C_3$ and $C_6$ analogues.

Syntheses of NHC Salts 8-10:

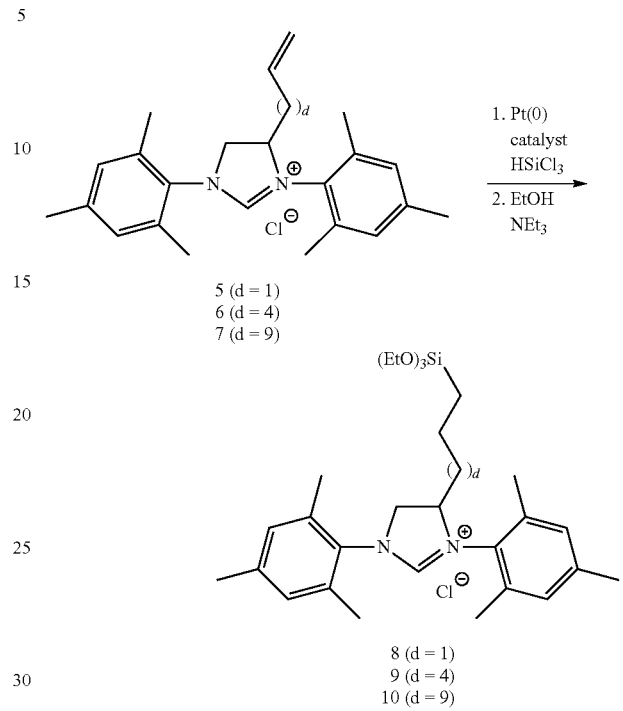

5 (d = 1)
6 (d = 4)
7 (d = 9)

8 (d = 1)
9 (d = 4)
10 (d = 9)

Synthesis of NHC salt 8:

In an oven dried 25 ml round-bottom flask with stir bar, under an argon atmosphere, 5 (500 mg, 1.31 mmol) was added and dissolved in 10 ml of $CH_2Cl_2$. Then $HSiCl_3$ (5 ml, 6.7 g, 50 mmol) was added via syringe. Finally, Pt(0)-1,3-divinyl-1,1,3,3-tetramethyldisiloxane complex solution (500 μA of a 0.10 M solution in xylenes, 0.050 mmol, 3.8 mol %) was added via micro-syringe. An oven dried reflux condensor was attached, against an argon flow and the mixture was stirred at reflux for 20 h. Then the reaction mixture was cooled to room temperature and the volatiles removed under vacuum and collected in a secondary cold trap. This step is necessary to remove the excess $HSiCl_3$. The residue was then dissolved in 10 ml of $CH_2Cl_2$ and cooled to 0° C. at which time 10 ml of a 1/1 solution of ethanol/$NEt_3$ was added drop-wise via syringe. A white cloudy precipitate was evident upon addition and gradually disappeared. The reaction was warmed to room temperature with stirring over a period of 2 hours at which time the volatiles were removed under vacuum. The crude residue was purified by column chromatography using 10% ethanol in $CH_2Cl_2$ to obtain 528 mg (74% yield) of 8 as an off-white sticky solid. $^1H$ NMR ($CD_2Cl_2$, 300 MHz): δ=10.58 (s, 1H), 7.01 (s, 4H), 4.74-4.61 (m, 1H), 4.47 (t, J=11.4 Hz, 1H), 3.87 (dd, J=11.6 Hz, 9.1 Hz, 1H), 3.71 (q, J=7 Hz, 6H), 2.41-2.32 (m, 18H), 1.83-1.76 (m, 2H), 1.44-1.30 (m, 2H), 1.14 (t, J=7 Hz, 9H), 0.57 (t, J=8 Hz, 2H). $^{13}C$ NMR (75 MHz, $CD_2Cl_2$): δ=158.9, 138.7, 138.5, 134.7, 133.7, 133.5, 133.4, 129.1, 128.7, 128.6, 128.4, 127.8, 64.0, 58.7, 57.0, 36.5, 22.2, 22.1, 20.7, 20.3, 19.6, 19.5, 19.2, 11.7.

NHC salt 9: obtained 0.724 g (74% yield) starting from 6 (0.71 g, 1.7 mmol); Pt(0)-catalyst (3.3 mol %).

NHC salt 10: obtained 0.561 g (71% yield) starting from 7 (0.59 g, 1.7 mmol); Pt(0)-catalyst (3.3 mol %).

Syntheses of Ru-Complexes 11-13:

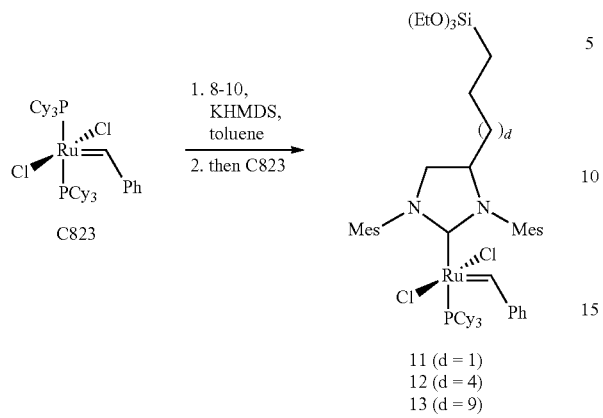

11 (d = 1)
12 (d = 4)
13 (d = 9)

Synthesis of Ru-Complex 11:

In the glove box, an oven dried 100 mL round-bottom flask with a stir bar was charged with 8 (0.60 g 1.1 mmol) and anhydrous toluene (10 mL). While stirring, potassium bis(trimethylsilyl)amide (0.28 g, 1.3 mmol) was added as a solid and the reaction was stirred for 20 minutes. The solution of carbene was then filtered through a celite plug. The celite plug was washed with toluene (5 mL) and the yellow filtrate was transferred into a new, oven dried 100 mL round-bottom flask with a stir bar. Following the solid addition of C823 (0.75 g, 0.91 mmol), the reaction was stirred for 3.5 hours at ambient temperature. Upon completion, the volatiles were removed under reduced pressure and the crude residue was purified by column chromatography using 9/1 hexane/Ethyl acetate to yield 659 mg (70% yield) of 11 as a dark red sticky solid, which was then lyophilized with $C_6D_6$ to give a red powder.

Ru-complex 12: obtained 0.228 g (54% yield) starting from 9 (0.26 g, 0.44 mmol); C823 (0.30 g, 0.37 mmol).

Ru-complex 13: obtained 0.574 g (68% yield) starting from 10 (0.56 g, 0.85 mmol); C823 (0.60 g, 0.73 mmol).

Syntheses of Styrene Ligands 14-16:

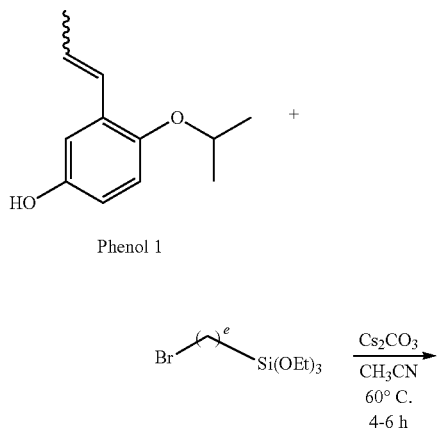

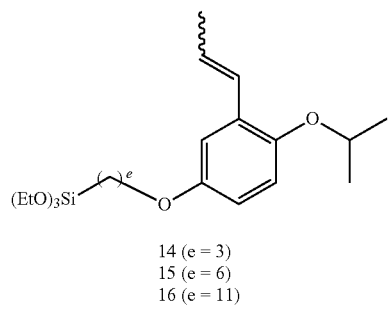

14 (e = 3)
15 (e = 6)
16 (e = 11)

Synthesis of Styrene Ligand 14:

In an oven dried 100 ml rbf with stirbar, under an argon atmosphere, Phenol 1 (obtained from similar procedures described in Yao, Q., *Angew. Chem. Int. Ed.*, 39, 3896-3898 (2000); 96. mg, 0.50 mmol) was added and dissolved in 10 ml of $CH_3CN$. Then solid $Cs_2CO_3$ (250 mg, 0.77 mmol) was added and finally 3-bromopropyl triethoxysilane (240 mg, 0.84 mmol) was added drop-wise via micro-syringe. After the addition, the reaction mixture was stirred at 60° C. for 4 hours. At this time, the mixture was cooled to room temperature and then the volatiles removed under reduced pressure. The crude residue was then triturated with 10 mL of hexanes and filtered. The filter cake was washed with an additional 10 mL of hexanes and then the filtrate was concentrated under reduced pressure to yield a slight yellow oil. The crude material was purified via column chromatography using hexanes:ethyl acetate (20:1) to yield 106 mg (53% yield) of 14 as a colorless oil.

Styrene ligand 15: obtained 0.786 g (54% yield) starting from Phenol 1 (0.63 g, 3.3 mmol); 6-bromohexyl triethoxysilane (1.2 g, 3.6 mmol).

Styrene ligand 16: obtained 0.420 g (40% yield) starting from Phenol 1 (0.40 g, 2.1 mmol); 11-bromoundecyl triethoxysilane (0.83 g, 2.1 mmol).

Syntheses of Ru-Complexes 17-25:

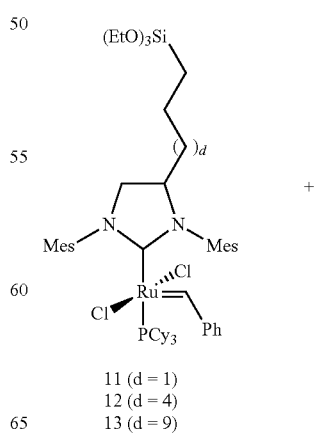

11 (d = 1)
12 (d = 4)
13 (d = 9)

49

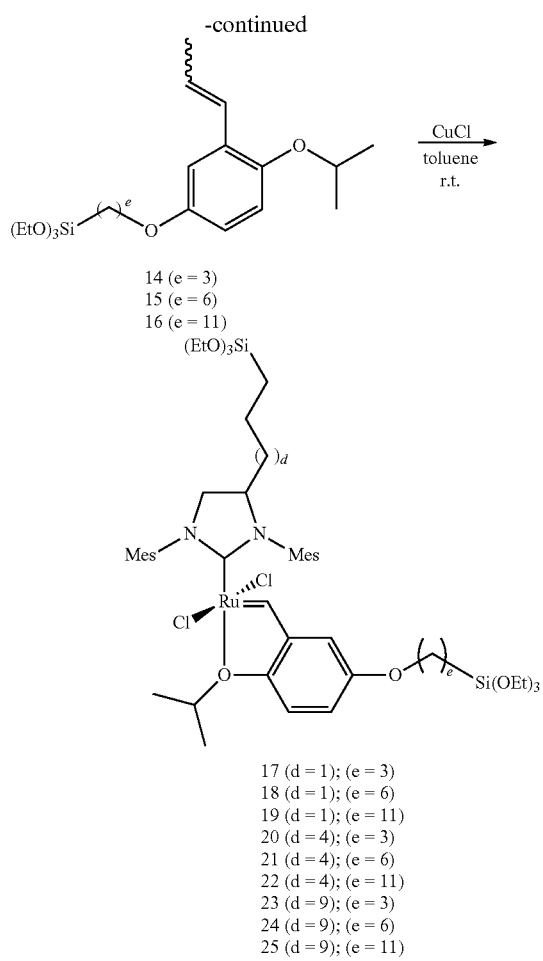

14 (e = 3)
15 (e = 6)
16 (e = 11)

17 (d = 1); (e = 3)
18 (d = 1); (e = 6)
19 (d = 1); (e = 11)
20 (d = 4); (e = 3)
21 (d = 4); (e = 6)
22 (d = 4); (e = 11)
23 (d = 9); (e = 3)
24 (d = 9); (e = 6)
25 (d = 9); (e = 11)

Synthesis of Ru-Complex 17:

In the glove box, an oven dried 100 mL round-bottom flask with a stir bar was charged with 11 (83 mg, 0.079 mmol). Then, styrene ligand 14 (100 mg, 0.25 mmol) was added as a solution in anhydrous toluene (10 mL). The flask was sealed with a septum and then removed from the glovebox and stirred at ambient temperature for 1 hour. Then, solid CuCl (10 mg, 0.10 mmol) was added and the mixture stirred for an additional 16 hours. [Note: for Ru-complexes 17-25, TLC monitoring allows for easy analysis of the reaction conversion. Typical reaction times range from 4-6 hours but longer reaction times (16 hours) are acceptable]. Upon completion, the volatiles were removed under reduced pressure and the crude residue was purified by column chromatography using 6:1 hexanes:ethyl acetate and collecting the green band. This yielded 80 mg (96% yield) of 17 as a green sticky solid.

50

Syntheses of Solid-Supported Ru-Complexes 17-25:

Inside the dry box, silica gel was weighed into a vial containing a stir bar. Then the Ru-complex (17-25) was added to the vial containing the silica gel as a toluene solution (Note: enough toluene used to provide an adequate slurry, typically 10-15 mL and the amount of silica gel employed was based on 0.02 mmol Ru/gram silica gel). The vial was capped and the mixture was stirred at room temperature for 3-5 days. At this stage, the mixture was filtered and collected in a fritted disc extraction thimble and then the thimble containing the silica-supported catalyst was removed from the glove box in a sealed flask and finally placed into an oven dried soxhlet extraction apparatus that was under an argon atmosphere and contained a still pot of $CH_2Cl_2$. The silica-supported catalyst was continuously extracted with $CH_2Cl_2$ for 48-72 hours. Then the extraction thimble containing the solid catalyst was removed from the apparatus and dried under vacuum for 8-24 hours, yielding the pale green silica-supported Ru-complexes 17-25 which are represented in FIG. 1.

Syntheses of Styrene Ligands 26-28:

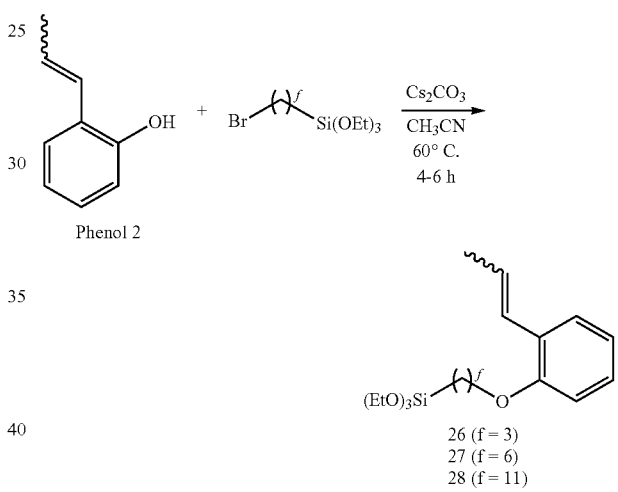

Phenol 2

26 (f = 3)
27 (f = 6)
28 (f = 11)

Synthesis of Styrene Ligand 26:

In an oven dried 100 ml round-bottom flask with a stir bar, under an argon atmosphere, Phenol 2 (0.644 g, 4.80 mmol) was added and dissolved in 10 ml of $CH_3CN$. Then solid $Cs_2CO_3$ (2.35 g, 7.20 mmol) was added and finally 3-bromopropyl triethoxysilane (1.37 g, 4.80 mmol) was added via micro-syringe. After the addition, the reaction mixture was stirred at 60° C. for 4 hours. At this time, the mixture was cooled to room temperature and then the volatiles removed under reduced pressure. The crude residue was then triturated with 10 mL of hexanes and filtered. The filter cake was washed with an additional 10 mL of hexanes and then the filtrate was concentrated under reduced pressure to yield a

TABLE 1

Yield results for the syntheses of Ru-complexes 18-25

| Catalyst | 18 | 19 | 20 | 21 | 22 | 23 | 24 | 25 |
|---|---|---|---|---|---|---|---|---|
| (d + 2, e)[a] | (3, 6) | (3, 11) | (6, 3) | (6, 6) | (6, 11) | (11, 3) | (11, 6) | (11, 11) |
| Yield | 64% | 79% | 53% | 62% | 59% | 71% | 29%[b] | 51% |

[a]this notation gives the actual number of carbon atoms in the linkers of the dual supported catalysts.
[b]this yield was obtained over 2 steps, starting from NHC salt 9 and C823 without prior isolation of 12 before the addition of 15 and CuCl. Isolation and purification was as described above.

slight yellow oil. The crude material was purified via column chromatography using hexanes:ethyl acetate (12:1) to yield 506 mg (31% yield) of 26 as a colorless oil.

Styrene ligand 27: obtained 1.05 g (58% yield) starting from Phenol 2 (0.644 g, 4.80 mmol); 6-bromohexyl triethoxysilane (1.75 g, 5.40 mmol).

Styrene ligand 28: obtained 0.319 g (32% yield) starting from Phenol 2 (0.298 g, 2.22 mmol); 11-bromoundecyl triethoxysilane (0.885 g, 2.23 mmol).

Syntheses of Ru-Complexes 29-31:

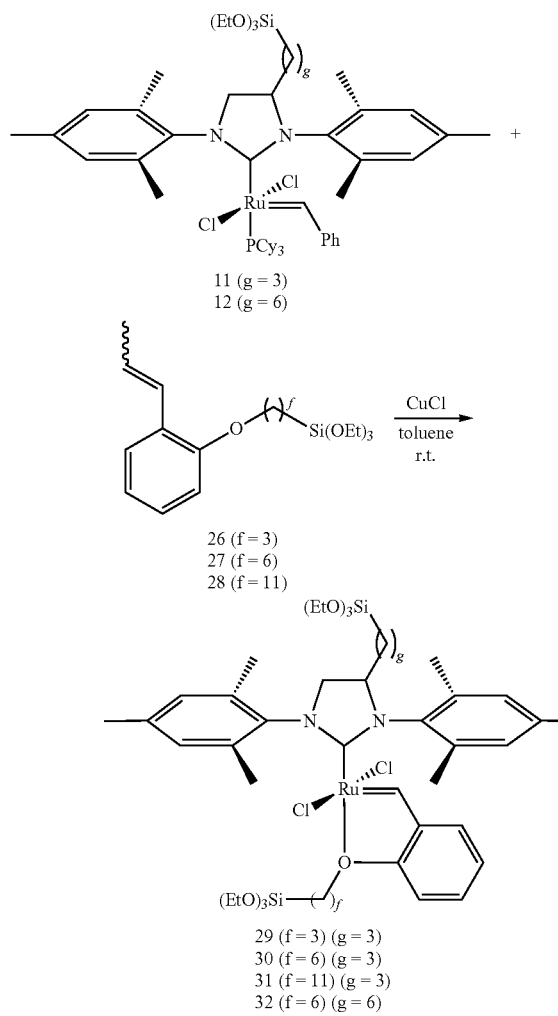

Synthesis of Ru-Complex 29:

In the glove box, an oven dried 100 mL round-bottom flask with a stir bar was charged with 11 (100 mg, 0.095 mmol). Then, styrene ligand 26 (102 mg, 0.30 mmol) was added as a solution in anhydrous toluene (10 mL). The flask was sealed with a septum and then removed from the glovebox and stirred at ambient temperature for 1 hour. Then, solid CuCl (10 mg, 0.10 mmol) was added and the mixture stirred for an additional 16 hours. [Note: as with Ru-complexes 17-25, TLC monitoring allows for easy analysis of the reaction conversion. Typical reaction times range from 4-6 hours but longer reaction times (16 hours) are acceptable]. Upon completion, the volatiles were removed under reduced pressure and the crude residue was purified by column chromatography using 6:1 hexanes:ethyl acetate and collecting the green band. This yielded 61 mg (65% yield) of 29 as a green sticky solid.

Ru-complex 30: obtained 27 mg (54% yield) starting from 11 (51 mg, 0.048 mmol) and 27 (72 mg, 0.19 mmol).

Ru-complex 31: obtained 46 mg (57% yield) starting from 11 (77 mg, 0.073 mmol) and 28 (99 mg, 0.22 mmol).

Ru-complex 32: obtained 26 mg (48% yield) starting from 12 (54 mg, 0.050 mmol) and 27 (57 mg, 0.15 mmol).

Syntheses of Solid-Supported Ru-Complexes 29-32:

Inside the dry box, silica gel was weighed into a vial containing a stir bar. Then the Ru-complex (29-32) was added to the vial containing the silica gel as a toluene solution (Note: enough toluene used to provide an adequate slurry, typically 10-15 mL and the amount of silica gel employed was based on 0.02 mmol Ru/gram silica gel). The vial was capped and the mixture was stirred at room temperature for 3-5 days. At this stage, the mixture was filtered and collected in a flitted disc extraction thimble and then the thimble containing the silica-supported catalyst was removed from the glove box in a sealed flask and finally placed into an oven dried soxhlet extraction apparatus that was under an argon atmosphere and contained a still pot of $CH_2Cl_2$. The silica-supported catalyst was continuously extracted with $CH_2Cl_2$ for 48-72 hours. Then the extraction thimble containing the solid catalyst was removed from the apparatus and dried under vacuum for 8-24 hours, yielding the pale green silica-supported Ru-complexes 29-32 which are represented in FIG. 2.

Syntheses of Styrene Ligands Comprised of Different Type Linkers:

Synthesis of Styrenic Amide 33:

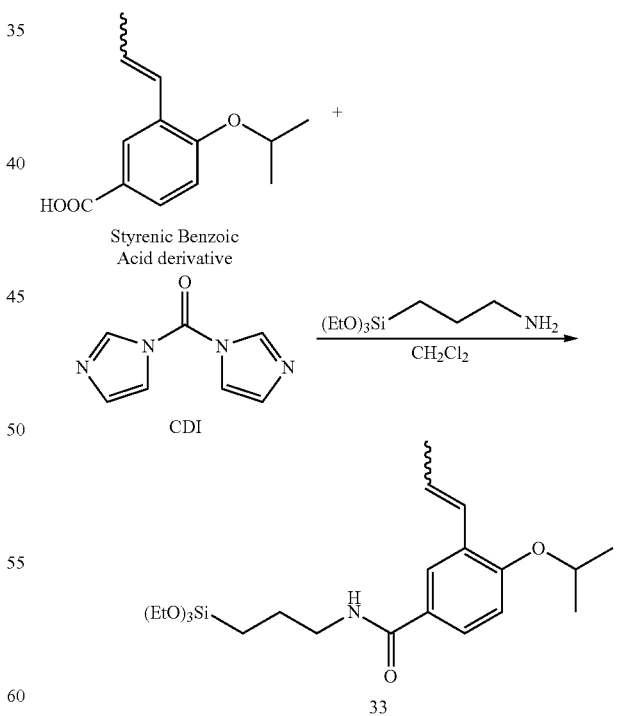

In an oven dried 100 ml round-bottom flask with stir bar, under an argon atmosphere, styrenic benzoic acid derivative (154 mg, 0.699 mmol) was added and dissolved in 10 ml of $CH_2Cl_2$. Then CDI (124 mg, 0.765 mmol) was added and stirred for 10 minutes. At this time, the 3-aminopropyl triethoxysilane (171 mg, 0.770 mmol) was added via microsyringe and the reaction stirred at room temperature for 16 hours. The solvent was removed under reduced pressure and the crude material was purified via column chromatography using 2:1 hexanes:ethyl acetate to yield 192 mg (65% yield) of 33 as a colorless oil.

Synthesis of Styrenic Urea 34:

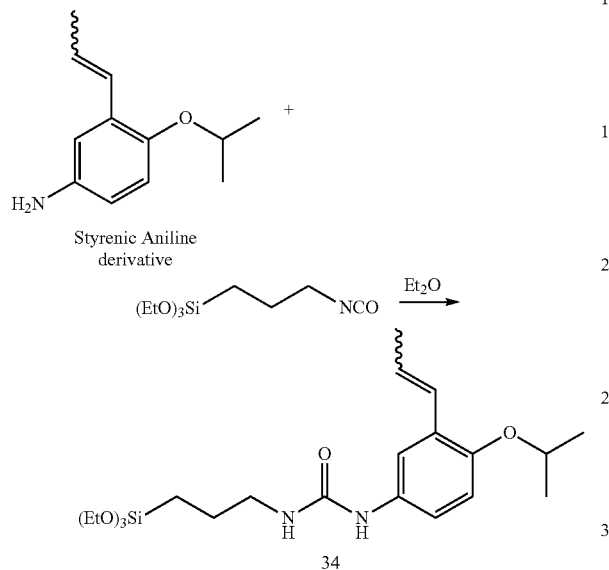

In an oven dried 50 ml round-bottom flask with stir bar, under an argon atmosphere, styrenic aniline derivative (255 mg, 1.33 mmol) was added and dissolved in 5 ml of Et$_2$O. Then 3-isocyanatopropyltriethoxysilane (337 mg, 1.36 mmol) was added and stirred for 5 hours at room temperature. The solvent was removed under reduced pressure and the crude material was purified via column chromatography using 2:1 hexanes:ethyl acetate to yield 381 mg (65% yield) of 34 as a light brown oily solid.

Synthesis of Styrenic Carbamate 35:

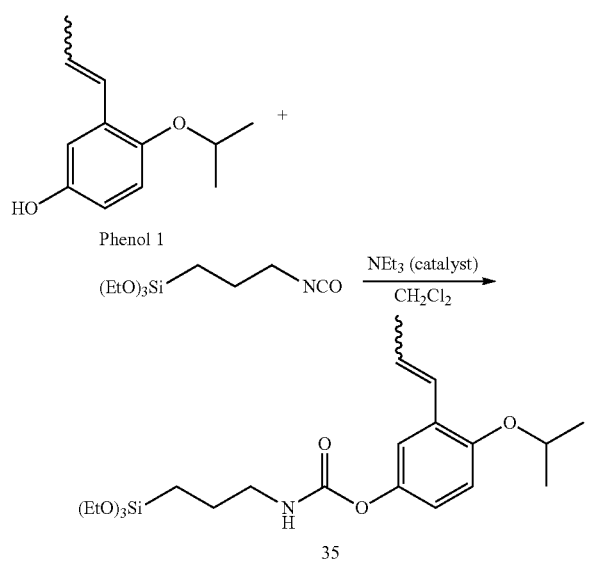

In an oven dried 50 ml round-bottom flask with stir bar, under an argon atmosphere, Phenol 1 (264 mg, 1.37 mmol) was added and dissolved in 7 ml of CH$_2$Cl$_2$. Then 3-isocyanatopropyltriethoxysilane (347 mg, 1.40 mmol) was added. Finally, three pipette drops of NEt$_3$ was added and the resulting mixture stirred for 1 hour at room temperature and then 30 minutes at 30° C. The solvent was removed under reduced pressure and the crude material was purified via column chromatography using 4:1 hexanes:ethyl acetate to yield 459 mg (76% yield) of 35 as a colorless oil.

Syntheses of Ru-Complexes 35-37 from Styrenic Amide 33:

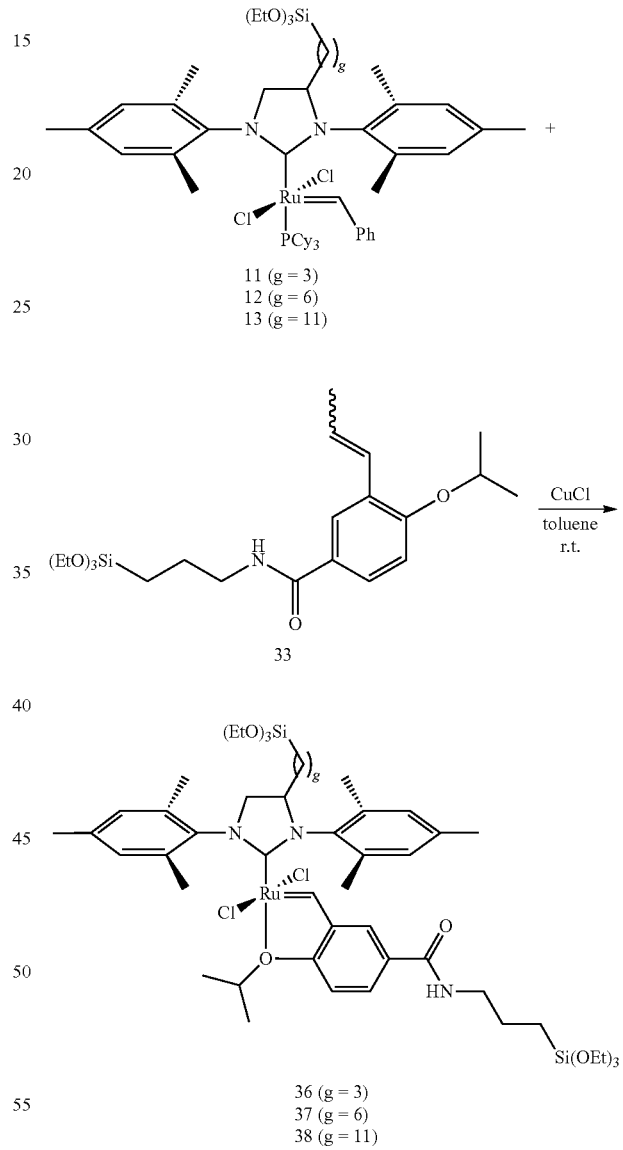

Synthesis of Ru-Complex 35:

In the glove box, an oven dried 100 mL round-bottom flask with a stir bar was charged with 11 (70 mg, 0.067 mmol). Then, styrene amide ligand 33 (65 mg, 0.15 mmol) was added as a solution in anhydrous toluene (10 mL). The flask was sealed with a septum and then removed from the glovebox and stirred at ambient temperature for 1 hour. Then, solid CuCl (~7 mg, 0.071 mmol) was added and the mixture stirred for an additional 4 hours when TLC analysis revealed no 11 remaining. Upon completion, the volatiles were removed under reduced pressure and the crude residue was purified by column chromatography using 6:1 hexanes:ethyl acetate and collecting the green band. This yielded 50 mg (70% yield) of 36 as a green sticky solid.

Ru-complex 37: obtained 27 mg (40% yield) starting from 12 (65 mg, 0.059 mmol) and 32 (63 mg, 0.15 mmol).

Ru-complex 38: obtained 41 mg (54% yield) starting from 13 (74 mg, 0.064 mmol) and 32 (63 mg, 0.15 mmol).

Synthesis of Ru-Complex 38 from Styrenic Urea 34:

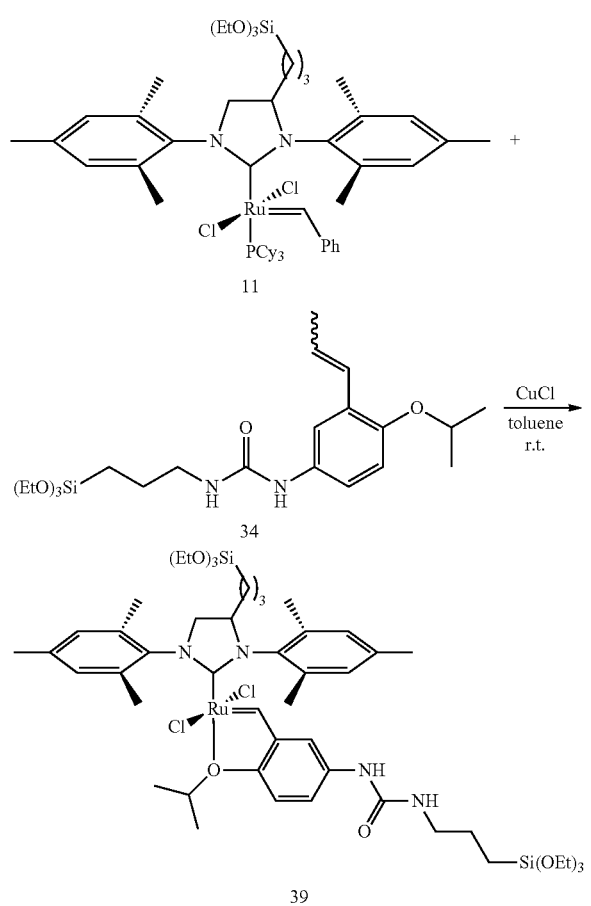

In the glove box, an oven dried 100 mL round-bottom flask with a stir bar was charged with 11 (51 mg, 0.067 mmol). Then, styrene urea ligand 34 (41 mg, 0.15 mmol) was added as a solution in anhydrous toluene (10 mL). The flask was sealed with a septum and then removed from the glovebox and stirred at ambient temperature for 1 hour. Then, solid CuCl (~7 mg, 0.071 mmol) was added and the mixture stirred for an additional 4 hours when TLC analysis revealed no 11 remaining. Upon completion, the volatiles were removed under reduced pressure and the crude residue was purified by column chromatography using 1:1 hexanes:ethyl acetate and collecting the green band. A second column was required in this case, employing 5% ethanol in CH$_2$Cl$_2$ and again collecting the green band. This yielded 39 mg (74% yield) of 39 as a green solid.

Synthesis of Ru-Complex 39 from Styrenic Carbamate 35:

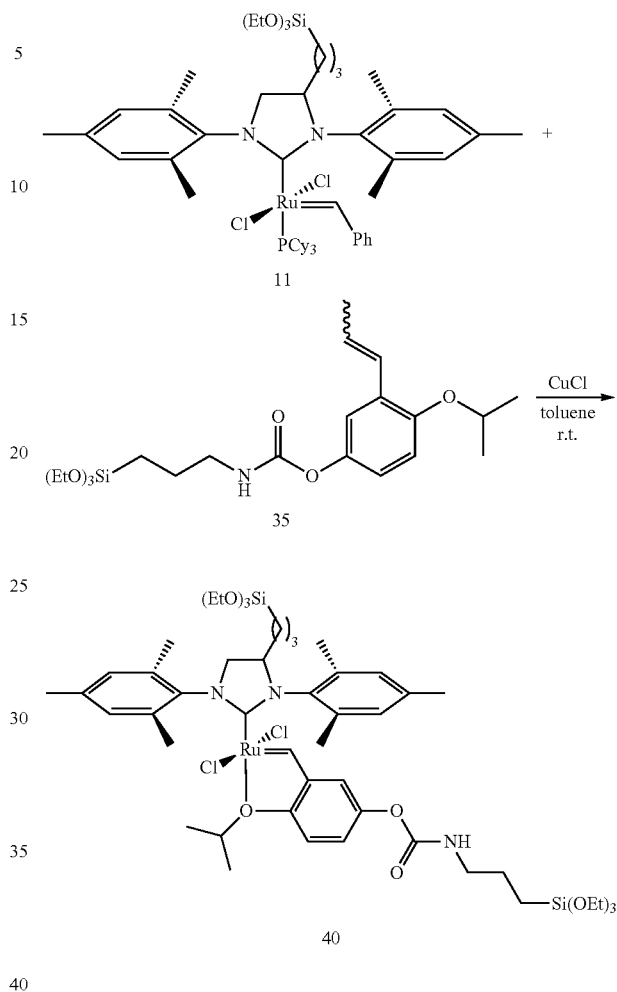

In the glove box, an oven dried 100 mL round-bottom flask with a stir bar was charged with 11 (52 mg, 0.067 mmol). Then, styrene urea ligand 35 (53 mg, 0.15 mmol) was added as a solution in anhydrous toluene (10 mL). The flask was sealed with a septum and then removed from the glovebox and stirred at ambient temperature for 1 hour. Then, solid CuCl (~7 mg, 0.071 mmol) was added and the mixture stirred for an additional 4 hours when TLC analysis revealed no 11 remaining. Upon completion, the volatiles were removed under reduced pressure and the crude residue was purified by column chromatography using 3:1 hexanes:ethyl acetate and collecting the green band. This yielded 46 mg (85% yield) of 40 as a green sticky solid.

Syntheses of Solid-Supported Ru-Complexes 36-40:

Inside the dry box, silica gel was weighed into a vial containing a stir bar. Then the Ru-complex (36-40) was added to the vial containing the silica gel as a toluene solution (Note: enough toluene used to provide an adequate slurry, typically 10-15 mL and the amount of silica gel employed was based on 0.02 mmol Ru/gram silica gel). The vial was capped and the mixture was stirred at room temperature for 3-5 days. At this stage, the mixture was filtered and collected in a flitted disc extraction thimble and then the thimble containing the silica-supported catalyst was removed from the glove box in a sealed flask and finally placed into an oven dried soxhlet extraction apparatus that was under an argon atmosphere and contained a still pot of $CH_2Cl_2$. The silica-supported catalyst was continuously extracted with $CH_2Cl_2$ for 48-72 hours. Then the extraction thimble containing the solid catalyst was removed from the apparatus and dried under vacuum for 8-24 hours, yielding the pale green silica-supported Ru-complexes 36-40 which are represented below in FIG. 3.

Synthesis of DIPP Derived Catalysts

Syntheses of Diamine 42:

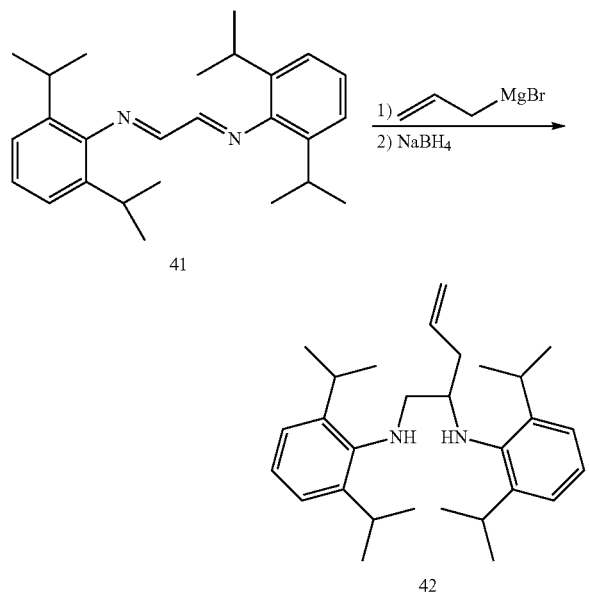

Synthesis of Diamine 42:

In an oven dried 500 ml round-bottom flask with stirbar, under an argon atmosphere, 41 (obtained by procedures described in Grasa, G. A. et al., *J. Org. Chem.*, 66, 7729-7737 (2001); 2.0 g, 5.31 mmol) was added and dissolved in 50 ml of THF. This solution was cooled to 0° C. using a dry ice/acetone bath and then allyl magnesiumbromide (8.0 ml, ~1.0 M in diethylether, 3.5 mmol) was added dropwise via syringe. After the addition, the cold bath was removed and the mixture stirred for 3 hours while warming to room temperature. Then the reaction was further diluted by the addition of methanol (50 ml) and finally an excess of sodium borohydride (1.0 g, 26.4 mmol) was added in 2 portions (half at beginning and $2^{nd}$ portion 30 min later) and the mixture stirred for a total of 16 hours. Then the reaction was quenched by the addition of a saturated $NH_4Cl$ solution until bubbling ceased. This mixture was added to a separatory funnel and the organic layer separated. The aqueous layer was extracted with hexanes (3×75 ml) and the combined organic extracts were washed with water, brine and dried over $MgSO_4$ and finally concentrated to give yellow oil. The crude material was purified via column chromatography using hexanes:ethyl acetate (30:1) to yield 1.38 g (62% yield) of 42 as a faint yellow oil.

Syntheses of NHC Salt 43:

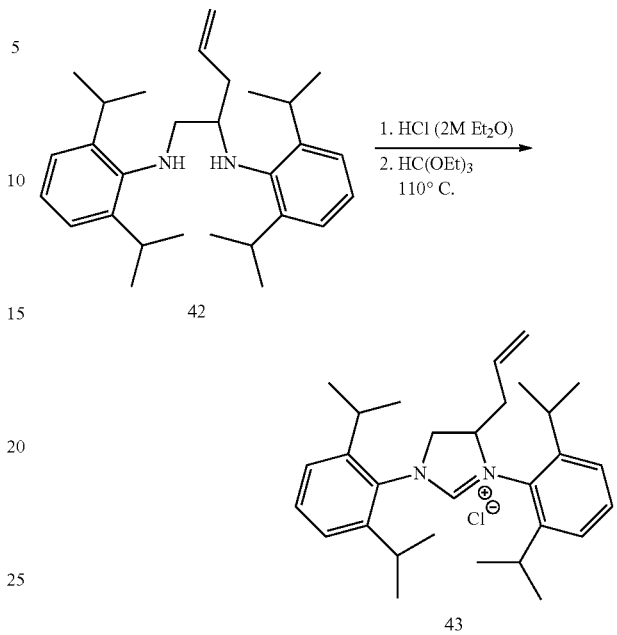

Synthesis of NHC Salt 43:

In an oven dried 100 ml round-bottom flask with stir bar, under an argon atmosphere, diamine 42 (1.38 g, 3.27 mmol) was dissolved in 30 ml of $Et_2O$ and cooled to 0° C. This was treated with a solution of HCl (2 M in $Et_2O$, 7.2 ml) to precipitate the diamine hydrochloride salt. The solid was isolated by filtration and washed with copious amounts of $Et_2O$ and then placed back into the round-bottom flask and quickly dried under vacuum. Then triethylorthoformate (15 ml) was added via syringe and an oven dried reflux condenser was placed on the round-bottom flask against an argon flow. The mixture was heated to 120° C. for 5 hours. Then the mixture was cooled and the volatiles removed under vacuum. The brown residue was then triturated with $Et_2O$ (2×20 ml) and the solvent decanted off each time. A final $Et_2O$ wash was then filtered and the solid washed with $Et_2O$ (10 ml) and finally pentane (2×10 ml) and then dried under vacuum to yield 1.00 g (66% yield over 2 steps) of 43 as an off-white solid. $^1H$ NMR ($CD_2Cl_2$, 300 MHz): δ=10.58 (s, 1H), 7.04 (s, 4 H), 5.70-5.56 (m, 1H), 5.24-5.18 (m, 2H), 4.88-4.77 (m, 1H), 4.46 (t,J=11.7 Hz, 1H), 3.97 (dd,J=12 Hz, 8.2 Hz, 1H), 2.66-2.48 (m, 2H), 2.46-2.34 (m, 18H).

Syntheses of NHC Salt 44:

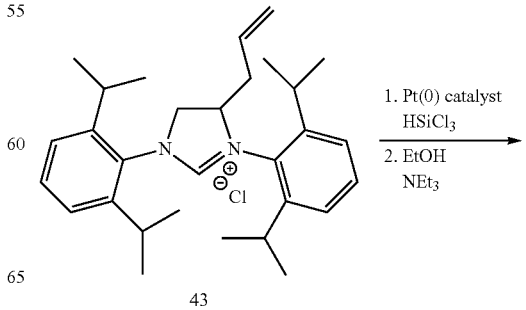

-continued

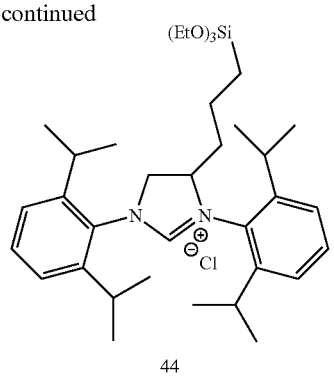

44

Synthesis of NHC Salt 44:

In an oven dried 25 ml round-bottom flask with stir bar, under an argon atmosphere, 43 (500 mg, 1.07 mmol) was added and dissolved in 15 ml of CH$_2$Cl$_2$. Then HSiCl$_3$ (5 ml, 6.7 g, 50 mmol) was added via syringe. Finally, Pt(0)-1,3-divinyl-1,1,3,3-tetramethyldisiloxane complex solution (250 µl of a 0.10 M solution in xylenes, 0.025 mmol, 2.3 mol %) was added via micro-syringe. An oven dried reflux condenser was attached, against an argon flow and the mixture was stirred at reflux for 18 h. Then the reaction mixture was cooled to room temperature and the volatiles removed under vacuum and collected in a secondary cold trap. This step is necessary to remove the excess HSiCl$_3$. The residue was then dissolved in 10 ml of CH$_2$Cl$_2$ and cooled to 0° C. at which time 5 ml of a 1/1 solution of ethanol/NEt$_3$ was added drop-wise via syringe. A white cloudy precipitate was evident upon addition and gradually disappeared. The reaction was warmed to room temperature with stirring over a period of 2 hours at which time the volatiles were removed under vacuum. The crude residue was purified by column chromatography using 10% ethanol in CH$_2$Cl$_2$ to obtain 635 mg (88% yield) of 44 as an off-white sticky solid.

Syntheses of Ru-Complexes 45:

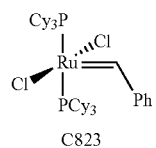

C823

Synthesis of Ru-Complex 45:

In the glove box, an oven dried 5 dram vial with a stir bar was charged with 44 (57 mg 0.090 mmol) and anhydrous toluene (2 mL). While stirring, potassium bis(trimethylsilyl) amide (19.8 mg, 0.11 mmol) was added as a solid and the reaction was stirred for 20 minutes. The solution of carbene was then filtered through a celite plug. The celite plug was washed with toluene (2 mL) and the yellow filtrate was transferred into a new, oven dried 5 dram vial with a stir bar. Following the addition of C823 (52.7 mg, 0.064 mmol) as a toluene solution (6 mL), the reaction was stirred for 3 hours at 50° C. (NMR analysis at this time indicated C823 still present) and then for 16 hours at 35° C. NMR analysis revealed that the reaction had ceased therefore it was stopped. The volatiles were removed under reduced pressure, and to the crude residue was added pentane and the mixture filtered through a pipette plug to remove some excess C823. The filtrate was concentrated to yield a dark brown residue (67 mg) that contained ~23% C823 and 77% desired product. The crude material was used without further purification in subsequent steps.

Syntheses of Ru-Complexes 46-47:

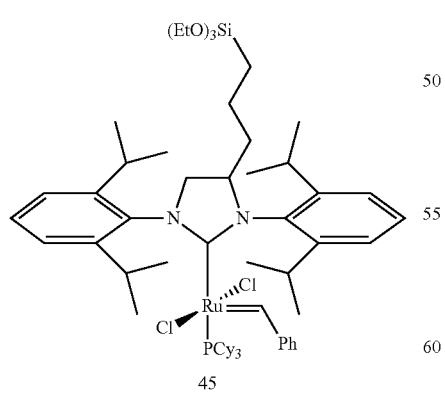

45

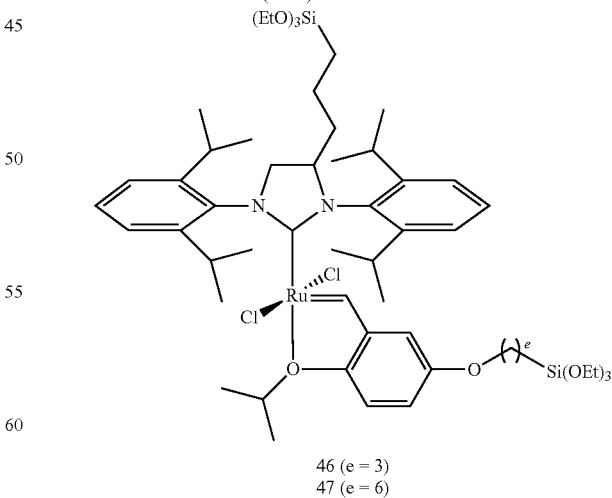

46 (e = 3)
47 (e = 6)

Synthesis of Ru-Complex 46:

In the glove box, an oven dried 100 mL round-bottom flask with a stir bar was charged with the mixture of C823 and 45 (83 mg). Then, styrene ligand 14 (84 mg, 0.25 mmol) was added as a solution in anhydrous toluene (10 mL). The flask was sealed with a septum and then removed from the glove box and stirred at ambient temperature for 1 hour. Then, solid CuCl (10 mg, 0.10 mmol) was added and the mixture stirred for an additional 16 hours. Upon completion, the volatiles were removed under reduced pressure and the crude residue was purified by column chromatography using 6:1 hexanes:ethyl acetate and collecting the green band. This yielded 57 mg of 46 as a green sticky solid.

Ru-complex 47: obtained 40 mg starting from C823+45 mixture (67 mg) and 15 (100 mg, 0.25 mmol).

Post-Silica Surface Modification of the Various Supported Catalysts

All of the above mentioned supported catalysts still have active surface silanols on the silica surface. These unreacted silanols could be further functionalized with additional functional groups. This can entail the use of inert groups that simply deactivate the surface silanols, altering the properties of the surface. Alternatively, grafting functionalized compounds, such as excesses of styrene ligands 14-16, 26-28 or 33-35 can supply catalytic species with excess ligand on the support which can lead to different properties. Examples of these post-silica surface modified catalysts are represented in FIG. 4.

Split Tests—Determination of the Heterogeneity of the Supported Catalysts

In the glovebox, 40 mg of supported catalyst was weighed into a vial containing a stir bar. Then 2 ml of $C_6D_6$ was added and the vial capped with a septum cap and wrapped with parafilm wrap. Then the vial was removed from the dry box and placed under an atmosphere of argon using a needle inlet. Then the vial was placed in an oil bath preheated to 60° C. Then RCM substrate (0.207 mmol) was added via microsyringe and the reaction stirred for 10 minutes. At this time, the split test was performed as follows: 1 ml of the reaction was removed using a syringe equipped with a 45 μm PTFE syringe filter. The filtrate was then added to a septum capped NMR tube under an argon atmosphere and a $^1$H NMR was recorded to obtain the % conversion. Then the NMR tube was placed in the same oil bath as the other half of the reaction containing the suspended catalyst and heating continued @ 60° C. total time=1 hour from start. Then $^1$H NMR of both samples were recorded to determine the % conversions and compared to the result obtained immediately after the split test. See, e.g., FIGS. 22(a) and 22(b). More detailed results are tabulated below in Tables 2-3. Table 2 reports the split test data for various dual-supported catalysts using a procedure based on the ring-closing metathesis reaction of diethyl diallylmalonate to form a di-substituted olefin. Table 3 reports the split test data for various dual-supported catalysts using a procedure based on the ring-closing metathesis reaction of diethyl allylmethallylmalonate to form a more sterically challenging tri-substituted olefin. These experiments are designed to supply information about the true heterogeneity of the supported catalyst, rather than from some active catalyst that leaches from the support.

TABLE 2

Split test results for dual-supported catalysts (RCM formation of di-substituted olefin)

| Catalyst | Catalyst Loading (mol %) | % Conversion @ split (10 minutes) | % Conversion @ end (60 minutes) | |
|---|---|---|---|---|
| | | | (filtrate) | (catalyst) |
| 17-SiO$_2$ [Type I - (3,3)] | <0.2 | 73 | 73 | >95 |
| 17-SiO$_2$ [Type I - (3,3)] | <0.2 | 74 | 74 | >95 |
| 20-SiO$_2$ [Type I - (6,3)] | <0.2 | 81 | 81 | >95 |
| 21-SiO$_2$ [Type I - (6,6)] | <0.2 | 85 | 90 | >95 |
| 18-SiO$_2$ [Type II - (3,6)] | <0.2 | 89 | 92 | >95 |

TABLE 3

Split test results for dual-supported catalysts (RCM formation of tri-substituted olefin)

| Catalyst | Catalyst Loading (mol %) | % Conversion @ split (10 minutes) | % Conversion @ end (60 minutes) | |
|---|---|---|---|---|
| | | | (filtrate) | (catalyst) |
| 18-SiO$_2$ [Type I - (3,6)] | <0.2 | 56 | 58 | 82 |
| 29-SiO$_2$ [Type II - (3,3)] | <0.2 | 41 | 42 | 81 |
| 30-SiO$_2$ [Type II - (3,6)] | <0.2 | 51 | 55 | 83 |
| 23-SiO$_2$ [Type I - (11,3)] | <0.2 | 37 | 37 | 92 |
| 25-SiO$_2$ [Type I - (11,11)] | <0.2 | 54 | 57 | 81 |
| 24-SiO$_2$ [Type I - (11,6)] | <0.2 | 44 | 46 | 87 |
| 19-SiO$_2$ [Type I - (3,11)] | <0.2 | 44 | 48 | 83 |
| 22-SiO$_2$ Type I - (6,11) | <0.2 | 50 | 54 | 88 |
| 31-SiO$_2$ Type II - (3,11) | <0.2 | 51 | 56 | 89 |
| 39-SiO$_2$ [3C-urea] | <0.2 | 36 | 36 | 75 |
| 40-SiO$_2$ [3C-carbamate] | <0.2 | 33 | 33 | 77 |
| 36-SiO$_2$ [3C-amide] | <0.2 | 45 | 46 | 79 |
| 38-SiO$_2$ [11C-amide] | <0.2 | 44 | 45 | 63 |

The results presented in Tables 2 and 3 show that all the dual-supported catalysts have passed their respective split tests, and the catalytic activity arises from a truly heterogeneous species and not from any species that has leached from the support.

Olefin Metathesis Using Supported Catalysts

Spiking Studies #1—Self-Metathesis of Methyl Oleate:

Olefin metathesis spiking studies were performed for the self-metathesis of methyl oleate in order to gauge catalyst lifetimes of the supported catalysts. At equilibrium, the reaction may be depicted as:

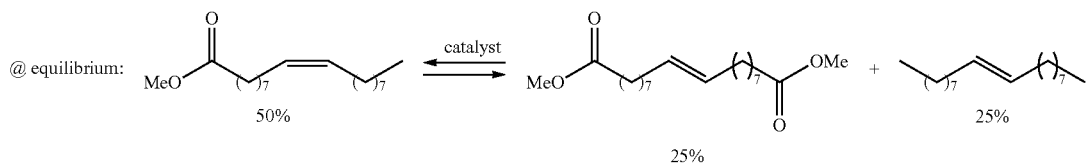

In the glovebox, 4×20 mL vials containing stir-bars were each charged with supported catalyst and sealed with a septum. The catalysts employed for this study were the 3-C mono-supported catalyst and the Type I (3,3) dual-supported catalyst (17—SiO$_2$). All vials were removed from the glovebox and set in a heating block at 30° C. Methyl oleate was added to each vial and then stirred at 30° C. Vial 1 acted as the control and samples were taken at t=1 h, 2 h, 4 h, 6 h and 24 h. At t=2 h, an additional equivalent of methyl oleate was added to vial 2. A reaction aliquot was taken immediately from vial 2 and another sample taken again at t=4 h. At t=4 h, an additional equivalent of methyl oleate was added to vial 3. A reaction aliquot was taken immediately from vial 3 and another sample taken again at t=6 h. At t=6 h, an additional equivalent of methyl oleate was added to vial 4. A reaction aliquot was taken immediately from vial 4 and another sample taken again at t=8 h. Finally, at t=24 h, final aliquots were taken from all vials. All reaction aliquots were analyzed by GC to determine the % of self-metathesis at the various reaction time-points. This experiment was designed to supply information about catalyst lifetime.

Mono Anchored Catalyst:

A Mono-anchored catalyst was first evaluated in order to determine the effects of multiple anchoring sites, as well as the location of the linker attachment sites to the catalyst ligands. Testing was performed by conducting self-metathesis reactions of methyl oleate (MO) at 30° C. using a 3-C-mono-supported catalyst 627 having a linker with a carbon chain length of 3 carbon atoms (3C) as described above. As shown below, the linker provided attachment from the NHC non-labile ligand of the complex to a silica support.

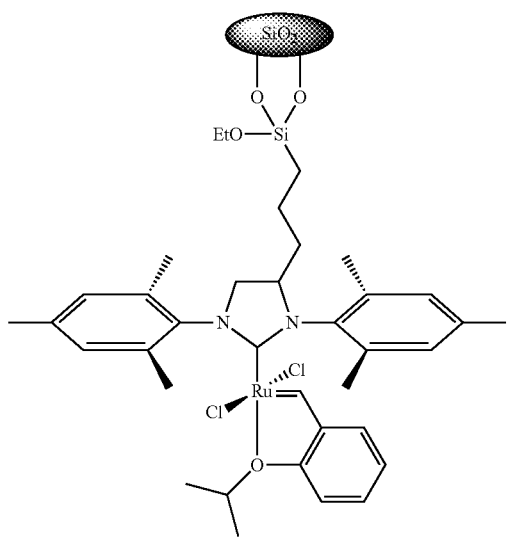

The self-metathesis reaction was conducted as described above: 56 mg of supported catalyst used in each vial. 6.6 grams of methyl oleate (MO) was added to each vial and the same amount was added for each spike (ie. @ t=2 h an additional 6.6 grams added to vial 2; @ t=4 h an additional 6.6 grams added to vial 3; @ t=6 h an additional 6.6 grams added to vial 4. Results for the 3-C mono-anchored catalyst are shown in FIG. 5. The results show that sometime between hours 2 and 4 that significant catalyst deactivation has occurred as the reactions that were spiked at 4 h and 6 h failed to reach equilibrium after spiking Type I Dual-Supported Catalysts:

The self-metathesis of methyl oleate (MO) was evaluated at 30° C. using a Type I dual-supported catalyst 627 having two linkers of specified carbon chain lengths, in which one linker was attached to a non-labile ligand of the catalyst and a second was attached to a labile ligand of the catalyst. Dual-supported Type I catalysts having linker carbon chain lengths of 3, 6 and 11 carbon atoms were evaluated for each of the linkers attached to both the non-labile and the labile ligand. In the results and figures that follow for Type I dual-supported catalysts, the linker carbon chain length is noted according to the short-hand notation (d, e), in which "d" is the number of carbon atoms in the linker providing attachment from the non-labile linker to the support, and "e" is the number of carbon atoms in the linker providing a Type I attachment from the labile linker to the support. As shown below, the linkers provided attachment from the NHC non-labile ligand of the complex to a silica support as well as attachment from the support to a chelating alkylidene labile ligand.

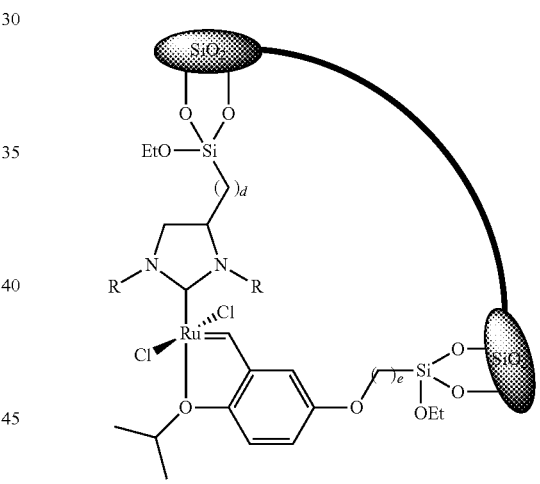

The same procedure described above for 3-C mono-supported catalyst 627 was used to test the Type I (3,3) dual-supported catalyst (17-SiO$_2$) system. Results for 17-SiO$_2$ dual-supported catalyst 627 are shown in FIG. 6. Comparison of the results of FIG. 5 and FIG. 6 shows a significant increase in the catalyst lifetime of the dual-supported catalyst compared to the mono-supported catalyst. The mono-supported catalyst failed to reach equilibrium after the 4 h and 6 h spikes; whereas the dual-supported catalyst reached equilibrium after all of the spikes performed. In order to further evaluate the various dual-supported catalysts, another spiking study was developed to supply additional data concerning catalyst lifetimes.

Spiking Studies #2—Self-Metathesis of Methyl Oleate:

In the glovebox, a 40 mL vial containing a stir-bar was charged with supported catalyst and sealed with a septum.

The catalysts employed for this study were the 3-C mono-supported catalyst and a number of the (d,e) dual-supported catalysts. The vial was removed from the glovebox and set in a heating block at 30° C. 2 mL of methyl oleate was added to the vial and then stirred at 30° C. At t=2 h, a reaction aliquot (30 µL) was taken and then an additional 2 mL of methyl oleate was added to the reaction vial. Immediately, another reaction aliquot (30 µL) was taken. This sequence was repeated at t=4 h, 6 h, and 24 h. Note, also a reaction aliquot was taken at t=8 h but no additional MO was added at this time. All reaction aliquots were analyzed by GC to determine the % of self-metathesis at the various reaction time-points. This experiment was designed to supply information about catalyst lifetime.

Mono Anchored Catalyst:

A Mono-anchored catalyst was first evaluated in order to determine the effects of multiple anchoring sites, as well as the location of the linker attachment sites to the catalyst ligands. Testing was performed by conducting self-metathesis reactions of methyl oleate (MO) at 30° C. using a mono-supported catalyst 627 having a linker with a carbon chain length of 3 carbon atoms (3C) as described above. As shown below, the linker provided attachment from the NHC non-labile ligand of the complex to a silica support.

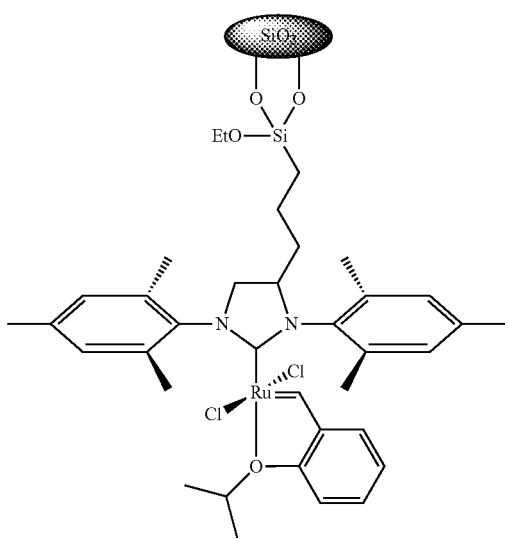

The self-metathesis reaction was conducted as described above: 18 mg of supported catalyst was used and 2 mL of methyl oleate (MO) was added to the vial containing the supported catalyst. Additional 2 mL aliquots were added at t=2 h, 4 h, 6 h, and 24 h. Results for the 3-C and 6-C mono-anchored catalyst are shown in FIG. 7. This shows that equilibrium was reached after 2 h, but then upon successive spikes equilibrium was never reached and significant catalyst deactivation has occurred.

Type I Dual-Supported Catalysts:

The self-metathesis of methyl oleate (MO) was evaluated at 30° C. using a Type I dual-supported catalyst 627 having two linkers of specified carbon chain lengths, in which one linker was attached to a non-labile ligand of the catalyst and a second was attached to a labile ligand of the catalyst. Dual-supported Type I catalysts having linker carbon chain lengths of 3, 6 and 11 carbon atoms were evaluated for each of the linkers attached to both the non-labile and the labile ligand. In the results and figures that follow for Type I dual-supported catalysts, the linker carbon chain length is noted according to the short-hand notation (d, e), in which "d" is the number of carbon atoms in the linker providing attachment from the non-labile linker to the support, and "e" is the number of carbon atoms in the linker providing a Type I attachment from the labile linker to the support. As shown below, the linkers provided attachment from the NHC non-labile ligand of the complex to a silica support as well as attachment from the support to a chelating alkylidene labile ligand.

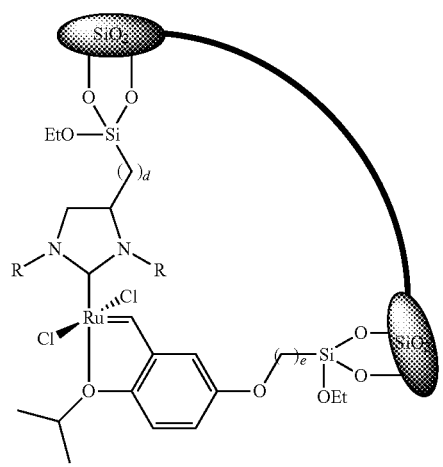

Using the same procedure described above for 3-C and 6-C mono-supported catalyst 627, various dual-supported catalysts (d,e) were tested. Results for Type I (d,e) dual-supported catalyst 627 are shown in FIGS. 8-10. These results show a dramatic difference between the mono-supported catalyst and the Type I (d,e) dual-supported catalysts. The Type I (d,e) dual-supported catalysts show increased catalyst lifetimes compared to the mono-supported catalyst, often reaching equilibrium after the 6 h spike and showing increasing conversion even after 24 h.

Type II Dual-Supported Catalysts:

The self-metathesis of methyl oleate (MO) was evaluated at 30° C. using a Type II dual-supported catalyst 627 having two linkers of specified carbon chain lengths, in which one linker was attached to a non-labile ligand of the catalyst and a second was attached to a labile ligand of the catalyst. Dual-supported Type II catalysts having linker carbon chain lengths of 3, 6 and 11 carbon atoms were evaluated for each of the linkers attached to both the non-labile and the labile ligand. In the results and figures that follow for Type II dual-supported catalysts, the linker carbon chain length is noted according to the short-hand notation (d, f), in which "d" is the number of carbon atoms in the linker providing attachment from the non-labile linker to the support, and "f" is the number of carbon atoms in the linker providing a Type II attachment from the labile linker to the support. As shown below, the linkers provided attachment from the NHC non-labile ligand of the complex to a silica support as well as attachment from the support to a chelating alkylidene labile ligand.

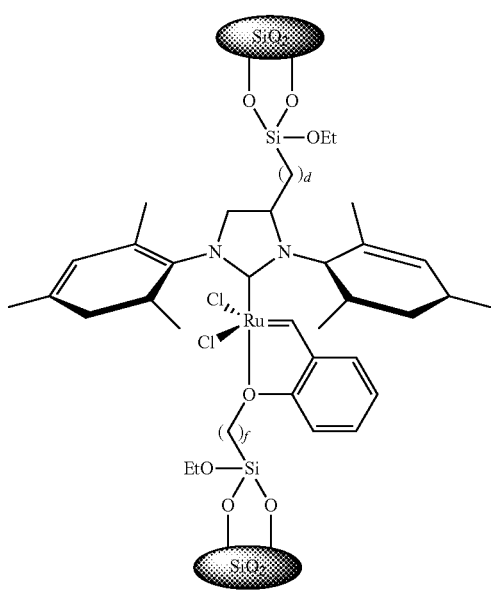

Using the same spiking procedure described above for mono-supported and the Type I dual-supported catalyst 627, spiking studies were also performed for the Type II dual-supported catalysts. Results for these Type II dual-supported catalyst tests are shown in FIG. 11. In general, the Type II (d,f) dual-supported catalysts behave in a similar fashion to the Type I systems, offering increased catalyst lifetimes compared to the mono-supported catalysts.

Spiking Studies—Self-Metathesis of 5-Decenyl Acetate:

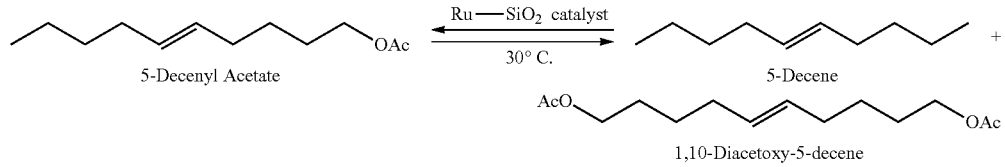

In the glovebox, a 20 mL vial containing a stir-bar was charged with supported catalyst (10 mg) and sealed with a septum. The vial was removed from the glovebox and set in a heating block at 30° C. 1 gram of 5-decenyl acetate was added to the vial and then stirred at 30° C. At t=1 h, a reaction aliquot (30 µL) was taken and then an additional 1 gram of 5-decenyl acetate was added to the reaction vial. Immediately, another reaction aliquot (30 µL) was taken. This sequence was repeated at t=2 h, 3 h, 4 h, 5 h, 6 h and >20 h. All reaction aliquots were analyzed by GC to determine the % of self-metathesis at the various reaction timepoints. This experiment was designed to supply additional information about catalyst lifetime. Results for 3C-mono-supported catalyst 627, 6C-mono-supported catalyst 627, and homogeneous C627 are shown in FIG. 12. Results for the Type I dual-supported (d,e) catalysts are shown in FIGS. 13-15. Results for the Type II dual-supported (d,f) catalysts are shown in FIG. 16. Results for 3C-dual-supported amide, 11C-dual-supported amide, 3C-dual-supported urea and the 3C-dual-supported carbamate are shown in FIG. 17. These results show that all of the dual-supported catalysts tested perform better than homogeneous C627 and the mono-supported catalysts under identical reaction conditions.

These results also follow the same trends that were observed with the methyl oleate spiking studies.

Hexenolysis of Soybean Oil (Batch-Type Reaction):

Inside the glovebox, a 40 mL vial with stir bar was charged with soybean oil (7.75 g, 9.0 mmol), 1-hexene (10.1 g, 120 mmol, 3 equivalents per double bond of the soy TAG) and then the solid-supported catalyst (10 mg, ~0.0002 mmol, ~5 ppm). The reaction vials were removed from the glovebox and stirred at 30° C. At the appropriate time, 0.1 mL aliquots were removed and transesterified with NaOMe in MeOH, treated with THMP and then analyzed by GC. In order to track the hexenolysis reaction, the production and yield of methyl 9-decenoate (Me9DA) product were monitored. Both decenes and Me9DA yields have been normalized to the methyl palmitate internal standard. From this value, approximate yields and turnover numbers (TON) for Me9DA have been calculated. The results are tabulated in Tables 4-10, using the catalysts shown in FIG. 1. The results in Tables 4-10 show that all of the dual-supported catalysts tested display good activity for the hexenolysis of SBO supplying TON's on the order of 30,000-45,000.

TABLE 4

Hexenolysis of Soybean oil (TAG) with Type I Supported Catalysts

| Catalyst | Time (h) | Me9DA Yield (%)[1] | Me9DA TON[2] |
|---|---|---|---|
| 17-SiO$_2$ | 2 | 12.3 | 24,566 |
| [Type I - (3,3)] | 4 | 15.3 | 30,587 |
| (batch 1) | 22 | 18.4 | 36,834 |
|  | 2 | 12.7 | 25,461 |
|  | 4 | 15.2 | 30,296 |
|  | 22 | 15.2 | 30,489 |
| 17-SiO$_2$ | 2 | 5.5 | 11,065 |
| [Type I - (3,3)] | 4 | 8.1 | 16,177 |
| (batch 2) | 22 | 9.9 | 19,794 |
|  | 2 | 15.3 | 30,536 |
|  | 24 | 18.0 | 36,055 |
|  | 2 | 13.1 | 26,266 |
|  | 2 | 9.8 | 19,539 |
|  | 2 | 4.2 | 8,435 |
| 18-SiO$_2$ | 2 | 13.4 | 26,700 |
| [Type I - (3,6)] | 4 | 16.2 | 32,343 |
|  | 22 | 19.1 | 38,103 |
|  | 2 | 9.8 | 19,564 |
|  | 4 | 15.2 | 30,417 |
|  | 23 | 16.4 | 32,875 |
|  | 2 | 13.3 | 26,610 |
|  | 4 | 17.1 | 34,120 |
|  | 24 | na | na |
|  | 2 | 6.5 | 13,000 |

TABLE 4-continued

Hexenolysis of Soybean oil (TAG) with Type I Supported Catalysts

| Catalyst | Time (h) | Me9DA Yield (%)[1] | Me9DA TON[2] |
|---|---|---|---|
| 19-SiO$_2$ [Type I - (3,11)] | 4 | 17.1 | 34,108 |
| | 22 | 20.9 | 41,725 |
| | 2 | 13.6 | 27,222 |
| | 4 | 16.5 | 33,045 |
| | 24 | 18.9 | 37,780 |
| 20-SiO$_2$ [Type I - (6,3)] | 2 | 13.2 | 26,320 |
| | 4 | 15.0 | 30,076 |
| | 24 | 18.5 | 36,894 |
| 21-SiO$_2$ [Type I - (6,6)] | 2 | 14.2 | 28,348 |
| | 4 | 17.3 | 34,504 |
| | 22 | 19.6 | 39,129 |
| | 2 | 13.5 | 27,034 |
| | 4 | 14.7 | 29,336 |
| | 22 | na | na |
| 22-SiO$_2$ [Type I - (6,11)] | 2 | 13.4 | 26,763 |
| | 4 | 15.6 | 31,190 |
| | 22 | 18.8 | 37,617 |
| 23-SiO$_2$ [Type I - (11,3)] | 2 | 12.9 | 25,825 |
| | 4 | 16.3 | 32,528 |
| | 22 | 16.3 | 32,533 |
| | 2 | 9.3 | 18,652 |
| | 4 | 13.4 | 26,857 |
| | 23 | 15.5 | 30,920 |
| 24-SiO$_2$ [Type I - (11,6)] | 2 | 17.5 | 34,985 |
| | 22 | 17.0 | 34,048 |
| | 2 | 14.8 | 29,508 |
| | 4 | 15.6 | 31,186 |
| | 22 | 16.7 | 33,486 |
| 25-SiO$_2$ [Type I - (11,11)] | 2 | 4.6 | 9,277 |
| | 4 | 16.7 | 33,358 |
| | 26 | 17.4 | 34,739 |
| | 2 | 15.7 | 31,405 |
| | 2 | 13.2 | 26,437 |
| | 4 | 14.6 | 29,282 |
| | 24 | 18.8 | 37,566 |
| | 2 | 13.7 | 27,428 |
| | 4 | 16.8 | 33,688 |
| | 23 | 16.2 | 32,373 |

[1]Me9DA yields have been normalized to Me9DA yields produced by butenolysis of SBO. This was done by backing out the amount of 5-decene produced.
[2]Me9DA TON is the turn over number of the normalized Me9DA.

TABLE 5

Hexenolysis of Soybean oil (TAG) with Type I Urea, Cabamate, and Amide Supported Catalysts

| Catalyst | Time (h) | Me9DA Yield (%)[1] | Me9DA TON[2] |
|---|---|---|---|
| 39-SiO$_2$ [3C-Urea] | 2 | 11.0 | 22,004 |
| | 4 | 15.5 | 30,950 |
| | 23 | 15.9 | 31,862 |
| 40-SiO$_2$ [3C-Carbamate] | 2 | 17.7 | 35,297 |
| | 22 | 21.6 | 43,131 |
| | 2 | 14.2 | 28,383 |
| | 4 | 17.3 | 34,567 |
| | 23 | 17.2 | 34,319 |
| 36-SiO$_2$ [3C-Amide] | 2 | 5.8 | 11,572 |
| | 2 | 5.3 | 10,567 |
| | 4 | 8.1 | 16,245 |
| | 24 | 12.2 | 24,354 |
| | 2 | 6.9 | 13,870 |
| | 4 | 12.8 | 25,596 |
| | 22 | 15.5 | 31,026 |
| 38-SiO$_2$ [11C-Amide] | 2 | 10.9 | 21,706 |
| | 4 | 13.5 | 27,065 |
| | 26 | 14.7 | 29,367 |
| | 2 | 13.5 | 26,979 |
| | 4 | 16.6 | 33,191 |
| | 22 | 17.4 | 34,848 |

[1]Me9DA yields have been normalized to Me9DA yields produced by butenolysis of SBO. This was done by backing out the amount of 5-decene produced.
[2]Me9DA TON is the turn over number of the normalized Me9DA.

TABLE 6

Hexenolysis of Soybean oil (TAG) with Type II Supported Catalysts

| Catalyst | Time (h) | Me9DA Yield (%)[1] | Me9DA TON[2] |
|---|---|---|---|
| 29-SiO$_2$ [Type II - (3,3)] | 2 | 14.7 | 29,322 |
| | 4 | 16.8 | 33,610 |
| | 24 | 17.6 | 35,161 |
| 30-SiO$_2$ [Type II - (3,6)] | 2 | 15.5 | 30,960 |
| | 4 | 16.0 | 32,023 |
| | 26 | 16.7 | 33,459 |
| | 2 | 13.0 | 26,011 |
| | 4 | 14.9 | 29,877 |
| | 24 | 19.4 | 38,855 |
| | 2 | 12.1 | 24,252 |
| | 4 | 19.0 | 37,969 |
| | 24 | na | na |
| 31-SiO$_2$ [Type II - (3,11)] | 2 | 14.5 | 29,035 |
| | 4 | 16.5 | 32,935 |
| | 24 | 16.9 | 33,791 |
| 32-SiO$_2$ [Type II - (6,6)] | 2 | 20.6 | 41,252 |
| | 4 | 21.0 | 42,007 |
| | 24 | na | na |

[1]Me9DA yields have been normalized to Me9DA yields produced by butenolysis of SBO. This was done by backing out the amount of 5-decene produced.
[2]Me9DA TON is the turn over number of the normalized Me9DA.

TABLE 7

Hexenolysis of Soybean oil (TAG) with Type I Silica Treated Supported Catalysts

| Catalyst | Time (h) | Me9DA Yield (%)[1] | Me9DA TON[2] |
|---|---|---|---|
| 18-SiO$_2$ + Hexyl-Si(OEt)$_3$ [Type I - (3,6)] + Hex-Si(OEt)$_3$ | 2 | 17.2 | 34,485 |
| | 4 | 19.3 | 38,551 |
| | 22 | 21.2 | 42,433 |
| | 2 | 18.7 | 37,482 |
| | 4 | 19.4 | 38,838 |
| | 22 | 20.4 | 40,810 |
| | 0.25 | 0.7 | 1,326 |
| | 0.5 | 2.2 | 4,415 |
| | 0.75 | 5.6 | 11,144 |
| | 1 | 9.3 | 18,671 |
| | 1.5 | 12.9 | 25,794 |
| | 2 | 15.2 | 30,485 |
| | 4 | 17.8 | 35,550 |
| | 70 | 21.3 | 42,490 |
| 18-SiO$_2$ + Diphenyl-Si(OEt)$_2$ [Type I - (3,6)] + Ph$_2$—Si(OEt)$_2$ | 2 | 14.7 | 29,450 |
| | 4 | 17.2 | 34,483 |
| | 24 | 19.1 | 38,216 |
| | 2 | 10.3 | 20,516 |
| | 4 | 14.0 | 27,941 |
| | 23 | 15.3 | 30,547 |

TABLE 7-continued

Hexenolysis of Soybean oil (TAG) with Type I Silica Treated Supported Catalysts

| Catalyst | Time (h) | Me9DA Yield (%)[1] | Me9DA TON[2] |
|---|---|---|---|
| 23-SiO$_2$ + Hexyl-Si(OEt)$_3$ | 2 | 16.6 | 33,274 |
| [Type I - (11,3)] + | 4 | 16.4 | 32,730 |
| Hex-Si(OEt)$_3$ | 24 | 20.5 | 40,969 |
|  | 2 | 12.6 | 25,234 |
|  | 4 | 15.1 | 30,221 |
|  | 23 | 16.3 | 32,618 |
| 23-SiO$_2$ + Diphenyl-Si(OEt)$_2$ | 2 | 16.7 | 33,437 |
| [Type I - (11,3)] + | 4 | 17.7 | 35,490 |
| Ph$_2$—Si(OEt)$_2$ | 24 | na | na |
|  | 2 | 14.0 | 28,049 |
|  | 4 | 16.0 | 32,072 |
|  | 23 | 16.6 | 33,201 |

[1]Me9DA yields have been normalized to Me9DA yields produced by butenolysis of SBO. This was done by backing out the amount of 5-decene produced.
[2]Me9DA TON is the turn over number of the normalized Me9DA.

TABLE 8

Hexenolysis of Soybean oil (TAG) with Type II Silica Treated Supported Catalysts

| Catalyst | Time (h) | Me9DA Yield (%)[1] | Me9DA TON[2] |
|---|---|---|---|
| 31-SiO$_2$ + Hexyl-Si(OEt)$_3$ | 2 | 17 | 33,894 |
| [Type II - (3,6)] + | 4 | 17.8 | 35,553 |
| Hex-Si(OEt)$_3$ | 23 | na | na |
|  | 2 | 14.5 | 28,961 |
|  | 4 | 16.5 | 33,009 |
|  | 23 | na | na |
|  | 2 | 14.5 | 28,958 |
|  | 4 | 13.2 | 26,467 |
|  | 24 | 16.2 | 32,306 |
| 31-SiO$_2$ + Diphenyl-Si(OEt)$_2$ | 2 | 16.8 | 33,675 |
| [Type II - (3,6)] + | 4 | 18 | 35,993 |
| Ph$_2$—Si(OEt)$_2$ | 23 | 20.5 | 41,040 |
|  | 2 | 15.3 | 30,522 |
|  | 4 | 16.3 | 32,561 |
|  | 23 | 18.1 | 36,138 |
|  | 2 | 12 | 23,980 |
|  | 4 | 12.6 | 25,279 |
|  | 23 | 15.8 | 31,658 |

[1]Me9DA yields have been normalized to Me9DA yields produced by butenolysis of SBO. This was done by backing out the amount of 5-decene produced.
[2]Me9DA TON is the turn over number of the normalized Me9DA.

TABLE 9

Hexenolysis of Soybean oil (TAG) with Type I with Excess Immobilized Hoveyda Ligand Supported Catalysts

| Catalyst | Time (h) | Me9DA Yield (%)[1] | Me9DA TON[2] |
|---|---|---|---|
| 18-SiO$_2$ + 10 equiv. ligand 15 | 2 | 17.1 | 34,226 |
| [Type I - (3,6)] + 10 equiv. 15 | 4 | 18.4 | 36,784 |
|  | 22 | 20.7 | 41,461 |
|  | 2 | 18.3 | 36,547 |
|  | 4 | 19.4 | 38,729 |
|  | 22 | 20.1 | 40,177 |
| 18-SiO$_2$ + 2 equiv. ligand 15 | 2 | 13.9 | 27,883 |
| [Type I - (3,6)] + 2 equiv. 15 | 4 | 16.3 | 32,597 |
|  | 22 | 19.4 | 38,720 |
|  | 2 | 11.2 | 22,331 |
|  | 4 | 12.4 | 24,793 |
|  | 22 | 15.2 | 30,298 |
| 24-SiO$_2$ + 10 equiv. ligand 15 | 2 | 16.1 | 32,253 |
| [Type I - (11,6)] + 10 equiv. 15 | 4 | 18.4 | 36,887 |
|  | 24 | 20.4 | 40,727 |
|  | 2 | 6.0 | 12,001 |
|  | 4 | 10.2 | 20,467 |
|  | 23 | 14.5 | 28,899 |
| 24-SiO$_2$ + 2 equiv. ligand 15 | 2 | 16.0 | 31,913 |
| [Type I - (11,6)] + 2 equiv. 15 | 4 | 17.4 | 34,793 |
|  | 22 | 20.7 | 41,291 |
|  | 2 | 13.7 | 27,371 |
|  | 4 | 10.2 | 20,478 |
|  | 22 | 12.6 | 25,251 |

[1]Me9DA yields have been normalized to Me9DA yields produced by butenolysis of SBO. This was done by backing out the amount of 5-decene produced.
[2]Me9DA TON is the turn over number of the normalized Me9DA.

TABLE 10

Hexenolysis of Soybean oil (TAG) with Misc. Supported and Homogeneous Catalysts

| Catalyst | Time (h) | Me9DA Yield (%)[1] | Me9DA TON[2] |
|---|---|---|---|
| 18-SiO$_2$ | 2 | 3.2 | 6,388 |
| [Type I - (3,6)] | 4 | 3.3 | 6,568 |
| (lower catalyst supported) | 23 | 5.3 | 10,510 |
| 3C-Mono | 2 | 1.8 | 3,616 |
|  | 4 | 7.2 | 14,367 |
|  | 22 | 8.5 | 17,011 |
| 6C-Mono | 2 | 0.5 | 1,037 |
|  | 4 | 0.5 | 934 |
|  | 24 | 0.6 | 1,157 |
| Homogeneous Catalysis |  |  |  |
| C831 (5 ppm) | 2 | 25.5 | 50,939 |
| C627 (5 ppm) | 2 | 23.6 | 47,143 |
| C627 (3 ppm) | 2 | 22.5 | 75,042 |
| C831 (20 ppm) | 2 | 24.6 | 12,299 |

[1]Me9DA yields have been normalized to Me9DA yields produced by butenolysis of SBO. This was done by backing out the amount of 5-decene produced.
[2]Me9DA TON is the turn over number of the normalized Me9DA.

Hexenolysis of Soybean Oil (Flow-Through a Fixed Catalyst Bed):

Inside the glovebox, a catalyst bed was prepared as follows: a pipette was charged with some glass wool, a small layer of sand, a small layer of celite, and finally 15 mg (<0.0003 mmols) of supported catalyst. Then a 2-3 mL of toluene was passed through the catalyst bed to pack it appropriately. Then 1 mL of a standard solution of SBO in 1-hexene (0.379 M) was added on top of the catalyst bed and allowed to flow through the bed and collected in a vial. Efforts were made to keep the overall time for the 1 mL to pass through catalyst bed at 5-10 minutes. Note, a pipette bulb was used to apply some pressure in aiding the solution through the catalyst bed. After the first 1 mL of SBO/1-hexene solution passed through the catalyst bed, a 2$^{nd}$ 1 mL was added in an identical fashion as above. This was repeated for a total of 10 passes. After each 1 mL pass was collected, it was removed from the glovebox and an aliquot was taken and treated with NaOMe solution, then THMP solution and analyzed by GC. The results for various catalysts tested are presented in Table 11 shown below in terms of kg of Me-9DA/h/mol of catalyst per double bond. These results show that the dual-supported catalysts are all effective catalysts for flow-through processes involving fixed catalyst beds.

TABLE 11

Hexenolysis of Soybean oil (TAG) via flow-through a fixed catalyst bed with a variety of dual-anchored catalysts.

| Catalyst | Cycle # (kg of Me-9 DA/h/mmol of catalyst) | | | | | | | | | |
|---|---|---|---|---|---|---|---|---|---|---|
| | 1 | 2 | 3 | 4 | 5 | 6 | 7 | 8 | 9 | 10 |
| 18-SiO$_2$ | 440 | 545 | 648 | 518 | 492 | 540 | 441 | 425 | 428 | 321 |
| 24-SiO$_2$ | 367 | 602 | 548 | 593 | 434 | 544 | 599 | 502 | 467 | 309 |
| 30-SiO$_2$ | 512 | 880 | 525 | 552 | 527 | 504 | 407 | 388 | 392 | 304 |
| 39-SiO$_2$ | 160 | 324 | 332 | 316 | 278 | 350 | 309 | 203 | 213 | 104 |
| 40-SiO$_2$ | 117 | 352 | 510 | 459 | 416 | 524 | 500 | 456 | 369 | 310 |
| 36-SiO$_2$ | 50 | 54 | 94 | 101 | 108 | 164 | 171 | 145 | 72 | 76 |
| 18-SiO$_2$ + Hexyl-Si(OEt)$_3$ | 542 | 497 | 308 | 269 | 267 | 274 | 428 | 388 | 223 | 161 |
| 18-SiO$_2$ + Ph$_2$—Si(OEt)$_2$ | 339 | 506 | 409 | 388 | 426 | 508 | 428 | 404 | 373 | 260 |
| 18-SiO$_2$ + 10 equiv. 15 | 331 | 150 | 138 | 171 | 158 | 224 | 223 | 174 | 153 | 142 |

Octenolysis of Soy FAME Via Continuous Flow Through a Fixed Catalyst Bed Employing a HPLC System:

Preparing Catalyst Bed for Flow-Through Experiments Using the HPLC Set-Up:

When employing the HPLC set-up for continuous flow experiments, the flow of reagents was vertically upward from the bottom to the top controlled by an HPLC pump at a specified flow rate. This resulted in flow, first through a bottom column (125 mm long×4.6 mm diameter column) that is filled with activated neutral alumina and acts as a guard column. Then, the flow continues through the column on top (75 mm long×4.6 mm diameter) that houses the catalyst bed.

Catalyst Bed Preparation:

In the glovebox, 25 mg of supported catalyst is weighed into a vial and then 100 mg of celite is added. This is thoroughly mixed and then added into the 75 mm column that is sealed with a fritted disc HPLC column connection. Then CH$_2$Cl$_2$ is used to pack the celite/supported catalyst mixture. This is performed using a burette bulb to force the CH$_2$Cl$_2$ through the mixture and out the bottom through the flitted disc. Then the same activated alumina used in the guard column is added on top of the catalyst bed to fill any void space. Then some additional CH$_2$Cl$_2$ is added to further pack the alumina and the catalyst bed. Total CH$_2$Cl$_2$ used for the packing is ~2 mL. Note: when the catalyst bed is used, it is inverted so the substrate(s) flow through the added alumina first and then pass through the supported catalyst/celite mixture. Once the packing is complete, the assembly of the HPLC column is finished by tightening the parts with wrenches, it is placed in an e-flask and sealed with a rubber stopper and removed from the glovebox awaiting set-up with the HPLC pump.

Preparing the HPLC Set-Up and Commencing the Reaction:

A previously prepared mixture of Soy FAME/1-octene (3 equiv. 1-octene per double bond) from the glovebox in a HPLC bottle is connected to one of the solvent lines of the quaternary pump and placed under a positive argon pressure using an inlet needle at the top of the HPLC bottle cap. Then, using flow rate of 5 mL/min, the pump is primed with the purge valve open for a couple minutes and then purge valve closed and mixture passed through the column compartment and outlet for ~1 min. Pump is turned to standby, and then the pre-guard alumina column is connected at the column compartment outlet and a 2$^{nd}$ piece of tubing is placed on the outlet of the alumina column. This column is flushed with substrate for ~30 seconds to remove any potential air bubbles. Finally, the catalyst column is removed from the sealed e-flask and attached to the tubing from the alumina column outlet and then an outlet for sample collection is connected to the catalyst bed column. Flow rate change to 3 mL/min and then set-up flushed for ~30 seconds and then flow rate set for desired flow of the reaction and reaction timing commenced.

Standard Screening Protocol:

Alkenolysis was performed by cycling between 2 different flow rates at allotted time intervals and then monitoring the extent of conversion by analyzing 1 mL fractions throughout the HPLC sequence. The standard screening protocol #1 is as follows:

At 1 mL/min flow rate, collect 5×1 mL fractions (cycle time of 5 min)

Decrease the flow rate to 0.25 mL/min and collect 5×1 mL fractions (cycle time is 20 min)

Repeat 5×1 mL/min and 0.25 mL/min sequences 6 additional times (total time of cycles 175 min and 70 fractions)

Decrease the flow rate to 0.05 mL/min and collect 3×1 mL fractions (cycle time of 60 min)

Decrease the flow rate to 0.017 mL/min and collect 1–2×1 mL fractions (cycle time of 60-120 min)

Total reaction time was 355 min and 75×1 mL fractions were collected.

Note 1: Selective fractions throughout the sequence were analyzed by GC and the GC area percent (%) of Me-9DA in each fraction was reported and graphed. A representative graph is shown in FIG. 18 for standard screening protocol. Included below in Table 12 are the results obtained with the various supported catalysts under this standard screening protocol. It should be further noted that 20% Me-9DA by GC represents the theoretical maximum yield of Me-9DA for this equilibrium process when 3 equivalents of 1-octene is employed.

TABLE 12

Octenolysis of Soy FAME under the standard screening protocol using the HPLC system and a number of dual-anchored catalysts

| Catalyst | Avg. Cycle 1-7 (0.25 mL/min)[1] | Avg. Cycle 71-73 (0.05 mL/min) | Avg. Cycle 74-75 (0.017 mL/min) |
|---|---|---|---|
| 17-SiO$_2$ | 1.59 | 3.56 | 10.08 |
| 18-SiO$_2$ | 2.67 | 5.74 | 12.29 |
| 19-SiO$_2$ | 4.35 | 9.92 | 15.08 |
| 21-SiO$_2$ | 2.86 | 6.72 | 14.91 |
| 22-SiO$_2$ | 4.50 | 10.60 | 17.55 |
| 23-SiO$_2$ | 2.83 | 8.99 | 16.63 |
| 24-SiO$_2$ | 3.16 | 9.82 | 17.56 |
| 24-SiO$_2$ | 2.64 | 8.19 | 16.64 |

TABLE 12-continued

Octenolysis of Soy FAME under the standard screening protocol using the HPLC system and a number of dual-anchored catalysts

| Catalyst | Avg. Cycle 1-7 (0.25 mL/min)[1] | Avg. Cycle 71-73 (0.05 mL/min) | Avg. Cycle 74-75 (0.017 mL/min) |
|---|---|---|---|
| 25-SiO$_2$ | 4.95 | 12.17 | 18.33 |
| 25-SiO$_2$ | 4.04 | 14.35 | 20.96 |
| 30-SiO$_2$ | 3.45 | 9.77 | 17.61 |
| 31-SiO$_2$ | 3.24 | 5.81 | 11.19 |
| 32-SiO$_2$ | 3.46 | 10.31 | 17.24 |
| 32-SiO$_2$ | 3.51 | 9.93 | 17.56 |
| 36-SiO$_2$ | 1.90 | 4.58 | 11.29 |
| 38-SiO$_2$ | 3.58 | 10.45 | 17.80 |
| 39-SiO$_2$ | 2.65 | 7.07 | 13.44 |
| 40-SiO$_2$ | 2.96 | 6.25 | 13.71 |
| 40-SiO$_2$ | 3.05 | 7.38 | 13.68 |
| 18-SiO$_2$ + 10 equiv. 15 | 1.47 | 4.48 | 10.49 |
| 18-SiO$_2$ + Ph$_2$Si(OEt)$_2$ | 1.44 | 4.07 | 9.71 |

[1]This value is the average GC yield of Me-9DA of the last four 1 mL fractions collected at the flow rate of 0.25 mL/min (ie. avg. of fractions 7-10, 17-20, 27-30, 37-40, 47-50, 57-60, 67-70).

Investigations into Alternative Screening Protocols with Constant or Variable Flow Rates Constant Flow Rate Screening Protocol:

The constant flow rate screening protocol is described below. It begins in an exact manner to the standard screening protocol but then after 30 minutes the flow rate is kept constant at 0.25 mL/min. The full experimental details follow below:

At 1 mL/min flow rate, collect 5×1 mL fractions (cycle time of 5 min)

Decrease the flow rate to 0.25 mL/min and collect 5×1 mL fractions (cycle time of 20 min)

Repeat 5×1 mL/min and 0.25 mL/min sequences one additional time (total time of cycles 25 min)

At a flow rate of 0.25 mL/min and collected samples for GC analysis at:
60-64 minutes
90-94 minutes
120-124 minutes
150-154 minutes
180-184 minutes
210-214 minutes and
240-244 minutes Total reaction time was 294 min.

Variable Flow Rate Screening Protocol:

The variable flow rate screening protocol is described below. It begins in an exact manner to the standard screening protocol but then after 50 minutes a flow rate of 2.5 mL/min is employed for 2 minutes. The experiment continues to cycle between 0.25 and 2.5 mL/min flow rates. The full experimental details follow below:

At 1.0 mL/min flow rate, collect 5×1 mL fractions (cycle time of 5 min)

Decrease the flow rate to 0.25 mL/min and collect 5×1 mL fractions (cycle time of 20 min)

Repeat 5×1.0 mL/min and 0.25 mL/min sequences one additional time (total time of cycle 50 min)

Increase the flow rate to 2.5 mL/min for 2 min (cycle time of 2 min)

Decrease the flow rate to 0.25 mL/min and collect 5×1 mL fractions (cycle time of 20 min)

Repeat 2.5 mL/min for 2 min followed by 5×0.25 mL/min sequences seven additional times (total time of cycle 226 min)

Decrease the flow rate to 0.05 mL/min and collect 3×1 mL fractions (cycle time of 60 min)

Decrease the flow rate to 0.017 mL/min and collect 1 mL fractions (cycle time of 60 min)

Total reaction time was 360 min.

Note 1: Using the 2.5 mL/min flow rate for 2 min corresponds to 5 mL total volume which was the same volume passing over the catalyst bed as using the flow rate of 1 mL/min for 5 min which was employed in the standard screening protocol.

Note 2: Selective fractions throughout the sequence were analyzed by GC and the GC area percent (%) of Me-9DA in each fraction was reported and graphed. It should be further noted that 20% Me-9DA by GC represents the theoretical maximum yield of Me-9DA for this equilibrium process when 3 equivalents of 1-octene is employed.

Results for the Various Screening Protocols:

The results comparing the standard screening protocol, to the constant flow rate screening protocol and the variable flow rate screening protocol are shown in FIG. 19 for catalyst 24-SiO$_2$. The GC yields of Me-9DA are plotted against the volume of substrate solution passed through the catalyst bed. The results clearly indicate that there is a beneficial aspect to cycling between a faster and a slower flow rate (both the standard and variable flow rate screening protocols), rather than simply keeping a slow constant flow rate.

Self-Metathesis of Internal Olefin Substrate 5-C$_{14}$ Via Continuous Flow Through a Fixed Catalyst Bed Employing a HPLC System:

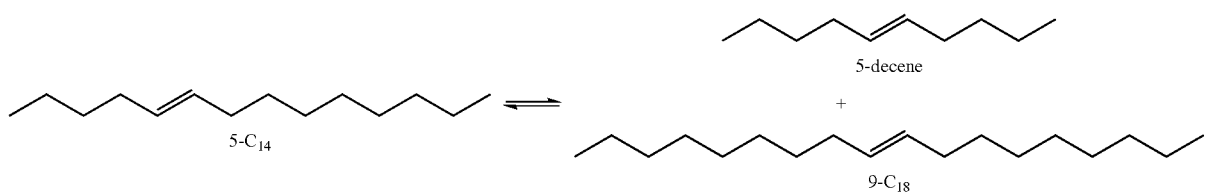

Equilibrium process with max conversion of 50%

Inside the glovebox, 25 mg (~0.0005 mmol) of solid-supported Ru catalyst was weighed. This was diluted with 100 mg of inert filler (either celite or alumina). This mixture was packed into an empty HPLC column (75 mm long×4.6 mm diameter). The remainder void volume was packed with alumina. A guard column was also prepared in the glovebox by packing a 2$^{nd}$ HPLC column (125 mm long×4.6 mm diameter) with alumina. These columns were removed from the glovebox and connected to the HPLC instrument so that the guard column was first in line and then the catalyst column. The flow through the columns were in an upwards direction. The flow conditions employed were as follows:

constant flow rate of 0.2 mL/min at room temperature (~22° C.). 1 to 5 mL fractions were collected throughout the experiment and analyzed by GC for % conversion.

In the instance of the one reaction that was heated (298-097), the approximate temperature of the catalyst bed column was 30-35° C. In order to achieve this temperature, the guard column was placed horizontal within the heated column compartment of the HPLC set-up and this flowed into an insulated catalyst column that was vertical. The flow rate employed for this experiment was 0.5 mL/min and a similar fraction collection was employed.

Results for the self-metathesis of the 5-C14 substrate employing catalysts 19-SiO$_2$ (various conditions), 24-SiO$_2$ and 25—SiO$_2$ are shown in FIG. 20. From these results, it is obvious that catalyst 19—SiO$_2$ is the better of the 3 catalysts for this reaction. FIG. 21 shows the turnover number (TON) as a function of time for the reactions shown in FIG. 20 with catalyst 19-SiO$_2$. TON of 230,000 and still increasing at the time the reaction was stopped were obtained.

What is claimed is:

1. A supported catalyst complex comprising:
a catalyst composed of a Group 8 transition metal complex comprising a Group 8 transition metal, a labile ligand and a non-labile ligand; and
a support;
wherein the metal complex and the support are linked together by one or more linkers, in which one of the linkers connects the labile ligand of the complex to the support and the same or a different linker connects the non-labile ligand of the complex to the support,
wherein the Group 8 transition metal is ruthenium, the non-labile ligand is an N-heterocyclic carbene ligand and the labile ligand is selected from an alkylidene and a chelating alkylidene ligand.

2. The supported catalyst of claim 1, wherein the linkers have the structure -A-Fn, wherein A is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups, and Fn is a functional group selected from trialkoxysilyl, siloxy, siloxane, amide, urea, ether, ester, anhydride, carbamate, or a combination thereof.

3. The supported catalyst of claim 2, wherein the linkers have the structure -A-Si(O(CH$_2$)$_n$CH$_3$)$_3$, wherein n is an integer ranging from 0-3 and A is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein hetero atoms and/or functional groups may be present in either the aryl or the alkyl portions of the alkylene and arylalkylene groups.

4. The supported catalyst of claim 1, wherein the support is selected from silicas, silicates, aluminas, aluminum oxides, silica-aluminas, aluminosilicates, zeolites, titanias, titanium dioxide, magnetite, magnesium oxides, boron oxides, clays, zirconias, zirconium dioxide, carbon, polymers, or a combination thereof.

5. The supported catalyst of claim 1, wherein the Group 8 transition metal complex has the structure

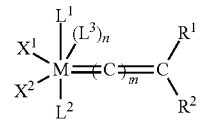

wherein,
M is ruthenium;
L$^1$ is an N-heterocyclic carbene ligand;
L$^2$ and L$^3$ are independently selected from neutral electron donor ligands;
n is 0 or 1, such that L$^3$ may or may not be present;
m is 0, 1, or 2;
X$^1$ and X$^2$ are independently selected from anionic ligands; and
R$^1$ and R$^2$ are independently selected from hydrogen, hydrocarbyl, substituted hydrocarbyl, heteroatom-containing hydrocarbyl, substituted heteroatom-containing hydrocarbyl, and functional groups; wherein one or both of R$^1$ and R$^2$ may have the structure -(W)$_n$U$^+$V$^-$, in which W is selected from hydrocarbylene, substituted hydrocarbylene, heteroatom-containing hydrocarbylene, or substituted heteroatom-containing hydrocarbylene; U is a positively charged Group 15 or Group 16 element substituted with hydrogen, hydrocarbyl, substituted hydrocarbyl, heteroatom-containing hydrocarbyl, or substituted heteroatom-containing hydrocarbyl; V is a negatively charged counterion; and n is zero or 1,
wherein any two or more of X$^1$, X$^2$, L$^1$, L$^2$, L$^3$, R$^1$, and R$^2$ can be taken together to form one or more cyclic groups, and further wherein any two or more of X$^1$, X$^2$, L$^1$, L$^2$, L$^3$, R$^1$, and R$^2$ is attached to the support via the linkers.

6. The supported catalyst of claim 5, wherein at least one linker is attached to the support and to at least one of L$^1$, L$^2$, and L$^3$.

7. The supported catalyst of claim 5, wherein at least one of L$^1$, L$^2$, and L$^3$ is an N-heterocyclic carbene ligand.

8. The supported catalyst of claim 1, wherein the Group 8 transition metal complex comprises an N-heterocyclic carbene ligand and a chelating alkylidene ligand.

9. The supported catalyst of claim 8, wherein at least one linker is attached to the support and to the N-heterocyclic carbene ligand and at least one linker is attached to the support and to the chelating alkylidene ligand.

10. The supported catalyst of claim 1, wherein the metal complex comprises a chelating alkylidene ligand.

11. The supported catalyst of claim 10, wherein the Group 8 transition metal complex has the structure

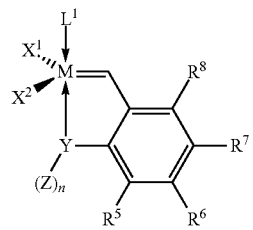

wherein,
M is ruthenium;
X$^1$ and X$^2$ are independently selected from anionic ligands;

L¹ is an N-heterocyclic carbene ligand;
Y is a heteroatom selected from N, O, S, and P;
R⁵, R⁶, R⁷, and R⁸ are each, independently, selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl, perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, borate, or -A-Fn, wherein A is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein heteroatoms and/or functional groups may be present in either the aryl or the alkyl portions of the alkylene and arylalkylene groups, and Fn is a functional group selected from trialkoxysilyl, siloxy, siloxane, amide, urea, ether, ester, anhydride, carbamate, or a combination thereof; and any combination of R⁵, R⁶, R⁷, and R⁸ can be linked to form one or more cyclic groups;

n is 1 or 2, such that n is 1 for the divalent heteroatoms O or S, and n is 2 for the trivalent heteroatoms N or P;

Z is a group selected from hydrogen, alkyl, aryl, functionalized alkyl, functionalized aryl where the functional group(s) may independently be one or more or the following: alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, borate, or -A-Fn, wherein A is a divalent hydrocarbon moiety selected from alkylene and arylalkylene, wherein the alkyl portion of the alkylene and arylalkylene groups can be linear or branched, saturated or unsaturated, cyclic or acyclic, and substituted or unsubstituted, wherein the aryl portion of the arylalkylene can be substituted or unsubstituted, and wherein heteroatoms and/or functional groups may be present in either the aryl or the alkyl portions of the alkylene and arylalkylene groups, and Fn is a functional group selected from trialkoxysilyl, siloxy, siloxane, amide, urea, ether, ester, anhydride, carbamate, or a combination thereof; and wherein any combination or combinations of X¹, X², L¹, Y, Z, R⁵, R⁶, R⁷, and R⁸ are linked to the support.

12. The supported catalyst of claim 11, wherein
X¹ and X² are halide;
L¹ is an N-heterocyclic carbene ligand having the structure

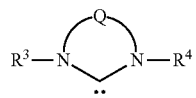

wherein Q is —CR¹¹R¹²—CR¹³R¹⁴— or —CR¹¹=CR¹³—, wherein R¹¹, R¹², R¹³, and R¹⁴ are independently selected from hydrogen, hydrocarbyl, substituted hydrocarbyl, heteroatom-containing hydrocarbyl, substituted heteroatom-containing hydrocarbyl, and functional groups, or wherein any two of R¹¹, R¹², R¹³, and R¹⁴ may be linked together to form a substituted or unsubstituted, saturated or unsaturated ring, or wherein one or more of R¹¹, R¹², R¹³, and R¹⁴ comprises one or more of the linkers and R³ and R⁴ are unsubstituted phenyl or phenyl substituted with one or more substituents selected from C₁-C₂₀ alkyl, substituted C₁-C₂₀ alkyl, C₁-C₂₀ heteroalkyl, substituted C₁-C₂₀ heteroalkyl, C₅-C₂₄ aryl, substituted C₅-C₂₄ aryl, C₅-C₂₄ heteroaryl, C₆-C₂₄ aralkyl, C₆-C₂₄ alkaryl, or halide;

Y is a heteroatom selected from N or O; and
n is 1 or 2, such that n is 1 for the divalent heteroatom O, and n is 2 for the trivalent heteroatom N.

13. The supported catalyst of claim 11, wherein
X¹ and X² are chlorides;
L¹ is an N-heterocyclic carbene ligand having the structure,

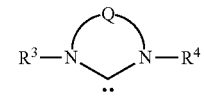

wherein Q is —CR¹¹R¹²—CR¹³R¹⁴— and R¹¹, R¹², R¹³, and R¹⁴ are independently selected from hydrogen or one or more of the linkers, and R³ and R⁴ are selected from 2,4,6-trimethylphenyl and 2,6-diisopropylphenyl;
Y is oxygen; and
n is 1.

14. A method of performing an olefin metathesis reaction, comprising contacting the supported catalyst of claim 1 with an olefin.

15. The method of claim 14, wherein the olefin metathesis reaction is selected from ring-closing metathesis, ring-opening metathesis polymerization, cross metathesis, self-metathesis, acyclic diene metathesis polymerization, and combinations thereof.

16. The supported catalyst of claim 1, prepared by reacting a Group 8 transition metal complex containing one or more linker moieties with the support, wherein the Group 8 transition metal complex containing one or more linker moieties has the structure:

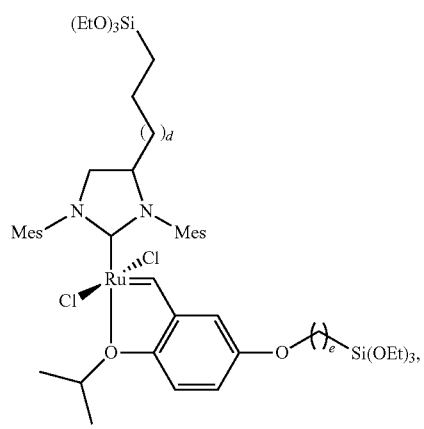

wherein d is 1, 4, or 9 and e is 3, 6, or 11;

81

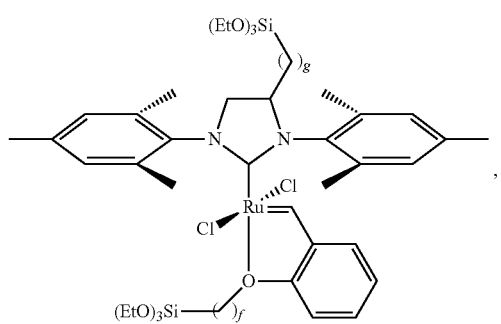

wherein f is 3, 6 or 11 and g is 3, or f is 6 and g is 6;

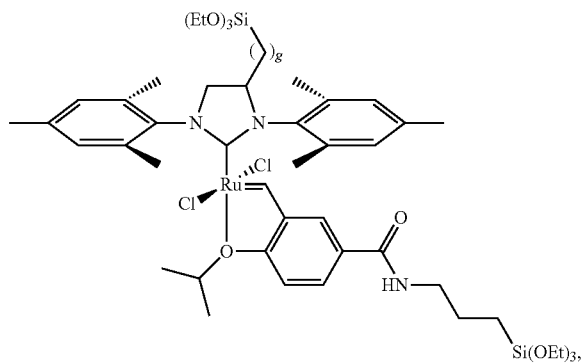

wherein g is 3, 6, or 11;

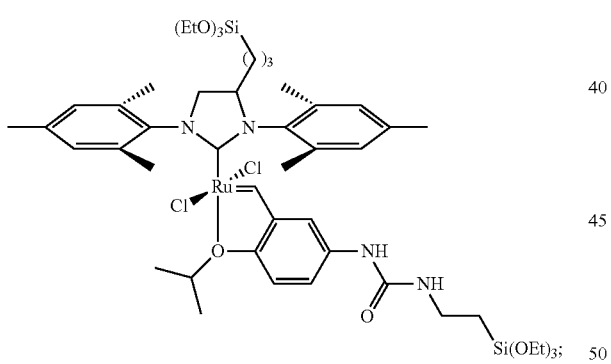

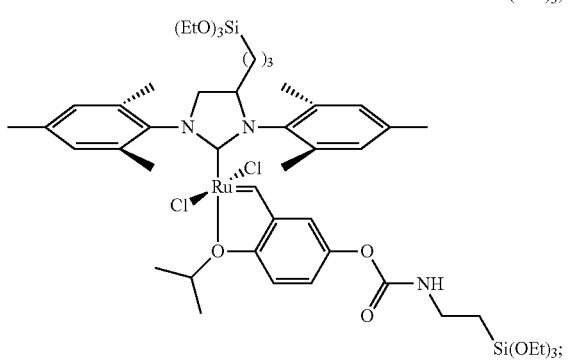

or

82

-continued

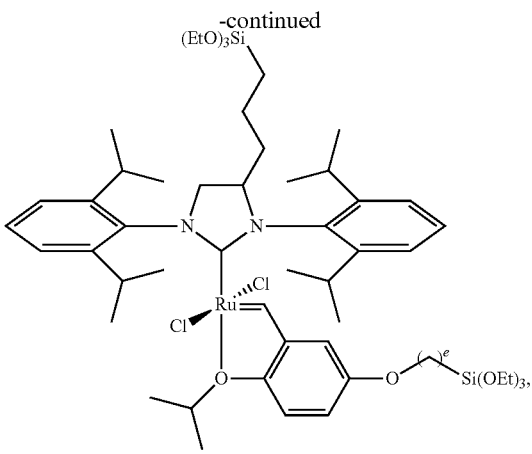

wherein e is 3 or 6.

17. The supported catalyst of claim 16, wherein the Group 8 transition metal complex containing one or more linker moieties has the structure:

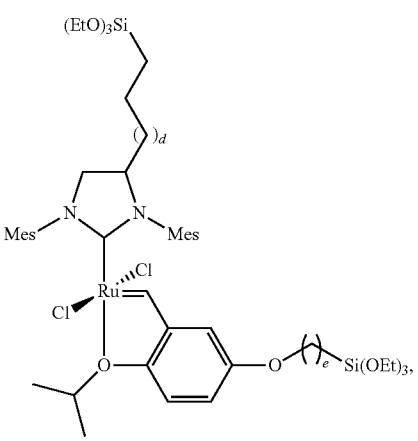

wherein d is 1, 4, or 9 and e is 3, 6, or 11.

18. The supported catalyst of claim 16, wherein the Group 8 transition metal complex containing one or more linker moieties has the structure:

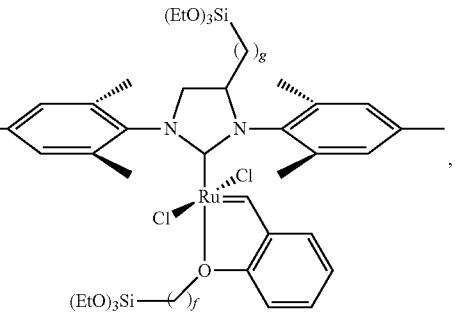

wherein f is 3, 6 or 11 and g is 3, or f is 6 and g is 6.

19. The supported catalyst of claim 16, wherein the Group 8 transition metal complex containing one or more linker moieties has the structure:

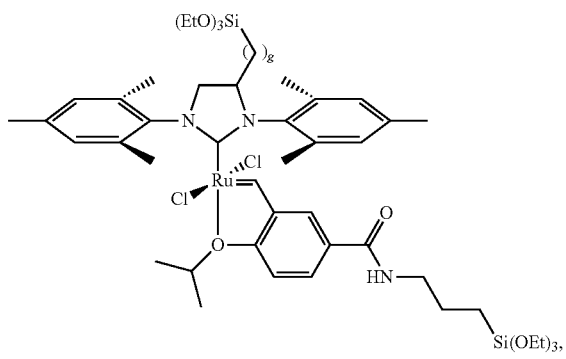

wherein g is 3, 6, or 11.

20. The supported catalyst of claim 16, wherein the Group 8 transition metal complex containing one or more linker moieties has the structure:

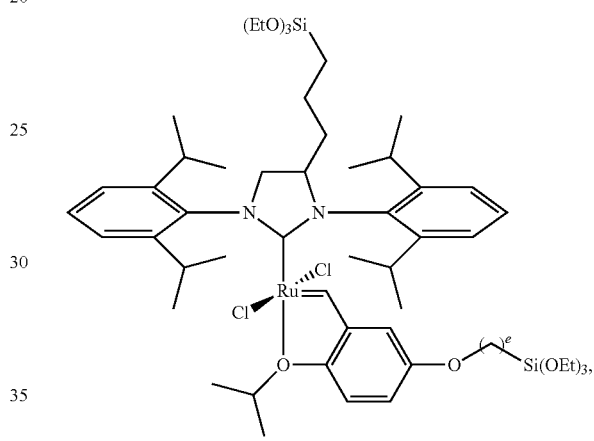

21. The supported catalyst of claim 16, wherein the Group 8 transition metal complex containing one or more linker moieties has the structure:

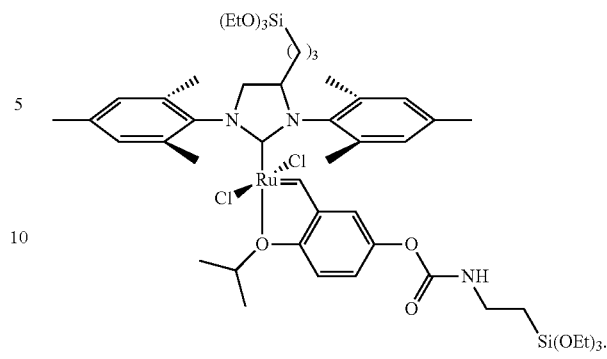

22. The supported catalyst of claim 16, wherein the Group 8 transition metal complex containing one or more linker moieties has the structure:

wherein e is 3 or 6.

* * * * *